(12) United States Patent
Gotoh et al.

(10) Patent No.: US 9,073,850 B2
(45) Date of Patent: Jul. 7, 2015

(54) POLYMERIZABLE COMPOUND

(75) Inventors: Yasuyuki Gotoh, Tokyo (JP); Maiko Matsukuma, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 93 days.

(21) Appl. No.: 13/594,873

(22) Filed: Aug. 27, 2012

(65) Prior Publication Data

US 2013/0134354 A1 May 30, 2013

(30) Foreign Application Priority Data

Nov. 24, 2011 (JP) ................................ 2011-256266

(51) Int. Cl.
| | |
|---|---|
| C09K 19/30 | (2006.01) |
| C09K 19/12 | (2006.01) |
| C07C 69/54 | (2006.01) |
| C07C 69/96 | (2006.01) |
| C08F 20/30 | (2006.01) |
| C08F 22/10 | (2006.01) |
| C07C 69/653 | (2006.01) |
| C09K 19/04 | (2006.01) |

(52) U.S. Cl.
CPC .............. *C07C 69/54* (2013.01); *C07C 69/96* (2013.01); *C09K 19/12* (2013.01); *C09K 2019/0448* (2013.01); *C09K 2019/122* (2013.01); *C09K 2019/123* (2013.01); *C08F 20/30* (2013.01); *C08F 22/10* (2013.01); *C07C 69/653* (2013.01)

(58) Field of Classification Search
CPC ...... C07C 69/54; C07C 69/96; C07C 69/653; C09K 19/12; C09K 19/30; C09K 2019/0448; C09K 2019/122; C09K 2019/123; C08F 20/30; C08F 22/10
USPC .............. 252/299.01, 299.6, 299.63, 299.66; 428/1.1; 349/86, 182; 526/72, 314, 526/319–321; 560/95, 190, 193–195
See application file for complete search history.

(56) References Cited

U.S. PATENT DOCUMENTS

| 8,304,035 B2 * | 11/2012 | Bernatz et al. ................. 428/1.1 |
| 8,425,800 B2 * | 4/2013 | Hirata et al. ............... 252/299.6 |
| 2010/0309423 A1 | 12/2010 | Bernatz et al. |
| 2013/0134354 A1 * | 5/2013 | Gotoh et al. ............... 252/299.5 |

FOREIGN PATENT DOCUMENTS

| DE | WO 2011050893 | * 5/2011 | ............... 252/299.66 |
| EP | 1889894 | 2/2008 | |
| JP | 08-231562 | 9/1996 | |
| JP | 2003-307720 | 10/2003 | |
| JP | 2004-131704 | 4/2004 | |
| JP | 2006-133619 | 5/2006 | |
| JP | 2010-159324 | 7/2010 | |
| JP | 2011-162571 | 8/2011 | |
| JP | 2011-184417 | 9/2011 | |
| JP | 2011-202168 | 10/2011 | |
| JP | 2011-225665 | 11/2011 | |
| JP | 2011-227187 | 11/2011 | |
| JP | 2012-077200 | 4/2012 | |
| JP | 2012-082349 | 4/2012 | |
| JP | 2012-082350 | 4/2012 | |
| JP | 2012-241124 | 12/2012 | |
| WO | 9322397 | 11/1993 | |
| WO | 2009104468 | 8/2009 | |
| WO | 2011035842 | 3/2011 | |
| WO | 2011050898 | 5/2011 | |
| WO | 2011160765 | 12/2011 | |

OTHER PUBLICATIONS

Bardosova,M. et al., "Thin films of liquid crystal fumarates and a related acrylate", Thin Solid Films, 1997, vol. 300, p. 234-239.
"Written Opinion of the International Search Authority (PCT/ISA/237)", mailed on Feb. 5, 2013, p. 1-p. 9.
"International Search Report (Form PCT/ISA/210)", published on Feb. 5, 2013, p. 1-p. 6.
"International Search Report (Form PCT/ISA/210)", mailed on Feb. 5, 2013, p. 1-p. 5.

* cited by examiner

*Primary Examiner* — Geraldina Visconti
(74) *Attorney, Agent, or Firm* — Jianq Chyun IP Office

(57) ABSTRACT

The invention provides a compound having two polymerizable groups, wherein one is bonded directly to the ring and the other is bonded to the ring through a spacer, as a compound in which the polymerizability is not decreased and the solubility is high in a liquid crystal composition. A compound represented by formula (1), wherein

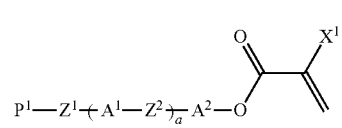

in formula (1), for example, $A^1$ and $A^2$ are 1,4-phenylene in which at least one hydrogen has been replaced by fluorine; $Z^1$ is alkylene having 1 to 12 carbons; $Z^2$ is alkylene having 1 to 12 carbons; $X^1$ is hydrogen, fluorine, methyl or trifluoromethyl; $P^1$ is a polymerizable group; and a is an integer from 0 to 3.

16 Claims, No Drawings

POLYMERIZABLE COMPOUND

CROSS-REFERENCE TO RELATED APPLICATIONS

This application claims the priority benefit of Japan application serial no. 2011-256266, filed on Nov. 24, 2011. The entirety of the above-mentioned patent application is hereby incorporated by reference herein and made a part of this specification.

BACKGROUND OF THE INVENTION

1. Technical Field

The invention relates to a polymerizable compound having two polymerizable groups, wherein one is bonded directly to the ring and the other is bonded to the ring through a spacer (a bonding group), a composition including the polymerizable compound, a polymer obtained from the composition, and their use.

2. Technical Background

A liquid crystal display device typified by a liquid crystal display panel, a liquid crystal display module and so forth utilizes optical anisotropy, dielectric anisotropy and so forth, those of which are possessed by a liquid crystal compound. An operating mode of this liquid crystal display device includes a PC (phase change) mode, a TN (twisted nematic) mode, a STN (super twisted nematic) mode, a BTN (bistable twisted nematic) mode, an ECB (electrically controlled birefringence) mode, an OCB (optically compensated bend) mode, an IPS (in-plane switching) mode, a FFS (fringe field switching) mode and a VA (vertical alignment) mode.

A liquid crystal display device containing a liquid crystal composition to which a polymerizable compound is added is also known. In a liquid crystal display device having a PSA (polymer sustained alignment) mode, for example, a small amount of a polymerizable compound (for example, approximately 0.3% by weight to approximately 1% by weight) is added to a liquid crystal composition, which is then introduced to a liquid crystal display cell. The cell is irradiated usually with ultraviolet light under the conditions of applied voltage between the electrodes, polymerizing the polymerizable compound and forming a polymer structure in the cell. A liquid crystal display device having an improved screen burn-in and a decreased response time is obtained by this method.

This method is applied to a variety of liquid crystal display devices, and modes such as PS-TN, PS-IPS, PS-FFS, PSA-VA and PSA-OCB are known. A polymerizable compound that is added to a liquid crystal composition for use in the devices having these modes has a rigid structure. It is said that the compound generally has a high ability for orienting liquid crystal molecules. On the other hand, the compound has a poor solubility in the liquid crystal composition and a large amount of the polymerizable compound cannot be added (Patent document No. 1 to Patent document No. 5).

PRIOR ART

Patent Document

Patent document No. 1: JP 2003-307720 A.
Patent document No. 2: JP 2004-131704 A.
Patent document No. 3: JP 2006-133619 A.
Patent document No. 4: EP 1,889,894 A.
Patent document No. 5: JP 2010-537256 A.

SUMMARY OF THE INVENTION

Subject to be Solved by the Invention

One of the objects of the invention is to provide a polymerizable compound in which the polymerizability is not decreased and the solubility is high in a liquid crystal composition. Another object is to provide a liquid crystal composition including the compound and a liquid crystal display device containing the composition. A further object is to provide a polymer obtained from the composition including the compound, an optical device prepared from the polymer and so forth.

Means for Solving the Subject

The inventors studied the backbone structure of a polymerizable compound used for a display device having a PSA mode or the like and found that the compound (1) did not decrease the polymerizability and increased the solubility in a liquid crystal composition. The compound (1) has two polymerizable groups, where one is bonded directly to the ring and the other is bonded to the ring through a bonding group. The compound (1) exhibited a sufficient polymerizability by having a polymerizable group bonded directly to the ring. The compound (1) exhibited a high solubility in a liquid crystal composition by having a bonding group such as ester or alkylene between the ring and the polymerizable group.

A compound represented by formula (1).

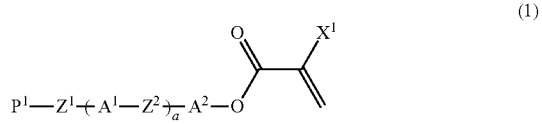

(1)

In formula (1), $A^1$ is independently a single bond, 1,4-cyclohexylene, 1,4-cyclohexenylene, 1,4-phenylene, naphthalene-2,6-diyl, tetrahydropyran-2,5-diyl, 1,3-dioxane-2,5-diyl, pyrimidine-2,5-diyl or pyridine-2,5-diyl, and in these groups at least one hydrogen may be replaced by halogen, alkyl having 1 to 12 carbons or alkyl having 1 to 12 carbons in which at least one hydrogen has been replaced by halogen;

$A^2$ is 1,4-phenylene or naphthalene-2,6-diyl, and in these groups at least one hydrogen may be replaced by halogen, alkyl having 1 to 12 carbons or alkyl having 1 to 12 carbons in which at least one hydrogen has been replaced by halogen;

$Z^1$ is alkylene having 1 to 12 carbons, and in the alkylene at least one —$CH_2$— may be replaced by —O—, —COO—, —OCO—, —OCOO—, —CH=CH— or —C≡C—;

$Z^2$ is independently a single bond or alkylene having 1 to 12 carbons, and in the alkylene at least one —$CH_2$— may be replaced by —O—, —COO—, —OCO—, —OCOO—, —CH=CH— or —C≡C—;

at least one of $Z^1$ and $Z^2$ has an unsaturated bond, when all of $A^1$ and $A^2$ are groups in which no hydrogen is replaced;

$X^1$ is hydrogen, fluorine, methyl or trifluoromethyl;

$P^1$ is a polymerizable group; and a is an integer from 0 to 3.

Effect of the Invention

The compound (1) satisfies many advantages such that the polymerizability is not decreased and the solubility is high in a liquid crystal composition. A liquid crystal display device having a short response time and an improved screen burn-in can be produced by use of a liquid crystal composition including the compound (1) as a starting material.

DESCRIPTION OF THE EMBODIMENTS

Usage of the terms in this specification is as follows. The term "a liquid crystal compound" is a generic term for a compound having a liquid crystal phase, and also for a compound having no liquid crystal phases but useful as a component of a liquid crystal composition. "A non-polymerizable liquid crystal composition" means a liquid crystal composition including a liquid crystal compound which does not have a polymerizable group. The terms, a liquid crystal compound, a liquid crystal composition and a liquid crystal display device may be expressed as a compound, a composition and a device, respectively. A compound represented by formula (1) may be expressed as the compound (1) or the compound of formula (1). The same applies to other formulas. "The compound (1)" means one compound or two or more compounds represented by formula (1). The same applies to a compound represented by other formula. The group represented by formula (P-1) may be abbreviated to "the group (P-1)". The same applies to a group represented by other formula. In formula (2) to formula (7), the symbol $B^{11}$, $C^{11}$ or the like surrounded by a hexagonal shape corresponds to the ring $B^{11}$, the ring $C^{11}$ or the like, respectively. A plurality of $R^{11}$ were described in the same or different formulas. Two groups represented by arbitrary two of $R^{11}$ may be the same or different in these compounds. The same rule applies to symbols such as the ring $A^1$ and $Z^2$. The ratio of an additive added to a composition means a weight percentage (% by weight) based on the total weight of the liquid crystal composition. When it is said that at least one —$CH_2$— may be replaced by —O—, the replacement of adjacent —$CH_2$— with —O— and the replacement of —$CH_2$— next to —O— with —O— are not included. "Monofunctional" means that there is one polymerizable group, and "polyfunctional" means that there are two or more polymerizable groups.

The term "2-fluoro-1,4-phenylene" means the following two divalent groups. Fluorine may be facing left or facing right in formula (1) and so forth. The rule applies to an asymmetric divalent group such as tetrahydropyran-2,5-diyl.

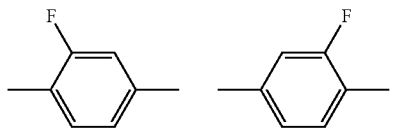

The invention includes the following items.
1. A compound represented by formula (1), wherein

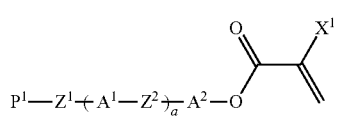 (1)

in formula (1),
$A^1$ is independently a single bond, 1,4-cyclohexylene, 1,4-cyclohexenylene, 1,4-phenylene, naphthalene-2,6-diyl, tetrahydropyran-2,5-diyl, 1,3-dioxane-2,5-diyl, pyrimidine-2,5-diyl or pyridine-2,5-diyl, and in these groups at least one hydrogen may be replaced by halogen, alkyl having 1 to 12 carbons or alkyl having 1 to 12 carbons in which at least one hydrogen has been replaced by halogen;

$A^2$ is 1,4-phenylene or naphthalene-2,6-diyl, and in these groups at least one hydrogen may be replaced by halogen, alkyl having 1 to 12 carbons or alkyl having 1 to 12 carbons in which at least one hydrogen has been replaced by halogen;

$Z^1$ is alkylene having 1 to 12 carbons, and in the alkylene at least one —$CH_2$— may be replaced by —O—, —COO—, —OCO—, —OCOO—, —CH=CH— or —C≡C—;

$Z^2$ is independently a single bond or alkylene having 1 to 12 carbons, and in the alkylene at least one —$CH_2$— may be replaced by —O—, —COO—, —OCO—, —OCOO—, —CH=CH— or —C≡C—;

at least one of $Z^1$ and $Z^2$ has an unsaturated bond, when all of $A^1$ and $A^2$ are groups in which no hydrogen is replaced;

$X^1$ is hydrogen, fluorine, methyl or trifluoromethyl;

$P^1$ is a polymerizable group; and a is an integer from 0 to 3.

2. The compound according to item 1, wherein in formula (1) according to item 1, $A^1$ is 1,4-cyclohexylene, 1,4-phenylene or naphthalene-2,6-diyl, and in these groups at least one hydrogen may be replaced by fluorine, chlorine, alkyl having 1 to 4 carbons or alkyl having 1 to 4 carbons in which at least one hydrogen has been replaced by halogen;

$A^2$ is 1,4-phenylene or naphthalene-2,6-diyl, and in these groups at least one hydrogen may be replaced by fluorine, chlorine, alkyl having 1 to 4 carbons or alkyl having 1 to 4 carbons in which at least one hydrogen has been replaced by halogen;

$Z^1$ is alkylene having 1 to 12 carbons, and in the alkylene at least one —$CH_2$— may be replaced by —O—, —COO—, —OCO—, —OCOO—, —CH=CH— or —C≡C—;

$Z^2$ is a single bond or alkylene having 1 to 12 carbons, and in the alkylene at least one —$CH_2$— may be replaced by —O—, —COO—, —OCO—, —OCOO—, —CH=CH— or —C≡C—;

at least one of $Z^1$ and $Z^2$ is alkylene having 1 to 12 carbons in which at least one —$CH_2$— has been replaced by —COO—, —OCO—, —OCOO—, —CH=CH— or —C≡C—;

$X^1$ is hydrogen or methyl;

$P^1$ is a group selected from groups represented by formula (P-1) to formula (P-3); and

 (P-1)

 (P-2)

 (P-3)

a is 1.

3. The compound according to item 1, wherein in formula (1) according to item 1, $A^1$ is 1,4-cyclohexylene, 1,4-phenylene or naphthalene-2,6-diyl, and in these groups at least one hydrogen may be replaced by fluorine, chlorine, alkyl having 1 to 4 carbons or alkyl having 1 to 4 carbons in which at least one hydrogen has been replaced by fluorine;

$A^2$ is 1,4-phenylene or naphthalene-2,6-diyl, and in these groups at least one hydrogen may be replaced by fluorine, chlorine, alkyl having 1 to 4 carbons or alkyl having 1 to 4 carbons in which at least one hydrogen has been replaced by fluorine;

$Z^1$ is alkylene having 1 to 7 carbons, and in the alkylene at least one —CH$_2$— may be replaced by —O— or —CH=CH—;

$Z^2$ is a single bond or alkylene having 1 to 7 carbons, and in the alkylene at least one —CH$_2$— may be replaced by —O— or —CH=CH—;

at least one of $Z^1$ and $Z^2$ is alkylene having 1 to 7 carbons in which at least one —CH$_2$— has been replaced by —CH=CH—;

$X^1$ is hydrogen or methyl;

$P^1$ is a group selected from groups represented by formula (P-1) to formula (P-3); and

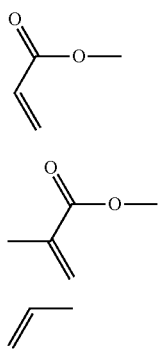

(P-1)

(P-2)

(P-3)

a is 1.

4. The compound according to item 1, wherein the compound is represented by formula (1-1), wherein

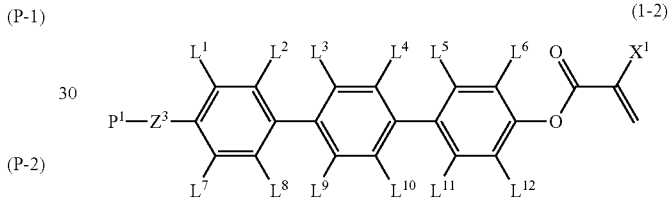

(1-1)

in formula (1-1), $Z^3$ is alkylene having 1 to 7 carbons, and in the alkylene at least one —CH$_2$— may be replaced by —O—, —COO—, —OCO—, —OCOO—, —CH=CH— or —C≡C—;

$Y^1$ to $Y^8$ are independently hydrogen, fluorine, methyl or trifluoromethyl;

$Z^3$ is alkylene having 1 to 7 carbons in which at least one —CH$_2$— has been replaced by —COO—, —OCO—, —OCOO—, —CH=CH— or —C≡C, when all of $Y^1$ to $Y^8$ are hydrogen.

$X^1$ is hydrogen, fluorine, methyl or trifluoromethyl; and $P^1$ is a polymerizable group.

5. The compound according to item 4, wherein in formula (1-1) according to item 4, $Z^3$ is alkylene having 1 to 7 carbons, and in the alkylene at least one —CH$_2$— has been replaced by —COO—, —OCO—, —OCOO—, —CH=CH— or —C≡C—, and at least one —CH$_2$— may be replaced by —O—; and $Y^1$ to $Y^8$ are independently hydrogen, fluorine, methyl or trifluoromethyl.

6. The compound according to item 4, wherein in formula (1-1) according to item 4, $Z^3$ is alkylene having 1 to 7 carbons, and in the alkylene at least one —CH$_2$— may be replaced by —O—; $Y^1$ to $Y^8$ are independently hydrogen, fluorine, methyl or trifluoromethyl; and at least one of $Y^1$ to $Y^8$ is fluorine, methyl or trifluoromethyl.

7. The compound according to item 5, wherein in formula (1-1) according to item 4, $X^1$ is hydrogen or methyl; and all of $Y^1$ to $Y^8$ are hydrogen.

8. The compound according to item 5, wherein in formula (1-1) according to item 4, $P^1$ is a group selected from groups represented by formula (P-1) and formula (P-2) according to item 3.

9. The compound according to item 5, wherein in formula (1-1) according to item 4, $P^1$ is a group represented by formula (P-3) according to item 3.

10. The compound according to item 1, wherein the compound is represented by formula (1-2), wherein

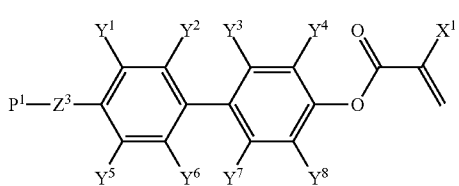

(1-2)

in formula (1-2), $Z^3$ is alkylene having 1 to 7 carbons, and in the alkylene at least one —CH$_2$— may be replaced by —O—, —COO—, —OCO—, —OCOO—, —CH=CH— or —C≡C—;

$L^1$ to $L^{12}$ are independently hydrogen, fluorine, methyl or trifluoromethyl;

$Z^3$ is alkylene having 1 to 7 carbons in which at least one —CH$_2$— has been replaced by —COO—, —COO—, —OCOO—, —CH=CH— or —C≡C—, when all of $L^1$ to $L^{12}$ are hydrogen;

$X^1$ is hydrogen, fluorine, methyl or trifluoromethyl; and $P^1$ is a polymerizable group.

11. The compound according to item 10, wherein in formula (1-2) according to item 10, $Z^3$ is alkylene having 1 to 7 carbons, and in the alkylene at least one —CH$_2$— has been replaced by —COO—, —OCO—, —OCOO—, —CH=CH— or —C≡C— and at least one —CH$_2$— may be replaced by —O—; and $L^1$ to $L^{12}$ are independently hydrogen, fluorine, methyl or trifluoromethyl.

12. The compound according to item 10, wherein in formula (1-2) according to item 10, $Z^3$ is alkylene having 1 to 7 carbons, and in the alkylene at least one —CH$_2$— may be replaced by —O—; $L^1$ to $L^{12}$ are independently hydrogen, fluorine, methyl or trifluoromethyl; and at least one of $L^1$ to $L^{12}$ is fluorine, methyl or trifluoromethyl.

13. The compound according to item 11, wherein in formula (1-2) according to item 10, $X^1$ is hydrogen or methyl; and all of $L^1$ to $L^{12}$ are hydrogen.

14. The compound according to item 11, wherein in formula (1-2) according to item 10, $P^1$ is a group selected from groups represented by formula (P-1) and formula (P-2) according to item 3.

15. The compound according to item 11, wherein in formula (1-2) according to item 10, $P^1$ is a group represented by formula (P-3) according to item 3.

16. A composition including the compound according to any one of items 1 to 15.

17. The composition according to item 16, wherein the compound according to any one of items 1 to 15 is added to a non-polymerizable liquid crystal composition.

18. The composition according to item 16 or 17, further including at least one compound selected from the group of compounds represented by formula (2) to formula (4), wherein

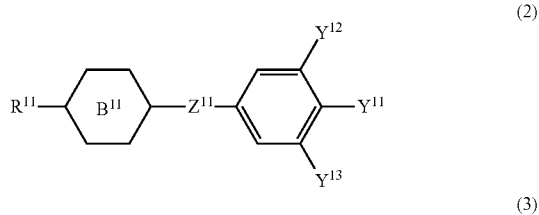
(2)

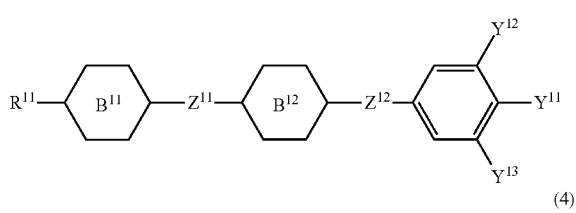
(3)

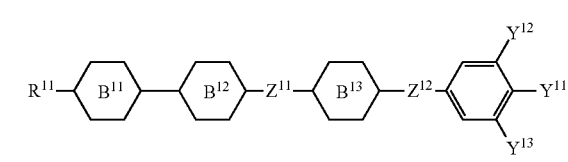
(4)

in formula (2) to formula (4), $R^{11}$ is independently alkyl having 1 to 10 carbons or alkenyl having 2 to 10 carbons, and in the alkyl and alkenyl at least one hydrogen may be replaced by fluorine and at least one —$CH_2$— may be replaced by —O—;

the ring $B^{11}$, the ring $B^{12}$ and the ring $B^{13}$ are independently 1,4-cyclohexenylene, 1,3-dioxane-2,5-diyl, tetrahydropyran-2,5-diyl, or 1,4-phenylene in which at least one hydrogen may be replaced by fluorine;

$Z^{11}$ and $Z^{12}$ are independently —$(CH_2)_2$—, —$(CH_2)_4$—, —COO—, —$CF_2O$—, —$OCF_2$—, —CH=CH—, —C≡C—, —$CH_2O$— or a single bond;

$Y^{11}$ is independently fluorine, chlorine, —$OCF_3$, —$OCHF_2$, —$CF_3$, —$CHF_2$, —$CH_2F$, —$OCF_2CHF_2$ or —$OCF_2CHFCF_3$; and $Y^{12}$ and $Y^{13}$ are independently hydrogen or fluorine.

19. The composition according to item 16, 17 or 18, further including at least one compound selected from the group of compounds represented by formula (5) to formula (7), wherein

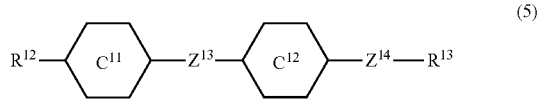
(5)

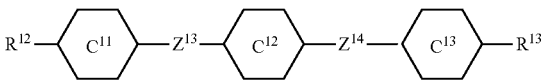
(6)

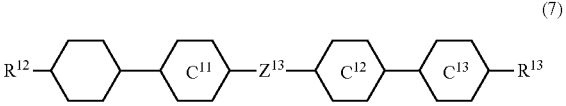
(7)

in formula (5) to formula (7), $R^{12}$ and $R^{13}$ are independently alkyl having 1 to 10 carbons or alkenyl having 2 to 10 carbons, and in the alkyl and alkenyl at least one hydrogen may be replaced by fluorine and at least one —$CH_2$— may be replaced by —O—;

the ring $C^{11}$, the ring $C^{12}$ and the ring $C^{13}$ are independently 1,4-cyclohexenylene, 1,4-phenylene, 2-fluoro-1,4-phenylene or 2,5-difluoro-1,4-phenylene; and $Z^{13}$ and $Z^{14}$ are independently —$(CH_2)_2$—, —COO—, —CH=CH—, —C≡C— or a single bond.

20. A polymer obtained by the polymerization of the composition according to any one of items 1 to 15.

21. A polymer obtained by the polymerization of the composition according to any one of items 16 to 19.

22. A liquid crystal display device containing at least one selected from the group of the compound according to any one of items 1 to 15, the composition according to any one of items 16 to 19, and the polymer according to item 20 or 21.

23. Use of at least one selected from the group of the compound according to any one of items 1 to 15, the composition according to any one of items 16 to 19, and the polymer according to item 20 or 21, for a liquid crystal display device.

The invention further includes the following items: (1) the composition described above, further including an optically active compound; (2) the composition described above, further including an additive such as an antioxidant, an ultraviolet light absorber and/or an antifoaming agent; (3) an AM device containing the composition described above; (4) a device containing the composition described above and having a mode of TN, ECB, OCB, IPS, FFS, VA or PSA; (5) a transmission-type device containing the composition described above; (6) use of the composition described above as a composition having a nematic phase; and (7) use as an optically active composition prepared by the addition of an optically active compound to the composition described above.

The compound of the invention will be explained. The compound of the invention is represented by formula (1).

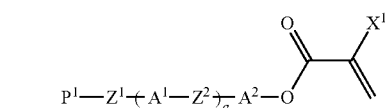
(1)

In formula (1), $A^1$ is independently a single bond, 1,4-cyclohexylene, 1,4-cyclohexenylene, 1,4-phenylene, naphthalene-2,6-diyl, tetrahydropyran-2,5-diyl, 1,3-dioxane-2,5-diyl, pyrimidine-2,5-diyl or pyridine-2,5-diyl, and in these groups at least one hydrogen may be replaced by halogen, alkyl having 1 to 12 carbons or alkyl having 1 to 12 carbons in which at least one hydrogen has been replaced by halogen. Arbitrary two groups represented by two of $A^1$ may be the same or different, when a is 2 or 3.

Desirable $A^1$ is 1,4-cyclohexylene, 1,4-phenylene or naphthalene-2,6-diyl, and in these groups at least one hydrogen may be replaced by fluorine, chlorine, alkyl having 1 to 4 carbons or alkyl having 1 to 4 carbons in which at least one hydrogen has been replaced by fluorine. More desirable $A^1$ is 1,4-phenylene, 2-fluoro-1,4-phenylene, 2,3-difluoro-1,4-phenylene, 2-methyl-1,4-phenylene, 2-trifluoromethyl-1,4-phenylene, 2,3-bis(trifluoromethyl)-1,4-phenylene or naphthalene-2,6-diyl. Further desirable $A^1$ is 1,4-phenylene or 2-fluoro-1,4-phenylene, and especially desirable $A^1$ is 1,4-phenylene.

$A^2$ is 1,4-phenylene or naphthalene-2,6-diyl, and in these groups at least one hydrogen may be replaced by halogen, alkyl having 1 to 12 carbons or alkyl having 1 to 12 carbons in which at least one hydrogen has been replaced by halogen.

Desirable $A^2$ is 1,4-phenylene or naphthalene-2,6-diyl, and in these groups at least one hydrogen may be replaced by fluorine, chlorine, alkyl having 1 to 4 carbons or alkyl having 1 to 4 carbons in which at least one hydrogen has been replaced by fluorine. More desirable $A^2$ is 1,4-phenylene, 2-fluoro-1,4-phenylene, 2,3-difluoro-1,4-phenylene, 2-methyl-1,4-phenylene, 2-trifluoromethyl-1,4-phenylene, 2,3-bis(trifluoromethyl)-1,4-phenylene or naphthalene-2,6-diyl. Further desirable $A^2$ is 1,4-phenylene or 2-fluoro-1,4-phenylene, and especially desirable $A^2$ is 1,4-phenylene.

$Z^1$ is alkylene having 1 to 12 carbons, and in the alkylene at least one —$CH_2$— may be replaced by —O—, —COO—, —OCO—, —OCOO—, —CH=CH— or —C≡C—.

Desirable $Z^1$ is alkylene having 1 to 7 carbons, and in the alkylene at least one —$CH_2$— may be replaced by —O—, —COO—, —OCO—, —OCOO—, —CH=CH— or —C≡C—. More desirable $Z^1$ is —COO—, —OCO—, —OCOO—, —CH=CH—, —CH=CH—O— or —C≡C—. Further desirable $Z^1$ is —OCOO—, —CH=CH— or —CH=CH—O—, and especially desirable $Z^1$ is —CH=CH—O—.

$Z^2$ is independently a single bond or alkylene having 1 to 12 carbons, and in the alkylene at least one —$CH_2$— may be replaced by —O—, —COO—, —OCO—, —OCOO—, —CH=CH— or —C≡C—. At least one of $Z^1$ and $Z^2$ has an unsaturated bond, when all of $A^1$ and $A^2$ are groups in which no hydrogen is replaced. An saturated bond means a group including —CH=CH—, —C≡C— or >C=O. Arbitrary two groups represented by two of $Z^2$ may be the same or different, when a is 2 or 3.

Desirable $Z^2$ is a single bond, —COO—, —OCO—, —CH=CH— or —C≡C—. More desirable $Z^2$ is a single bond, —COO— or —CH=CH—, and especially desirable $Z^2$ is a single bond.

When the bonding group $Z^1$ or $Z^2$ is a group having a double bond such as —CH=CH—, the configuration may be a cis-form or a trans-form.

$X^1$ is hydrogen, fluorine, methyl or trifluoromethyl. Desirable $X^1$ is hydrogen or methyl.

$P^1$ is a polymerizable group. Desirable $P^1$ includes an acryloxy group, a methacryloxy group, an acrylamide group, a methacrylamide group, a vinyl group, a vinyloxy group, a vinylcarbonyl group, an epoxy group, an oxetane group, a 3,4-epoxycyclohexyl group and a maleimide group. More desirable $P^1$ is the group (P-1) to the group (P-3). Especially desirable $P^1$ is the group (P-1) or the group (P-2).

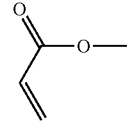

(P-1)

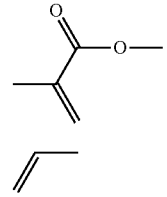

(P-2)

(P-3)

a is an integer from 0 to 3. Desirable a is 0 to 2, and more desirable a is 1 or 2. Especially desirable a is 1.

Desirable examples of the compound (1) include the compound (1-1) and the compound (1-2) described below.

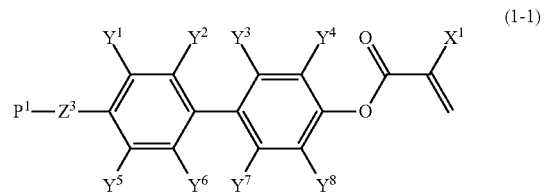

(1-1)

(1-2)

In formula (1-1), $Y^1$ to $Y^8$ are independently hydrogen, fluorine, methyl and trifluoromethyl. Desirable $Y^1$ to $Y^8$ is hydrogen, fluorine or trifluoromethyl. More desirable $Y^1$ to $Y^8$ is hydrogen or fluorine, and especially desirable $Y^1$ to $Y^8$ is hydrogen.

In formula (1-2), $L^1$ to $L^{12}$ are independently hydrogen, fluorine, methyl and trifluoromethyl. Desirable $L^1$ to $L^{12}$ is hydrogen, fluorine or trifluoromethyl. More desirable $L^1$ to $L^{12}$ is hydrogen or fluorine, and especially desirable $L^1$ to $L^{12}$ is hydrogen.

In formula (1-1) or formula (1-2), $Z^3$ is alkylene having 1 to 7 carbons. In the alkylene at least one —$CH_2$— may be replaced by —O—, —COO—, —OCO—, —OCOO—, —CH=CH— or —C≡C—, and when all of $Y^1$ to $Y^8$ are hydrogen or all of $L^1$ to $L^{12}$ are hydrogen, $Z^3$ is alkylene having 1 to 7 carbons in which at least one —$CH_2$— has been replaced by —COO—, —OCO—, —OCOO—, —CH=CH— or —C≡C—.

Desirable $Z^3$ is —COO—, —OCO—, —OCOO—, —CH=CH—, —CH=CH—O— or —C≡C—. More desirable $Z^3$ is —OCOO—, —CH=CH— or —CH=CH—O—, and especially desirable $Z^3$ is —CH=CH—O—.

When $Z^3$ is a group having a double bond such as —CH=CH—, the configuration may be a cis-form or a trans form.

The composition of the invention will be explained. The composition includes at least one of the compound (1) and may include two or more of the compound (1). The compound (1) may be added to a non-polymerizable liquid crystal composition. A desirable composition is a liquid crystal composition that can be used for a liquid crystal display device. The composition of the invention is required to include the compound (1) as a component A. The composition may consist of the component A or the composition may include the component A and other components where their names are not especially shown in the present specification. A liquid crystal composition having a variety of characteristics can be provided by the addition of a component selected from the component B and the component C described below, to the component A.

The component B consisting of at least one compound selected from the group of the compound (2), the compound (3) and the compound (4) is desirable as a component that will be added to the component A. Threshold voltage, the temperature range of a liquid crystal phase, optical anisotropy, dielectric anisotropy, viscosity and so forth can be adjusted by mixing the component C consisting of at least one compound selected from the group of the compound (5), the compound (6) and the compound (7).

The compound (1) may also include isotopes such as $^2$H (deuterium) and $^{13}$C in a larger amount than the amount of the natural abundance, since there are no major differences in physical properties of the compound. The same applies to a component compound that is added to the liquid crystal composition.

In the component B described above, suitable examples of the compound (2) include the compound (2-1) to the compound (2-13), suitable examples of the compound (3) include the compound (3-1) to the compound (3-109), and suitable examples of the compound (4) include the compound (4-1) to the compound (4-55).

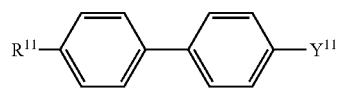
(2-1)

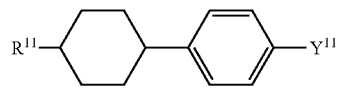
(2-2)

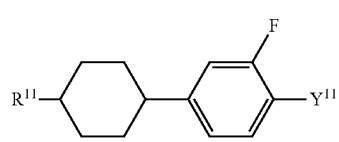
(2-3)

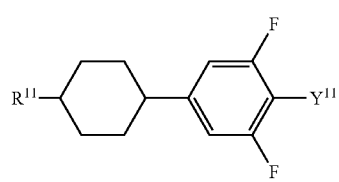
(2-4)

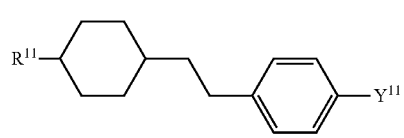
(2-5)

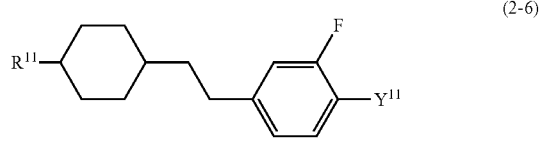
(2-6)

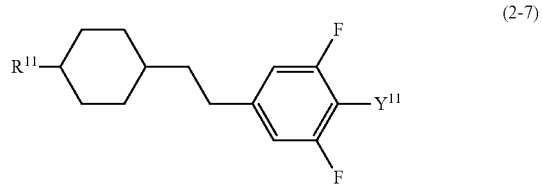
(2-7)

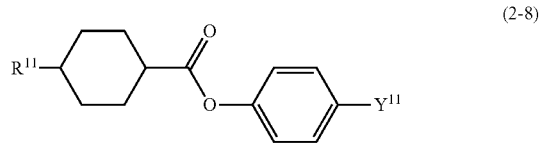
(2-8)

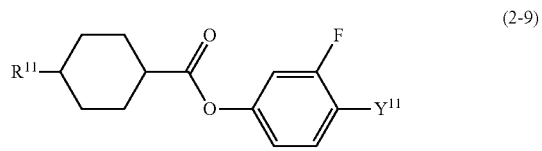
(2-9)

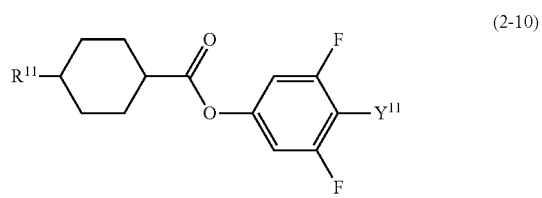
(2-10)

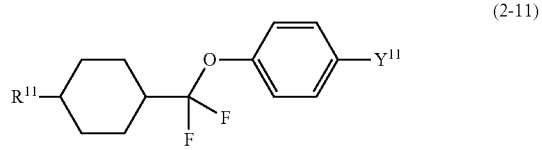
(2-11)

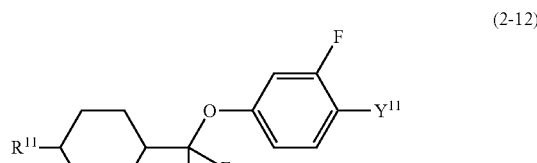
(2-12)

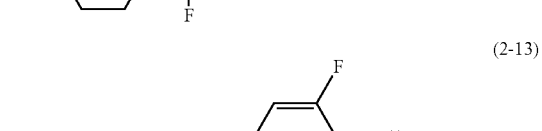
(2-13)

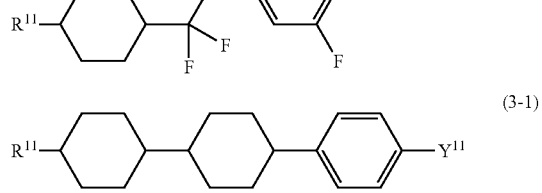
(3-1)

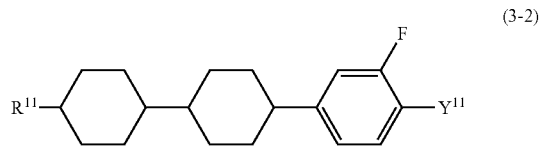
(3-2)

-continued
(3-3)
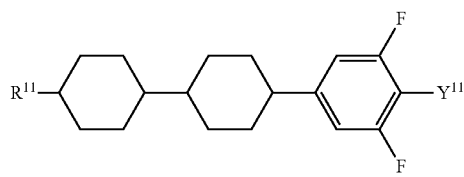
(3-4)
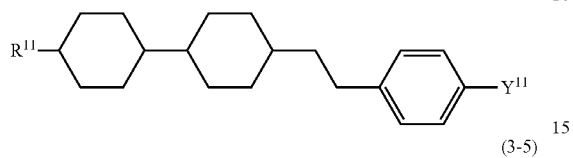
(3-5)
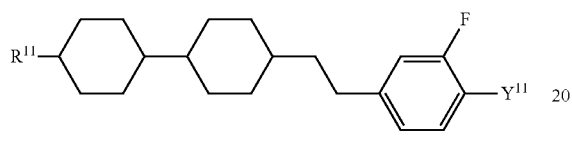
(3-6)
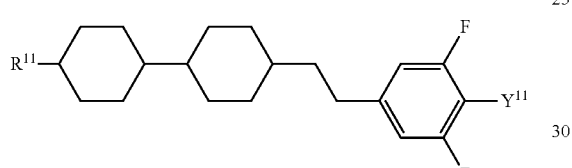
(3-7)
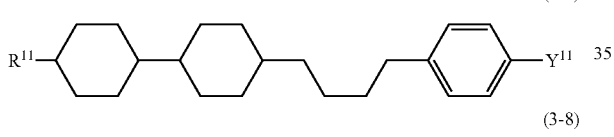
(3-8)
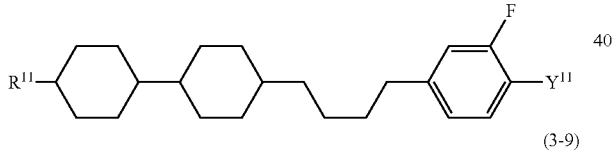
(3-9)
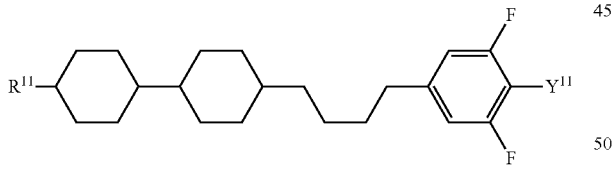
(3-10)
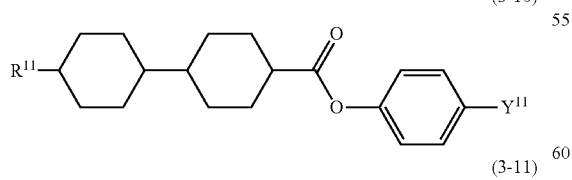
(3-11)
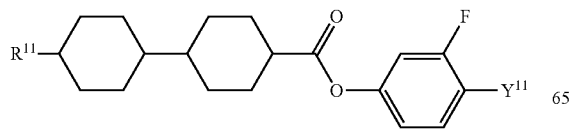
(3-12)
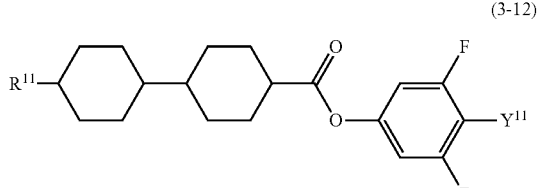
(3-13)
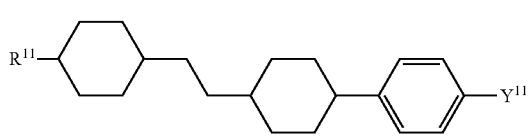
(3-14)
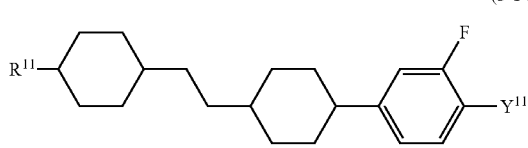
(3-15)
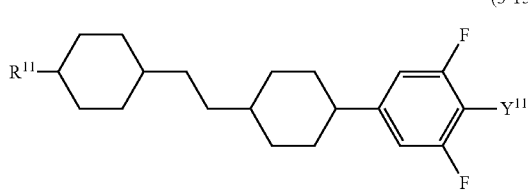
(3-16)
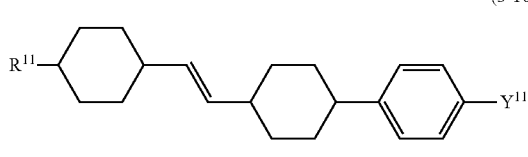
(3-17)
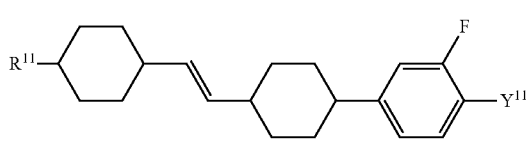
(3-18)
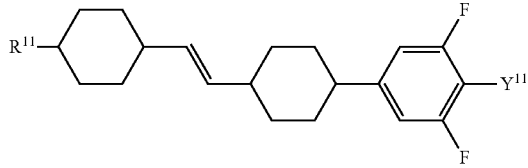
(3-19)
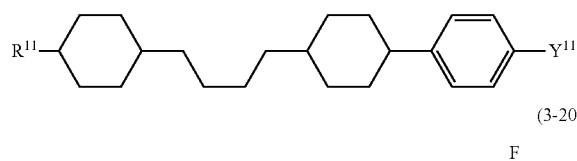
(3-20)
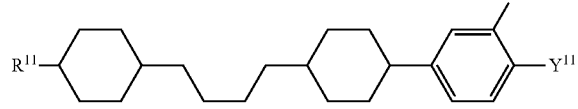

-continued
(3-21) 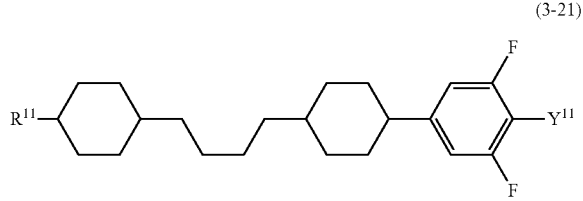
(3-22) 
(3-23) 
(3-24) 
(3-25) 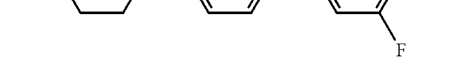
(3-26) 
(3-27) 
(3-28) 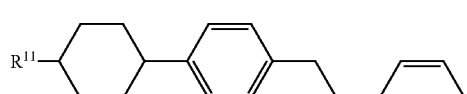
(3-29) 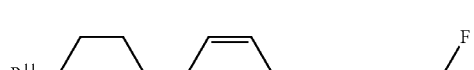
-continued
(3-30) 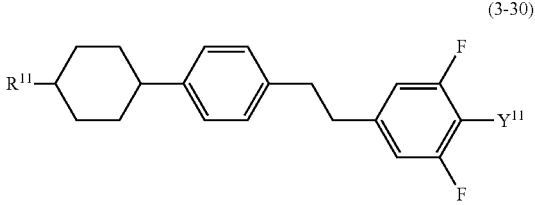
(3-31) 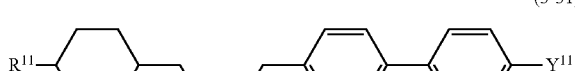
(3-32) 
(3-33) 
(3-34) 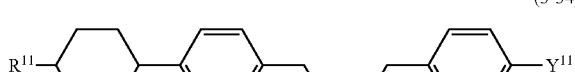
(3-35) 
(3-36) 
(3-37) 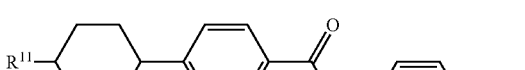
(3-38) 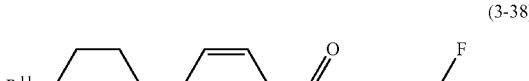

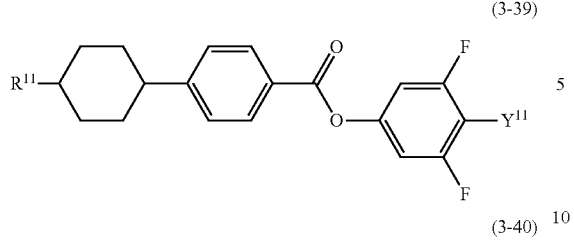
(3-39)
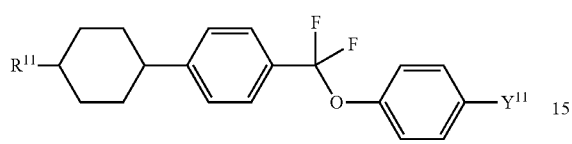
(3-40)
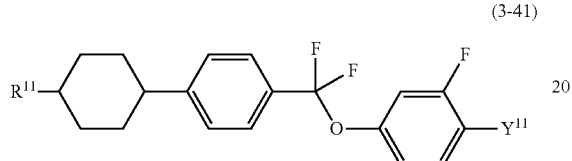
(3-41)
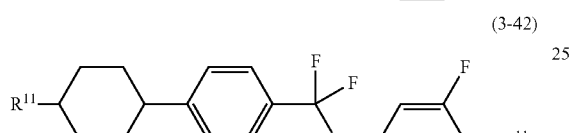
(3-42)
(3-43)
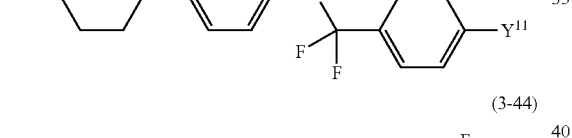
(3-44)
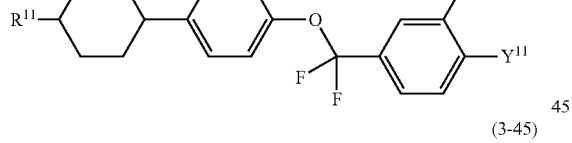
(3-45)
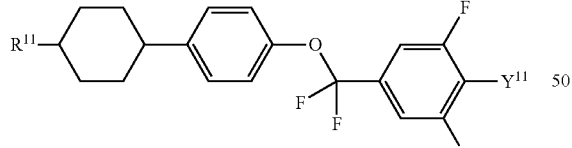
(3-46)
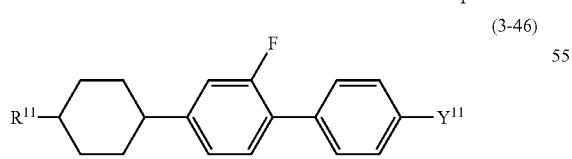
(3-47)
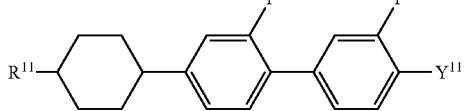
(3-48)
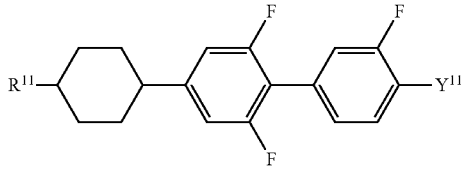
(3-49)
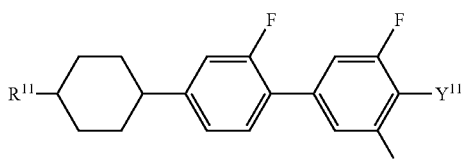
(3-50)
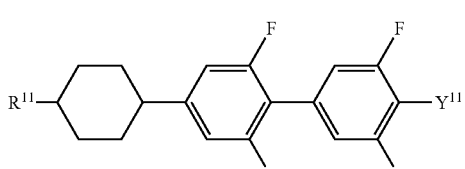
(3-51)
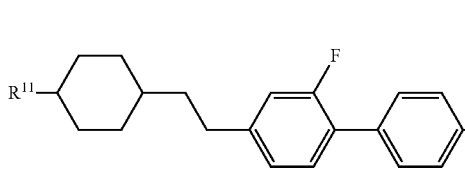
(3-52)
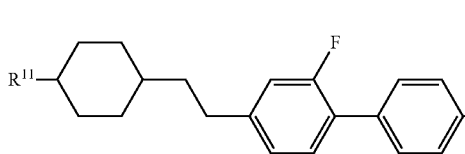
(3-53)
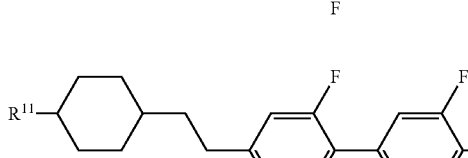
(3-54)
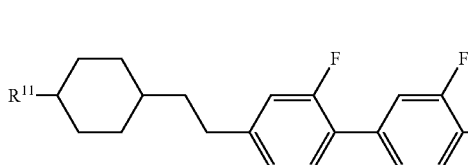
(3-55)
(3-56)

(3-57)
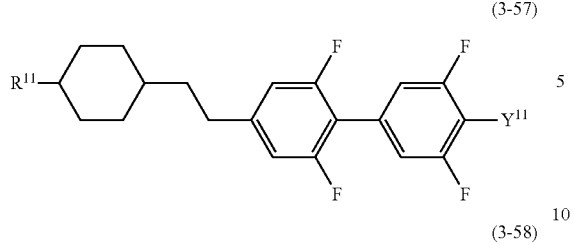
(3-58)
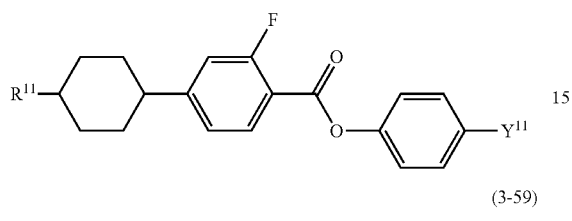
(3-59)
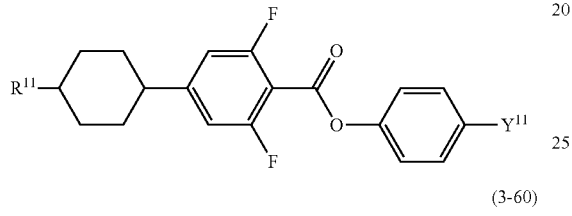
(3-60)
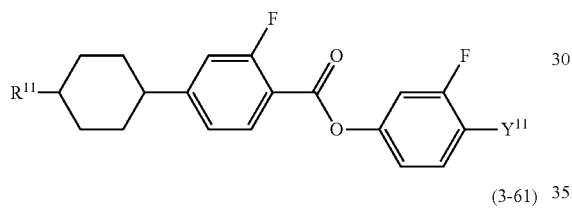
(3-61)
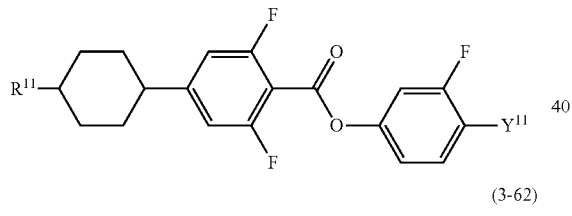
(3-62)
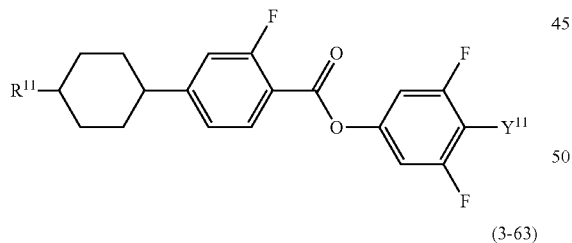
(3-63)
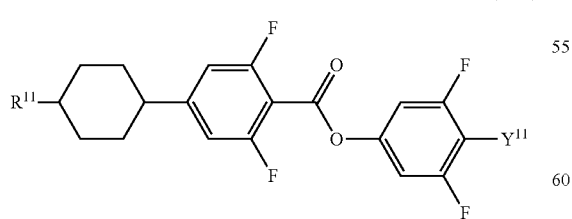
(3-64)
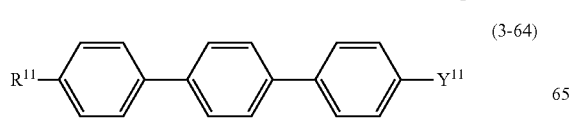
(3-65)
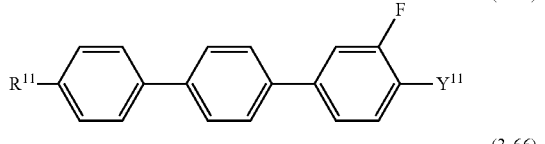
(3-66)
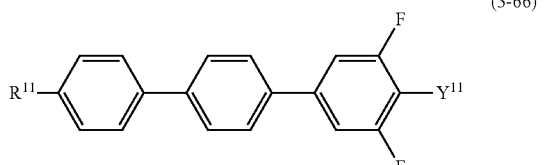
(3-67)
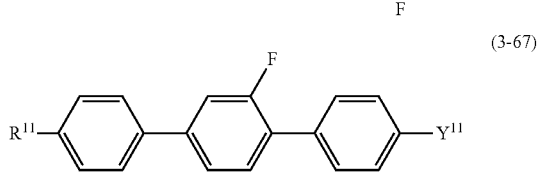
(3-68)
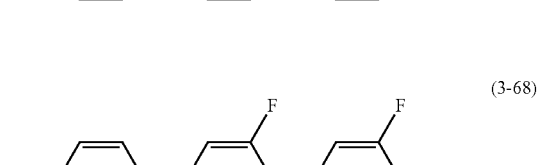
(3-69)
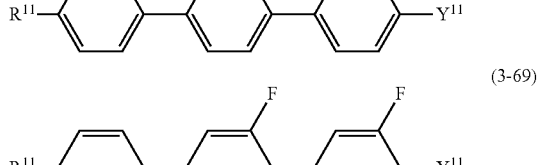
(3-70)
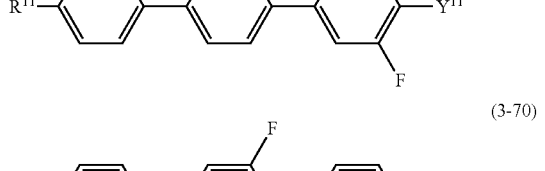
(3-71)
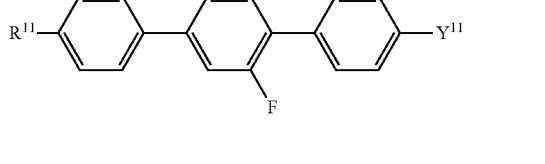
(3-72)
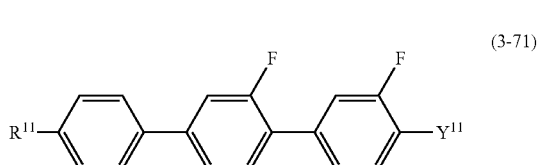
(3-73)
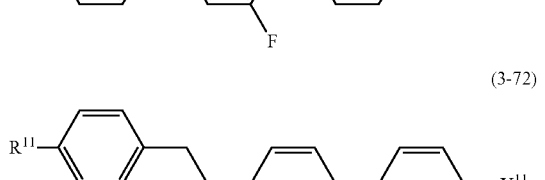

(3-74)
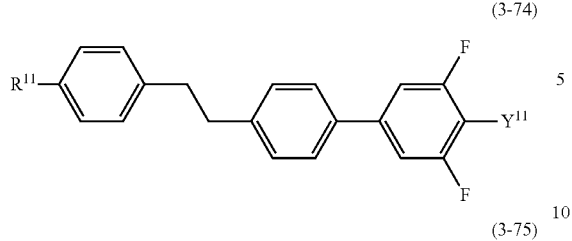
(3-75)
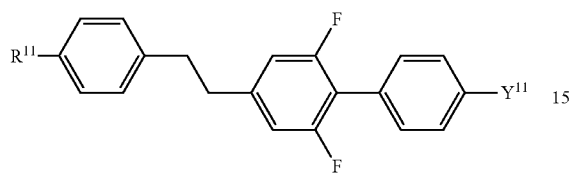
(3-76)
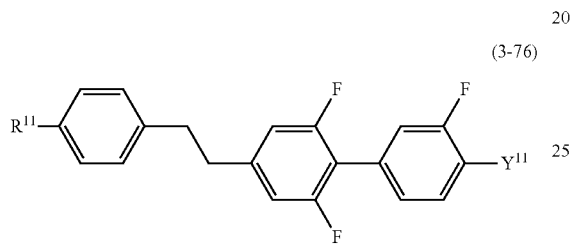
(3-77)
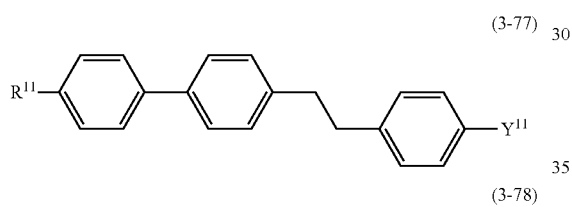
(3-78)
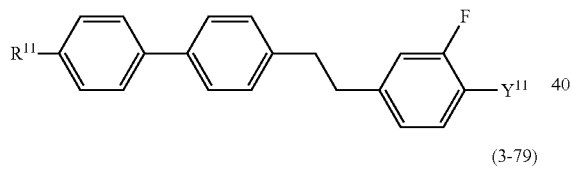
(3-79)
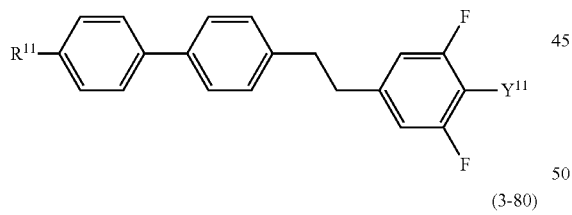
(3-80)
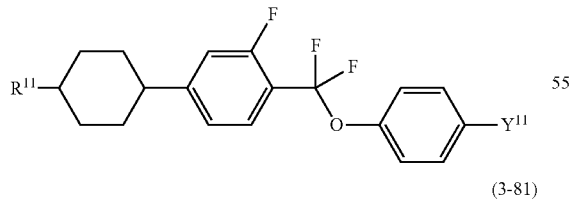
(3-81)
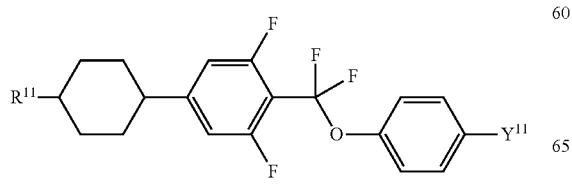
(3-82)
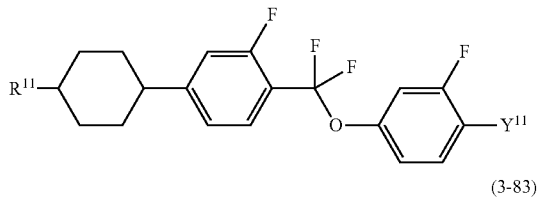
(3-83)
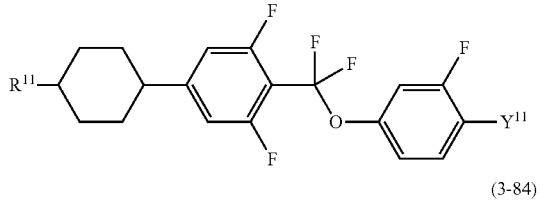
(3-84)
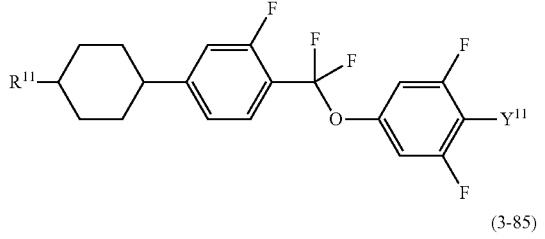
(3-85)
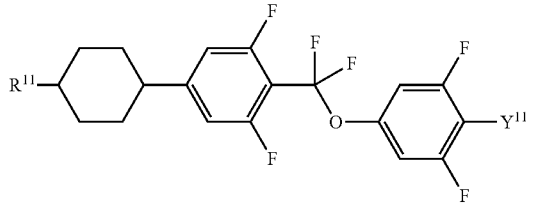
(3-86)
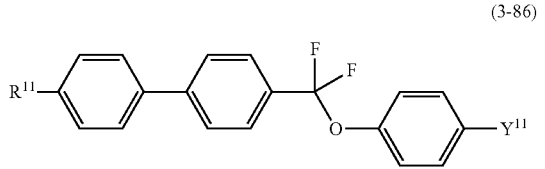
(3-87)
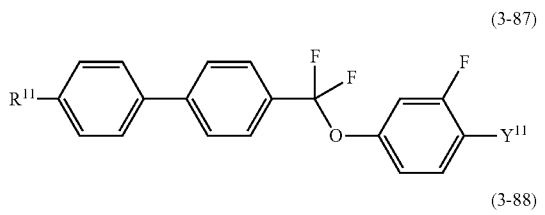
(3-88)
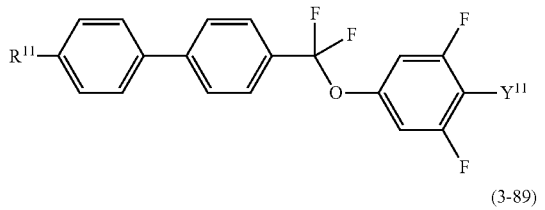
(3-89)
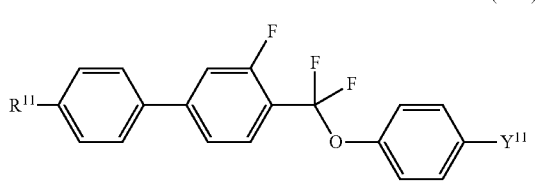

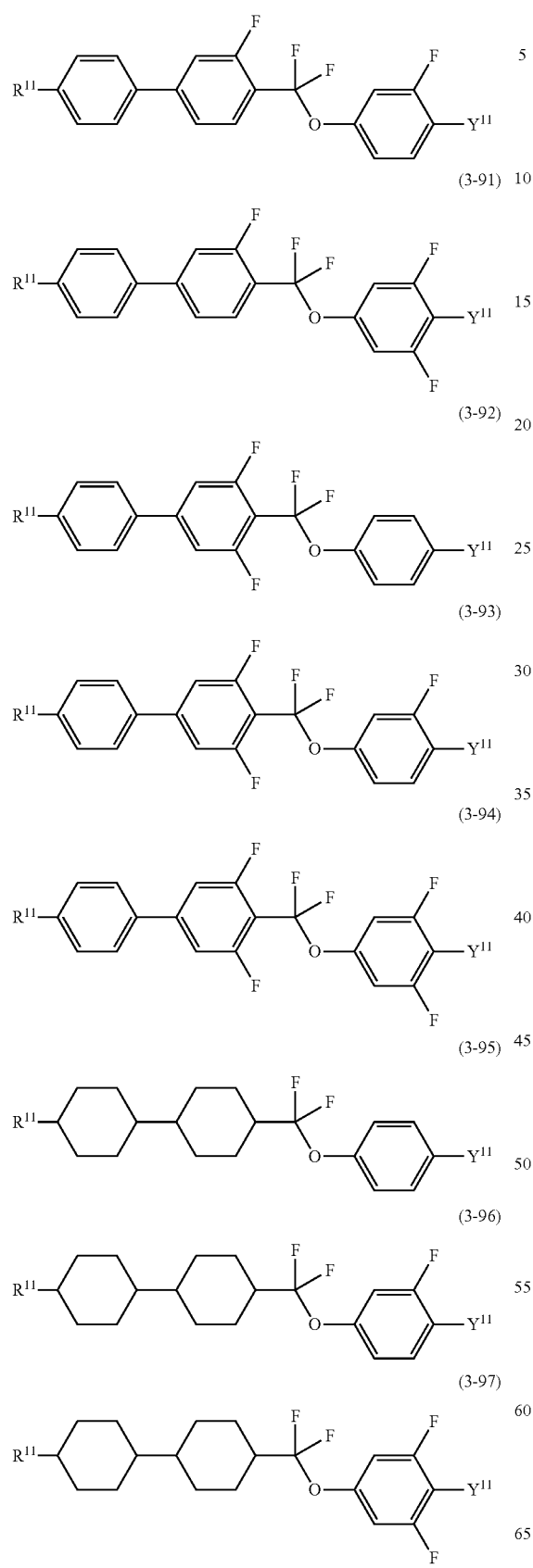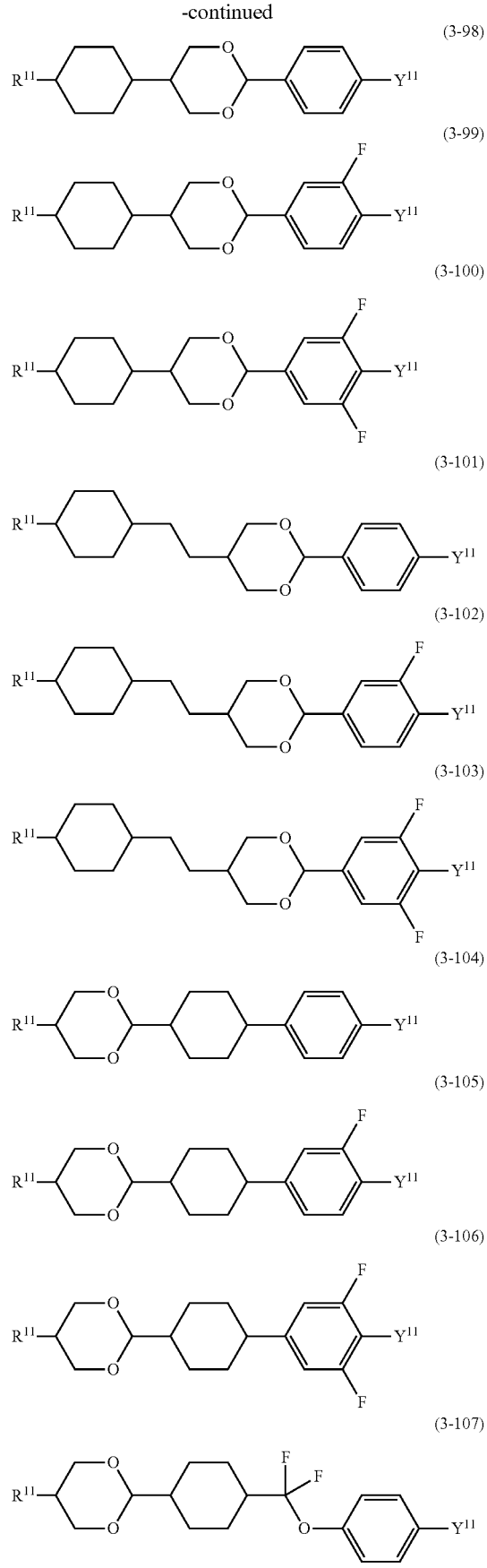

(3-108)
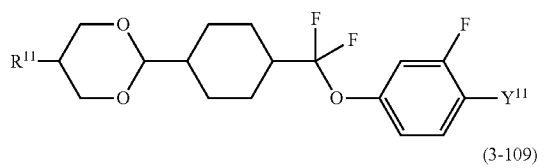
(3-109)
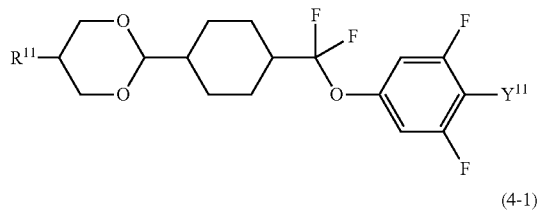
(4-1)
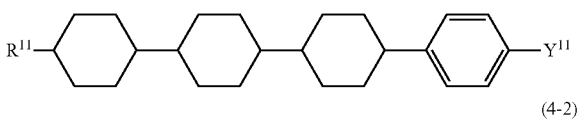
(4-2)
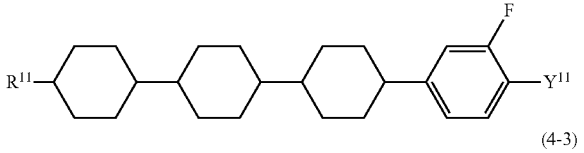
(4-3)
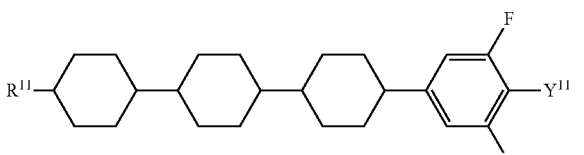
(4-4)
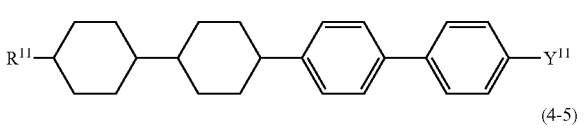
(4-5)
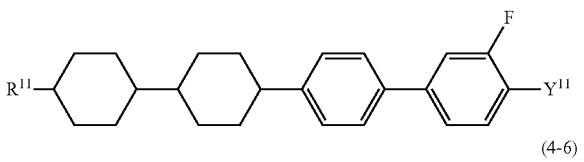
(4-6)
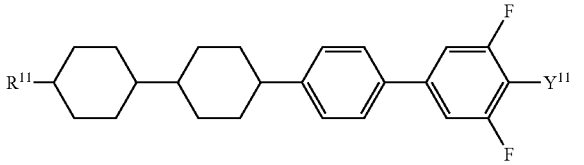
(4-7)
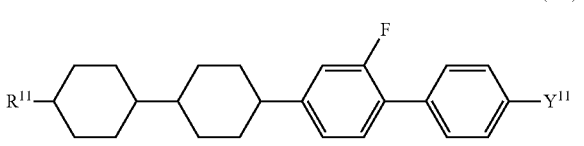
(4-9)
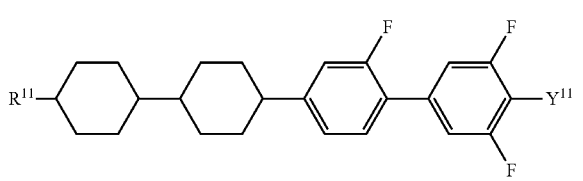
(4-10)
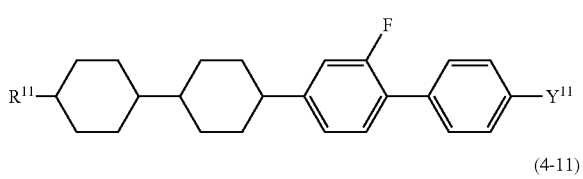
(4-11)
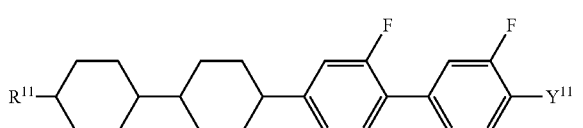
(4-12)
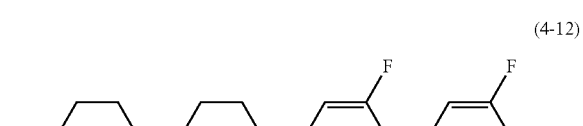
(4-13)
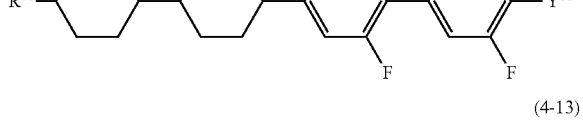
(4-14)
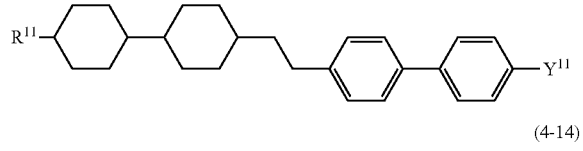
(4-15)
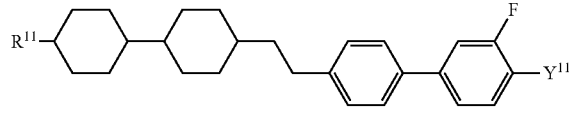
(4-16)
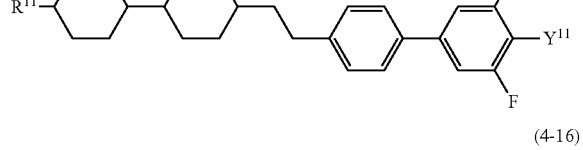
(4-17)
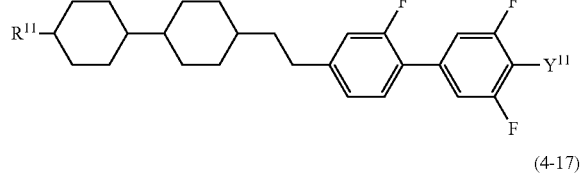

(4-18) 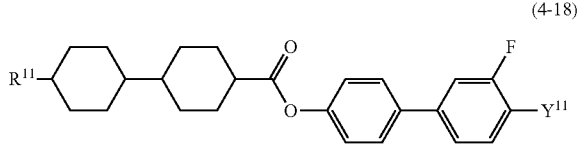
(4-19) 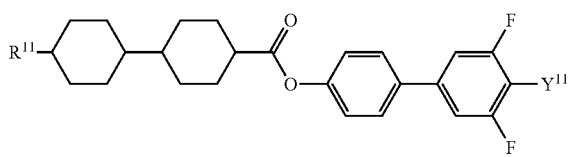
(4-20) 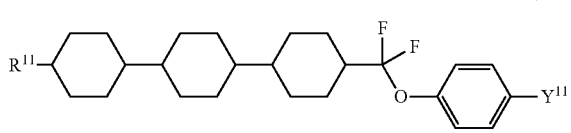
(4-21) 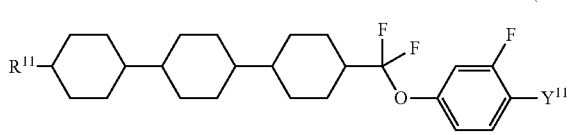
(4-22) 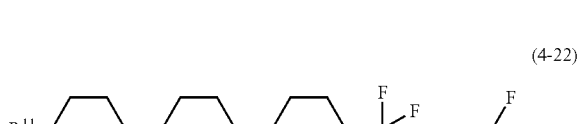
(4-23) 
(4-24) 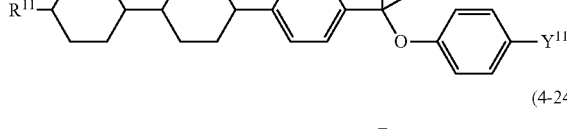
(4-25) 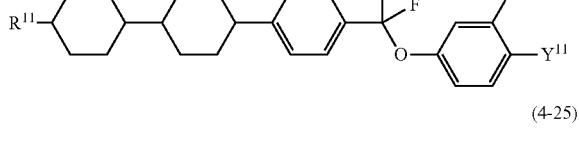
(4-26) 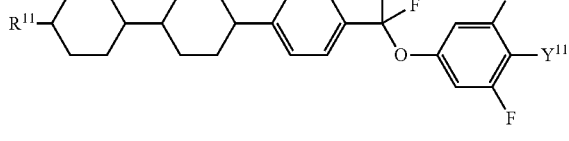
(4-27) 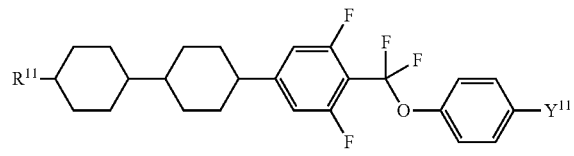
(4-28) 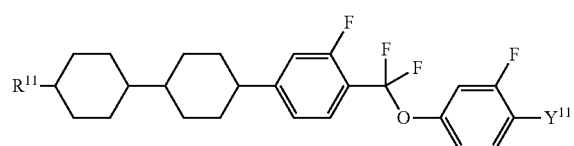
(4-29) 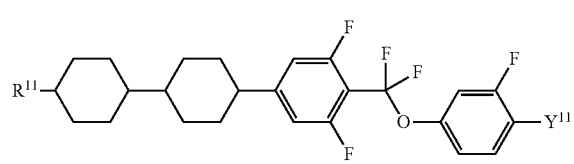
(4-30) 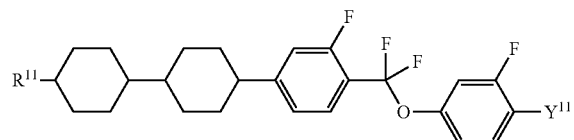
(4-31) 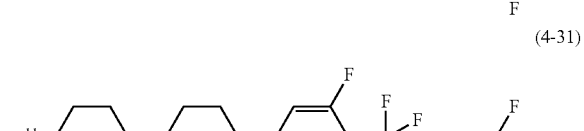
(4-32) 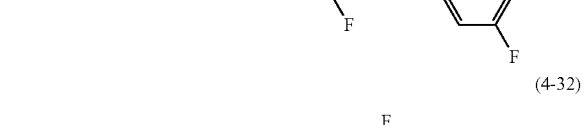
(4-33) 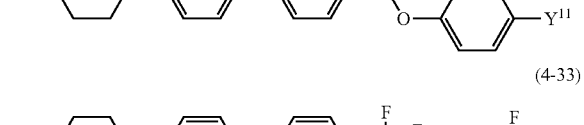
(4-34) 
(4-35) 
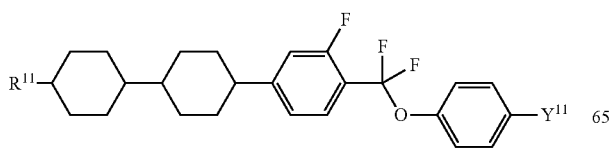
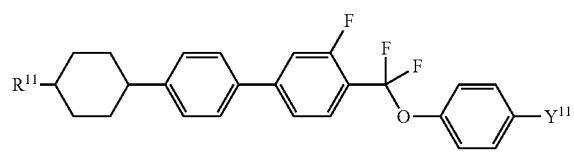

(4-36)
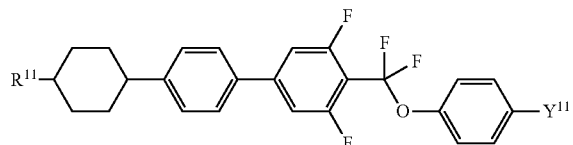
(4-37)
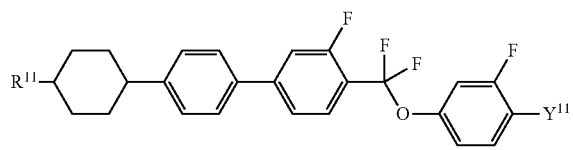
(4-38)
(4-39)
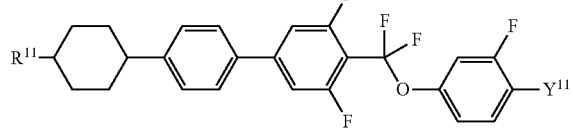
(4-40)
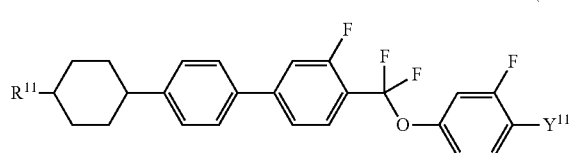
(4-41)
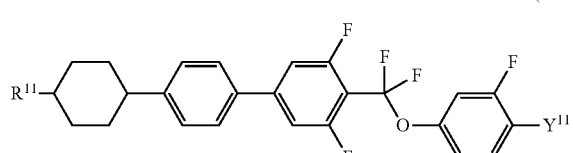
(4-42)
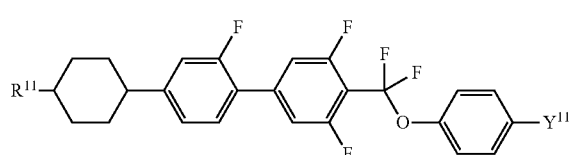
(4-43)
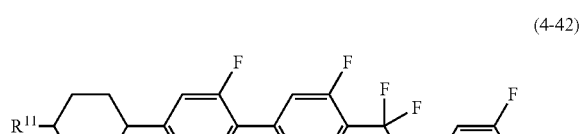
(4-44)
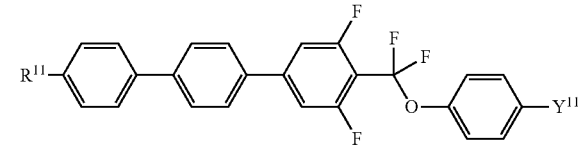
(4-45)
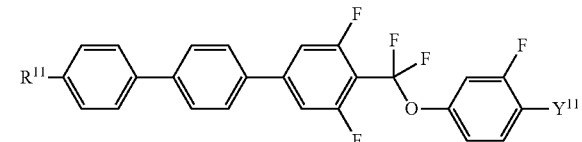
(4-46)
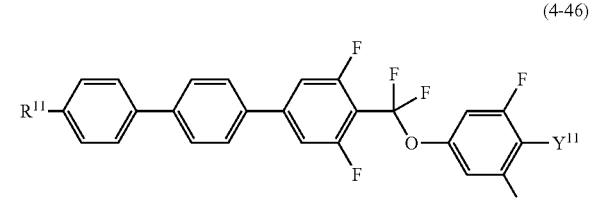
(4-47)
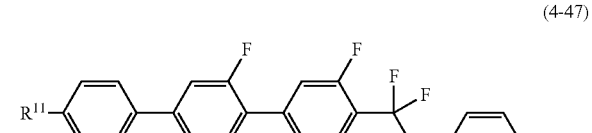
(4-48)
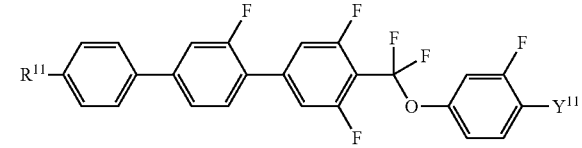
(4-49)
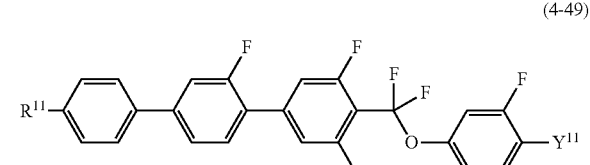
(4-50)
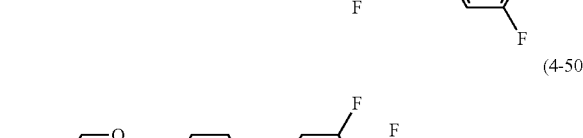
(4-51)
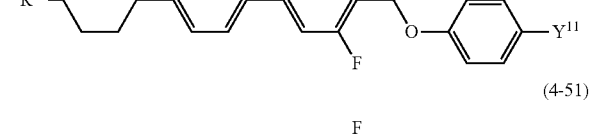

(4-52)
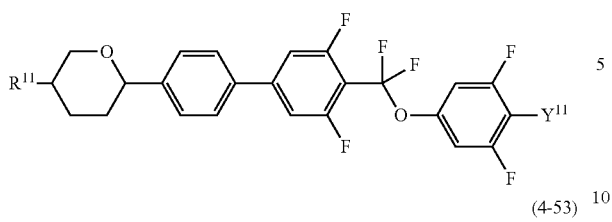

(4-53)
(4-54)
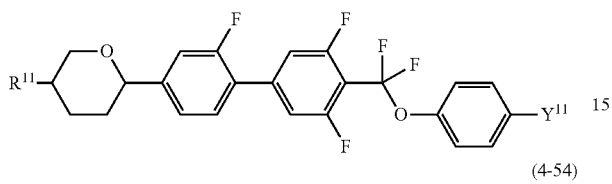
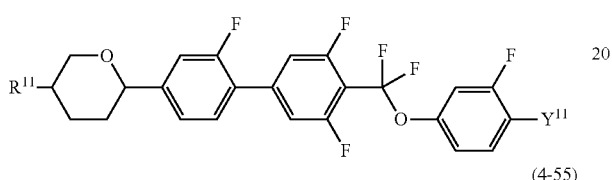

(4-55)
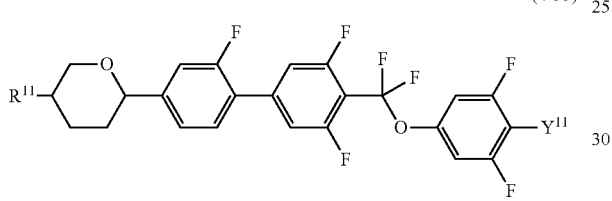

In these compounds, the definitions of $R^{11}$ and $Y^{11}$ are just the same as described previously.

The compound (2) to the compound (4), namely the component B, are used for the preparation of a liquid crystal composition for use in a TFT mode, since the dielectric anisotropy is positive, and the thermal stability and the chemical stability are quite excellent. The content of the component B in the liquid crystal composition is suitably in the range of approximately 1% by weight to approximately 99% by weight, preferably in the range of approximately 10% by weight to approximately 97% by weight, and more preferably in the range of approximately 40% by weight to approximately 95% by weight based on the total weight of the liquid crystal composition. The viscosity can be adjusted by further addition of the compound (5) to the compound (7) (the component C).

Suitable examples of the compound (5), the compound (6) and the compound (7) (the component C) include the compound (5-1) to the compound (5-10), the compound (6-1) to the compound (6-14) and the compound (7-1) to the compound (7-6).

(5-1)
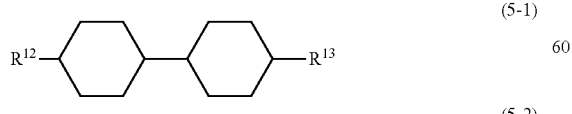

(5-2)
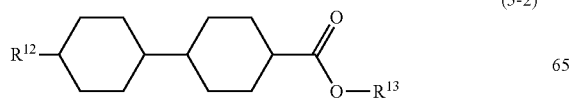

(5-3)
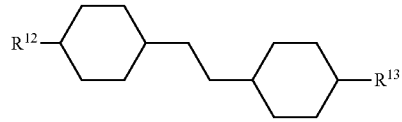

(5-4)
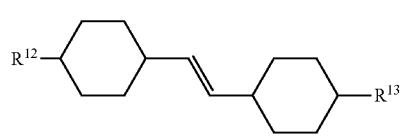

(5-5)
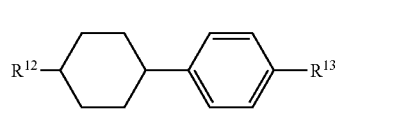

(5-6)
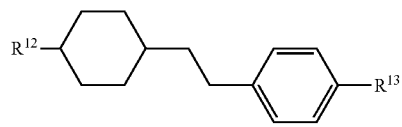

(5-7)
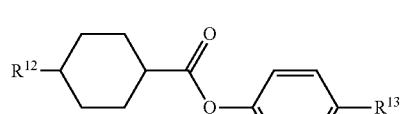

(5-8)
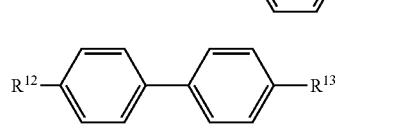

(5-9)
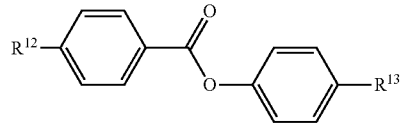

(5-10)
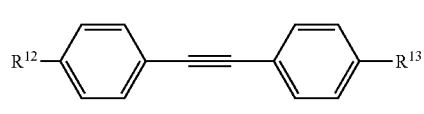

(6-1)
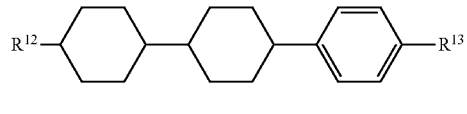

(6-2)
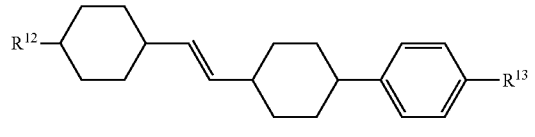

(6-3)

(6-4)
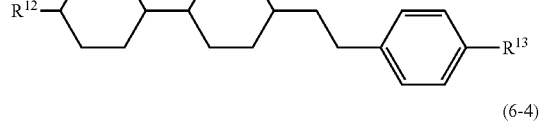

-continued (6-5) 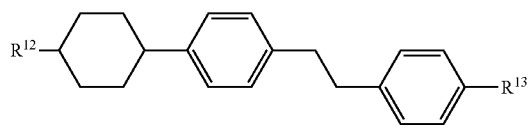

(6-6) 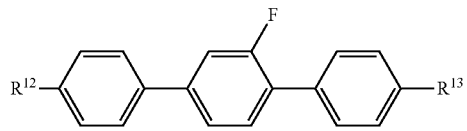

(6-7) 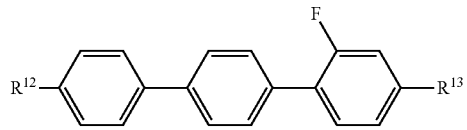

(6-8) 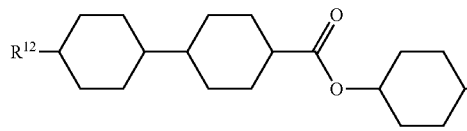

(6-9) 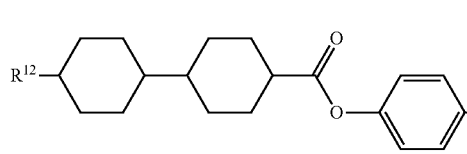

(6-10) 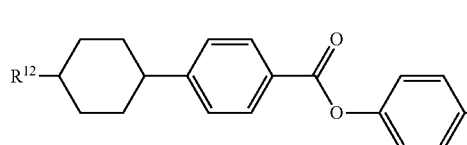

(6-11) 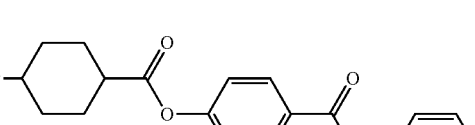

(6-12) 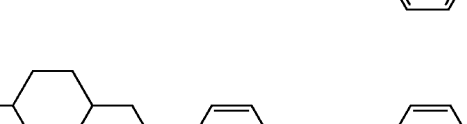

(6-13) 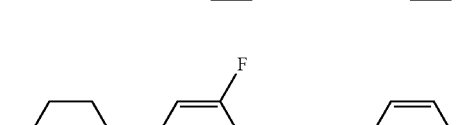

(6-14) 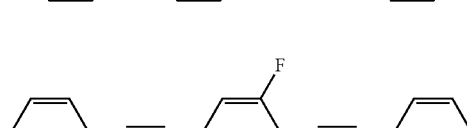

-continued (7-1) 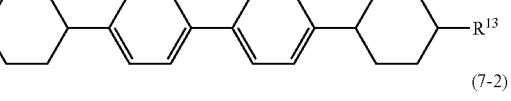

(7-2) 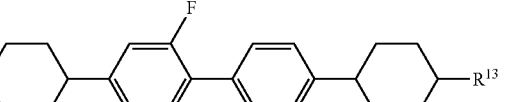

(7-3) 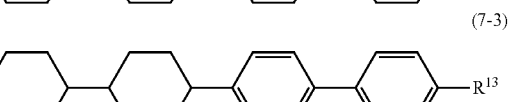

(7-4) 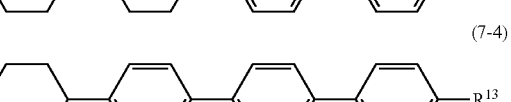

(7-5) 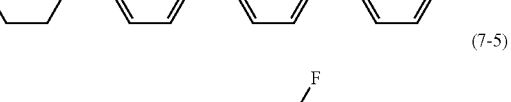

(7-6) 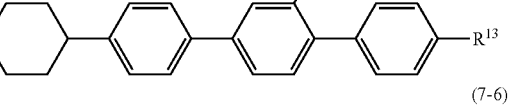

In these compounds, the definitions of $R^{12}$ and $R^{13}$ are just same as described previously.

The compound (5) to the compound (7) (the component C), in which the absolute value of the dielectric anisotropy is small, are close to neutral. The compound (5) is effective mainly in adjusting the viscosity or adjusting the optical anisotropy, and the compound (6) and the compound (7) are effective in increasing the temperature range of a nematic phase that is caused by an increase of the clearing point for instance, or in adjusting the optical anisotropy.

As the content of the component C is increased, the threshold voltage of the liquid crystal composition increases, however, the viscosity decreases. It is desirable that the content should increase as long as the required value of the threshold voltage is satisfied, accordingly. The content of the component C is preferably approximately 30% by weight or more, and more preferably approximately 50% by weight or more based on the total weight of the composition, in the preparation of the liquid crystal composition for use in a TFT mode.

It is desirable that the composition of the invention should include at least one of the compound (1) in the range of approximately 0.05% by weight to approximately 20% by weight. It is more desirable that the composition of the invention should include at least one of the compound (1) in the range of approximately 0.1% by weight to approximately 10% by weight.

The composition of the invention is generally prepared according to known methods such as the mutual dissolution of necessary components at a high temperature, for instance. An additive that is well-known to a person skilled in the art may be added to the composition depending on its intended use. For example, a composition including an optically active compound and a composition to which a dye is added for use in a GH mode can be prepared, those of which will be described below. These kinds of additives are well-known to a person skilled in the art, and are described in the literature.

The liquid crystal composition of the invention may further include one or more optically active compounds. A known chiral dopant can be added as an optically active compound. The chiral dopant is effective in inducing a helical structure in liquid crystals, adjusting a necessary twist angle and thus preventing a reverse twist. Examples of the chiral dopant include the optically active compound (Op-1) to the optically active compound (Op-11) described below.

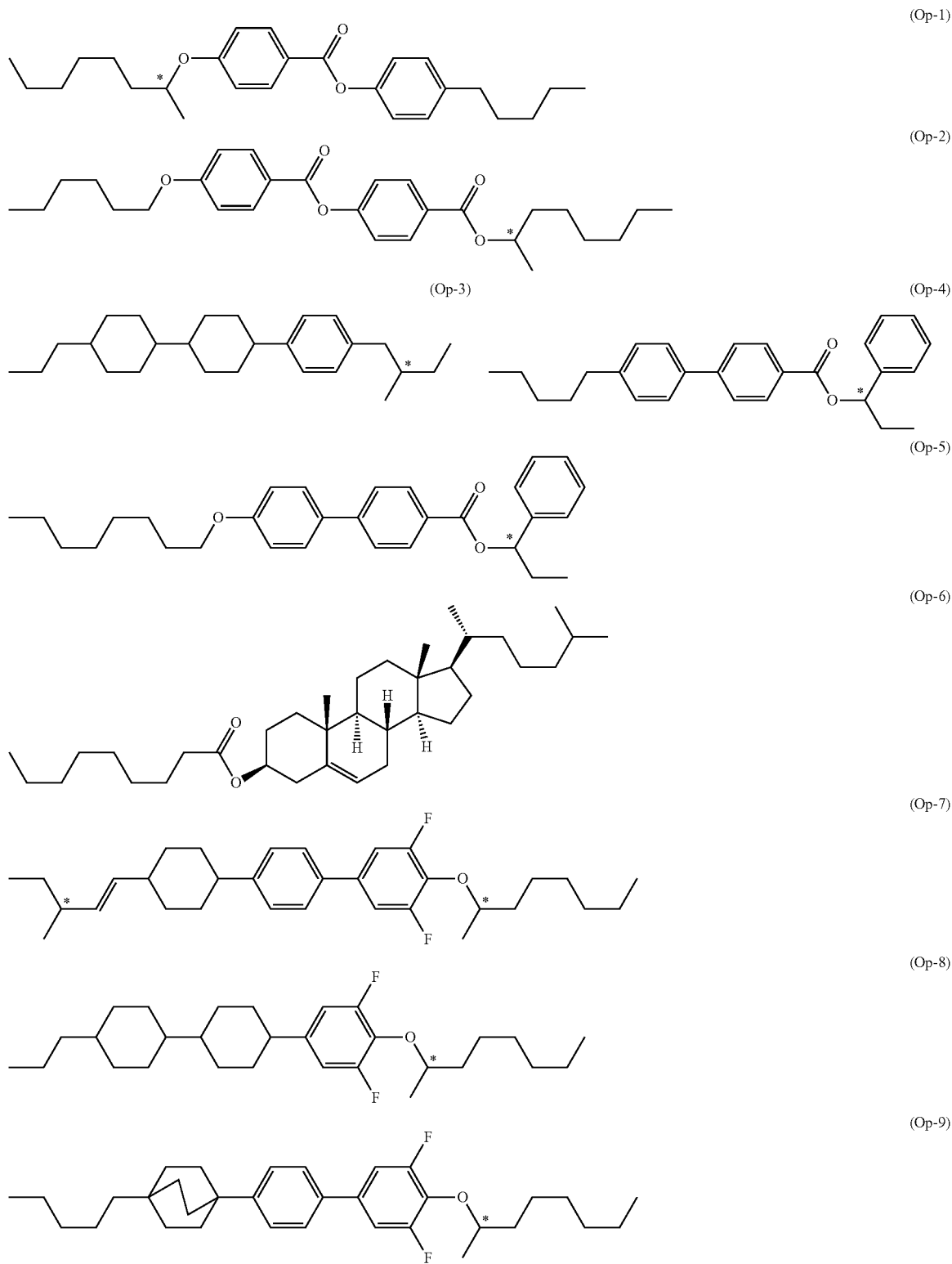

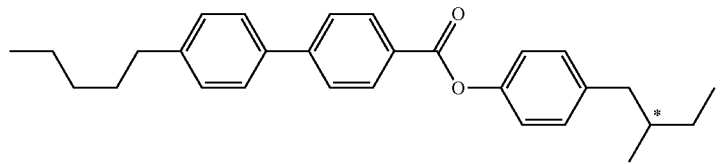

(Op-10)

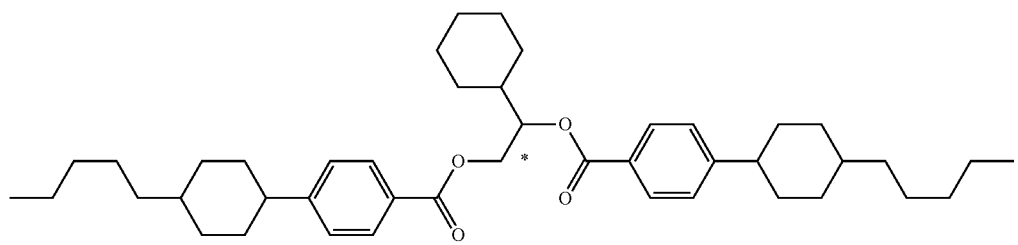

(Op-11)

The composition of the invention can be used for a liquid crystal composition for use in a GH mode by the addition of a dichroic dye such as a merocyanine, stylyl, azo, azomethine, azoxy, quinophthalone, anthraquinone or tetrazine compound.

The composition of the invention can be used for NCAP prepared by micro-encapsulating nematic liquid crystals, and for PDLCD (a polymer-distributed liquid crystal display device) prepared by forming a three-dimensional network polymer in liquid crystals, such as PNLCD (a polymer network liquid crystal display device), and also for an ECB (electrically controlled birefringence) mode or a DS mode.

We safely say that an additive such as a polymerization initiator, an antioxidant, an ultraviolet light absorbent and/or an antifoaming agent can be added to the composition of the invention.

The antioxidant is effective in maintaining a large voltage holding ratio. Desirable examples of the antioxidant include 2,6-di-tert-butyl-4-alkylphenol. The ultraviolet light absorber is effective for preventing a decrease in the maximum temperature of a nematic phase. Desirable examples of the ultraviolet light absorber include a benzophenone derivative, a benzoate derivative and a triazole derivative. A light stabilizer such as an amine having steric hindrance is also desirable.

The compound of the invention is suitable for radical polymerization. The compound can be polymerized more rapidly by the addition of a polymerization initiator or by the optimization of reaction temperature. The polymerization initiator may be added or may not be added.

Examples of a photo-radical polymerization initiator are, in specific trade names, TPO, 1173 and 4265 of Darocure series, and 184, 369, 500, 651, 784, 819, 907, 1300, 1700, 1800, 1850 and 2959 of Irgacure series, at Ciba Specialty Chemicals, and any known photo-radical polymerization initiator can be used.

Additional examples of the photo-radical polymerization initiator are 4-methoxyphenyl-2,4-bis(trichloromethyl)triazine, 2-(4-butoxystyryl)-5-trichloromethyl-1,3,4-oxadiazole, 9-phenylacridine, 9,10-benzphenazine, a mixture of benzophenone/Michler's ketone, a mixture of hexaarylbiimidazole/mercaptobenzimidazole, 1-(4-isopropylphenyl)-2-hydroxy-2-methylpropan-1-one, benzyldimethylketal, 2-methyl-1-[4-(methylthio)phenyl]-2-morphorinopropan-1-one, a mixture of 2,4-diethylxanthone/methyl p-dimethylaminobenzoate and a mixture of benzophenone/methyltriethanolamine, and any known photo-radical polymerization initiator can be used.

The polymer of the invention can be produced by the polymerization of the compound (1) or a composition including the compound (1). Homopolymer can be obtained by the polymerization of only one of the compound (1). Copolymer can be obtained by the polymerization of a composition including a plurality of polymerizable compounds. When a composition, where the compound (1) is added to a non-polymerizable liquid crystal composition, is polymerized, the homopolymer of the compound (1) is included in a non-polymerizable liquid crystal composition, and this composition is also expressed as a polymer.

The polymerization can be carried out by the irradiation of energy (electromagnetic waves). Such electromagnetic waves include ultraviolet light, infrared light, visible light, X-rays and γ-rays. High energy particles such as ion or electron may also be irradiated.

The orientation of the compound (1) or its composition can be fixed by means of irradiation with electromagnetic waves. A desirable range of the wavelength of electromagnetic waves is 150 nm to 500 nm. A more desirable range is 50 nm to 450 nm, and an especially desirable range is 300 nm to 400 nm. Irradiation temperature is temperature where the compound (1) or its composition keeps a liquid crystal state, and is preferably 100° C. or less to prevent thermal polymerization.

The compound (1) is polymerized or cross-linked by the polymerization of a liquid crystal composition located between the substrates of a liquid crystal display device. The compound (1) may be polymerized under the conditions of an applied voltage or magnetic field. A desirable method for polymerization is, for example, thermal polymerization or photo-polymerization, and preferably photo-polymerization. A polymerization initiator can be added if necessary. The polymerization conditions and suitable kinds of polymerization initiator are known to a person skilled in the art, and are described in the literature.

The compound (1) is superior in view of rapid reaction even without the polymerization initiator. Accordingly, a poor display caused by the photoinitiator remained or by its decomposition products can be decreased, and a long service life of the product can be attained. The polymerizable compound of the invention can be used alone or by mixing with other polymerizable compound. The polymerizable compound that can be mixed with includes a commercially available monomer or a known monomer, such as a known monofunctional or polyfunctional liquid crystal monomer which is suitable to a liquid crystal display device described, for example, in JP 2004-123829 A.

The liquid crystal display device of the invention has two substrates equipped with transparent electrodes and with alignment films for orienting liquid crystal molecules, for example. A liquid crystal composition including a polymerizable compound is arranged between these substrates. The device is prepared by the polymerization of the polymerizable compound between these substrates. The polymerization may be performed under the conditions of an applied voltage.

The method for synthesizing the compound (1) and a component compound included in the composition will be explained. These compounds can be prepared by a combination of methods in synthetic organic chemistry. Methods of introducing objective terminal groups, rings and bonding groups into starting materials are described in books such as "Houben-Wyle, Methoden der Organische Chemie" (Georg-Thieme Verlag, Stuttgart), "Organic Syntheses" (John Wily & Sons, Inc.), "Organic Reactions" (John Wily & Sons Inc.), "Comprehensive Organic Synthesis" (Pergamon Press), and "Shin Jikken Kagaku Kouza" (New Experimental Chemistry Course, in English; Maruzen Co., Ltd., Japan).

The formation of the bonding group $Z^1$ to the bonding group $Z^3$ will be explained in item (I) to item (IX). In these schemes, $MSG^1$ (or $MSG^2$) is a monovalent organic group having at least one ring. Monovalent organic groups represented by a plurality of the $MSG^1$ (or $MSG^2$) may be the same or different. The compound (1A) to the compound (1L) correspond to the compound (1).

(I) Formation of a Single Bond

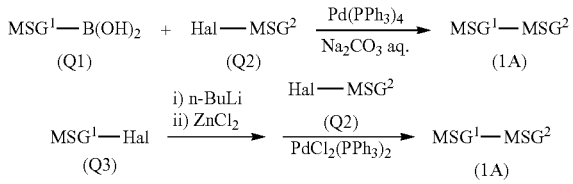

The compound (1A) is prepared by the reaction of the arylboronic acid (Q1) with the compound (Q2) prepared by known methods in the presence of a catalyst such as tetrakis(triphenylphosphine) palladium in an aqueous solution of a carbonate. This compound (1A) can also be prepared by the reaction of the compound (Q3) prepared by known methods with n-butyllithium, and then with zinc chloride, and then by the reaction with the compound (Q2) in the presence of a catalyst such as dichlorobis(triphenylphosphine)palladium.

(II) Formation of —CH=CH—

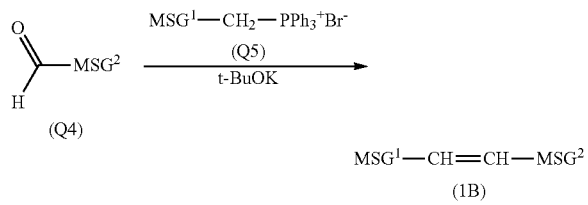

The compound (1B) is prepared by the reaction of the aldehyde (Q4) with phosphine ylide, which is generated from the phosphonium salt (Q5) prepared by known methods by the action of a base such as potassium t-butoxide.

(III) Formation of —(CH$_2$)$_2$—

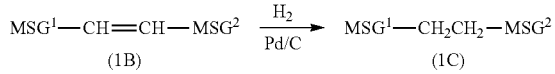

The compound (10) is prepared by hydrogenation of the compound (1B) in the presence of a catalyst such as palladium-carbon.

(IV) Formation of —(CH$_2$)$_4$—

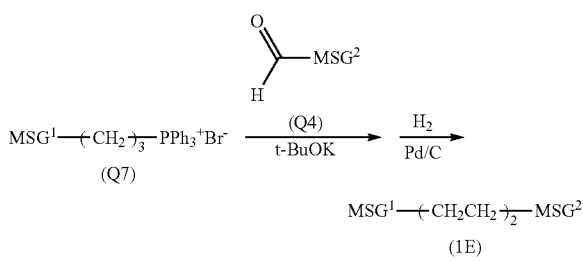

The compound having —(CH$_2$)$_2$—CH=CH— is obtained by the use of the phosphonium salt (Q7) instead of the phosphonium salt (Q5) according to the method of item (II). The compound (1E) is prepared by the hydrogenation of the compound.

(V) Formation of —CH$_2$O— or —OCH$_2$—

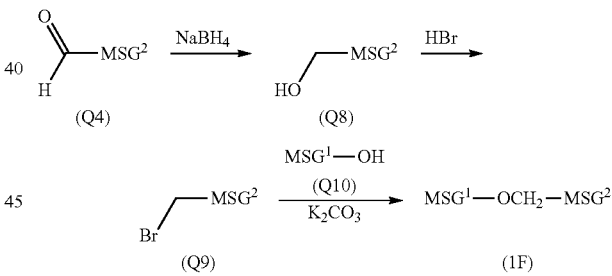

The compound (Q4) is reduced with a reducing agent such as sodium borohydride to give the compound (Q8). Bromination of this compound with hydrobromic acid or the like gives the compound (Q9). The compound (1F) is prepared by the reaction of the compound (Q9) with the compound (Q10) in the presence of potassium carbonate or the like. The compound having —CH$_2$O— can also be prepared by this method.

(VI) Formation of —COO— and —OCO—

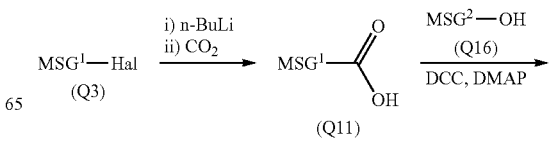

-continued

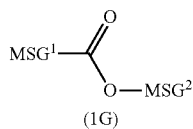

The carboxylic acid (Q11) is obtained by the reaction of the compound (Q3) with n-butyllithium, and then with carbon dioxide. The compound (1G) having —COO— is prepared by the condensation of the compound (Q11) and the phenol (Q16) in the presence of DCC (1,3-dicyclohexylcarbodiimide) and DMAP (4-dimethylaminopyridine). The compound having —OCO— can also prepared by this method.

(VII) Formation of —C≡C—

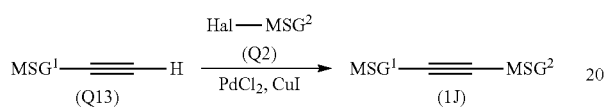

The compound (1J) is prepared by the reaction of the compound (Q13) with the compound (Q2) in the presence of a catalyst of dichloropalladium and copper halide.

(VIII) Formation of —C≡C—COO—

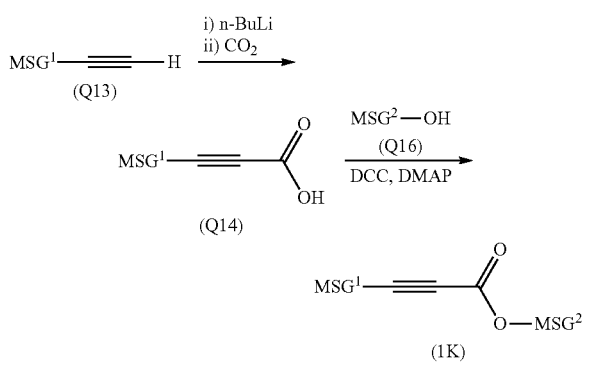

The compound (Q13) is lithiated with n-butyllithium, and then is reacted with carbon dioxide to give the carboxylic acid (Q14). The compound (1K) having —C≡C—COO— is prepared by the condensation of the carboxylic acid (Q14) and the phenol (Q16) in the presence of DCC and DMAP. The compound having —OCO—C≡C— can also prepared by this method.

(IX) Formation of —C≡C—CH=CH— and —CH=CH—C≡C—

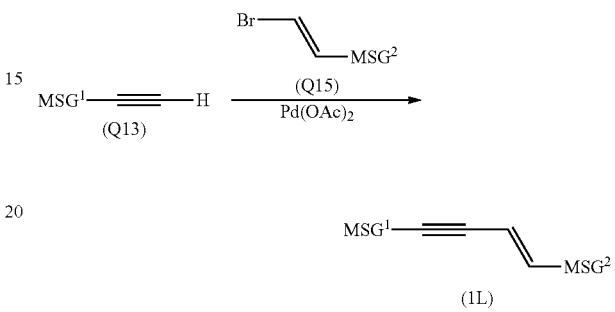

The compound (1L) having —C≡C—CH=CH— can be prepared by the cross-coupling reaction of the compound (Q13) with the vinyl bromide (Q15). The cis-isomer (1L) is formed if the cis-isomer of the compound (Q15) is used.

The polymerizable group (P-1) or group (P-2) can be introduced by the action of the acid chloride (or the acid anhydride) of acrylic acid or methacrylic acid on an organic group having a hydroxyl group. The polymerizable group (P-3) can be introduced by the Grignard reaction of an organic group having halogen with vinly bromide. The composition is prepared from a compound thus obtained by known methods For example, the component compounds are mixed and dissolved in each other by heating.

The compound (a-1) to the compound (a-292) are prepared based on the methods described above.

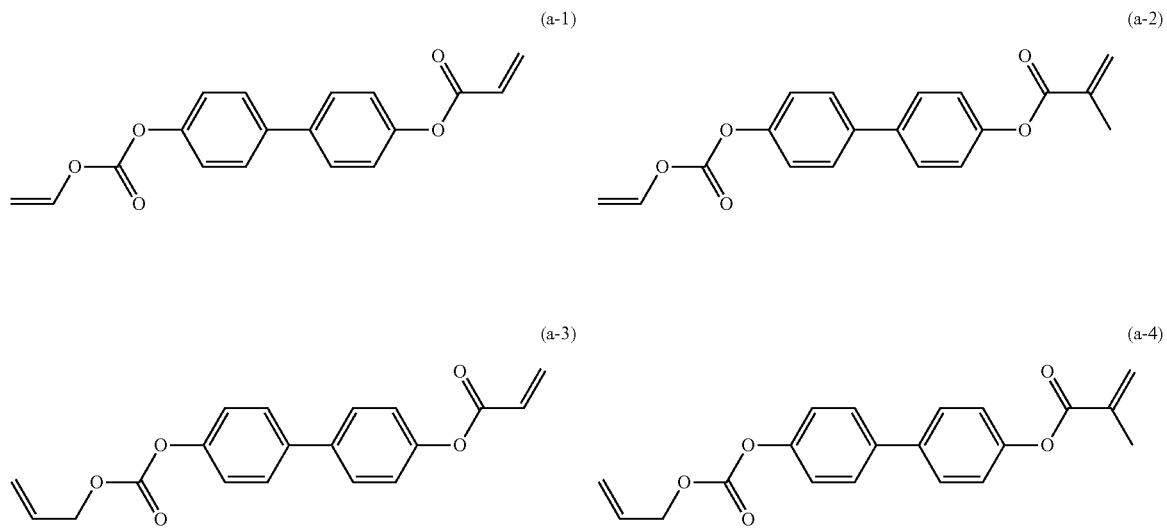

-continued
(a-5)
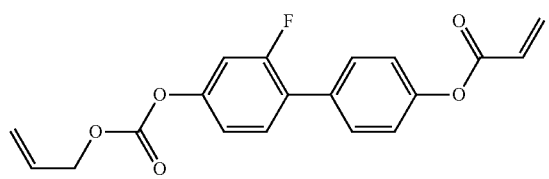
(a-6)
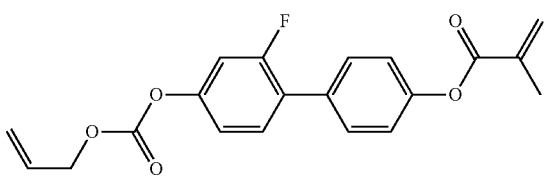
(a-7)
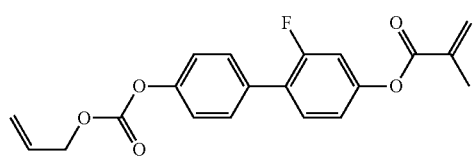
(a-8)
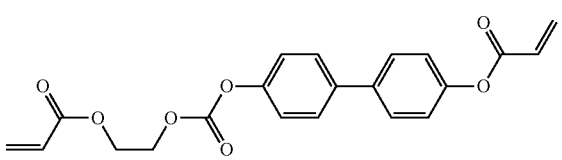
(a-9)
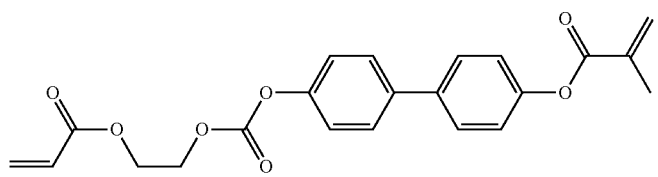
(a-10)
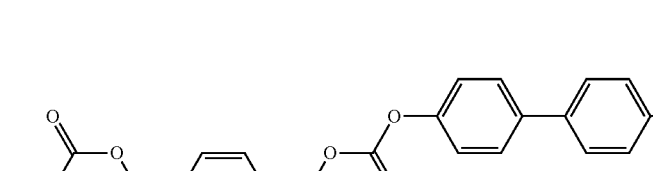
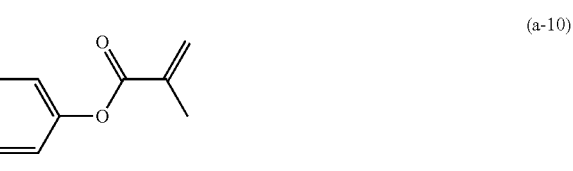
(a-11)
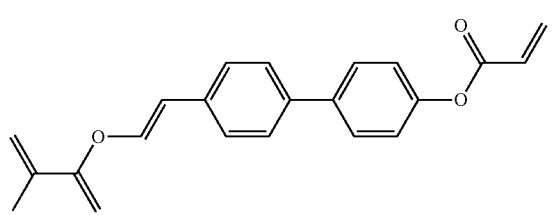
(a-12)
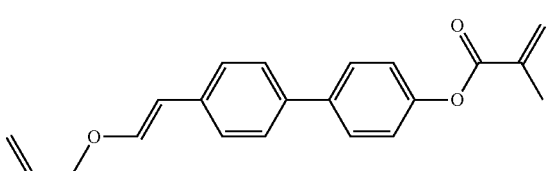
(a-13)
(a-14)
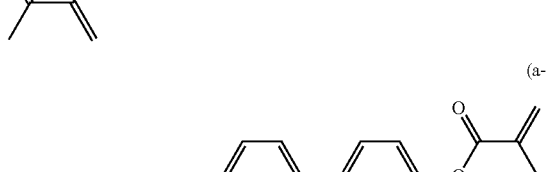
(a-15)
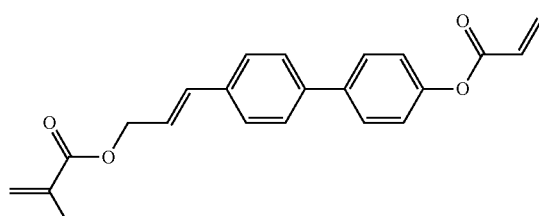
(a-16)
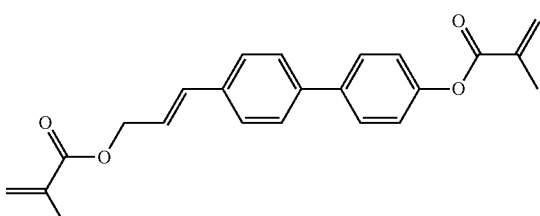
(a-17)
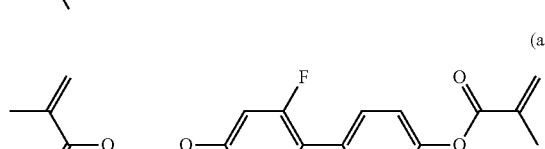
(a-18)
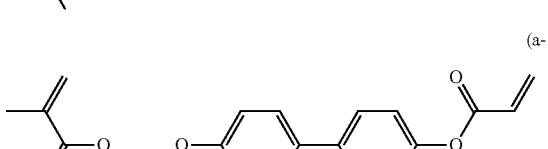
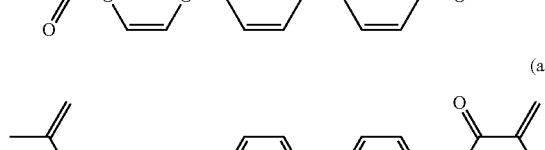
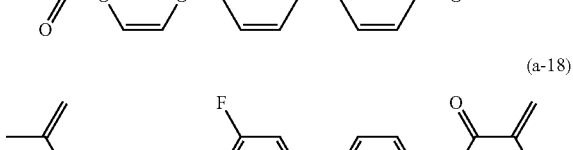
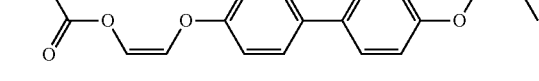
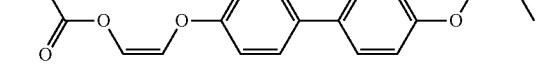

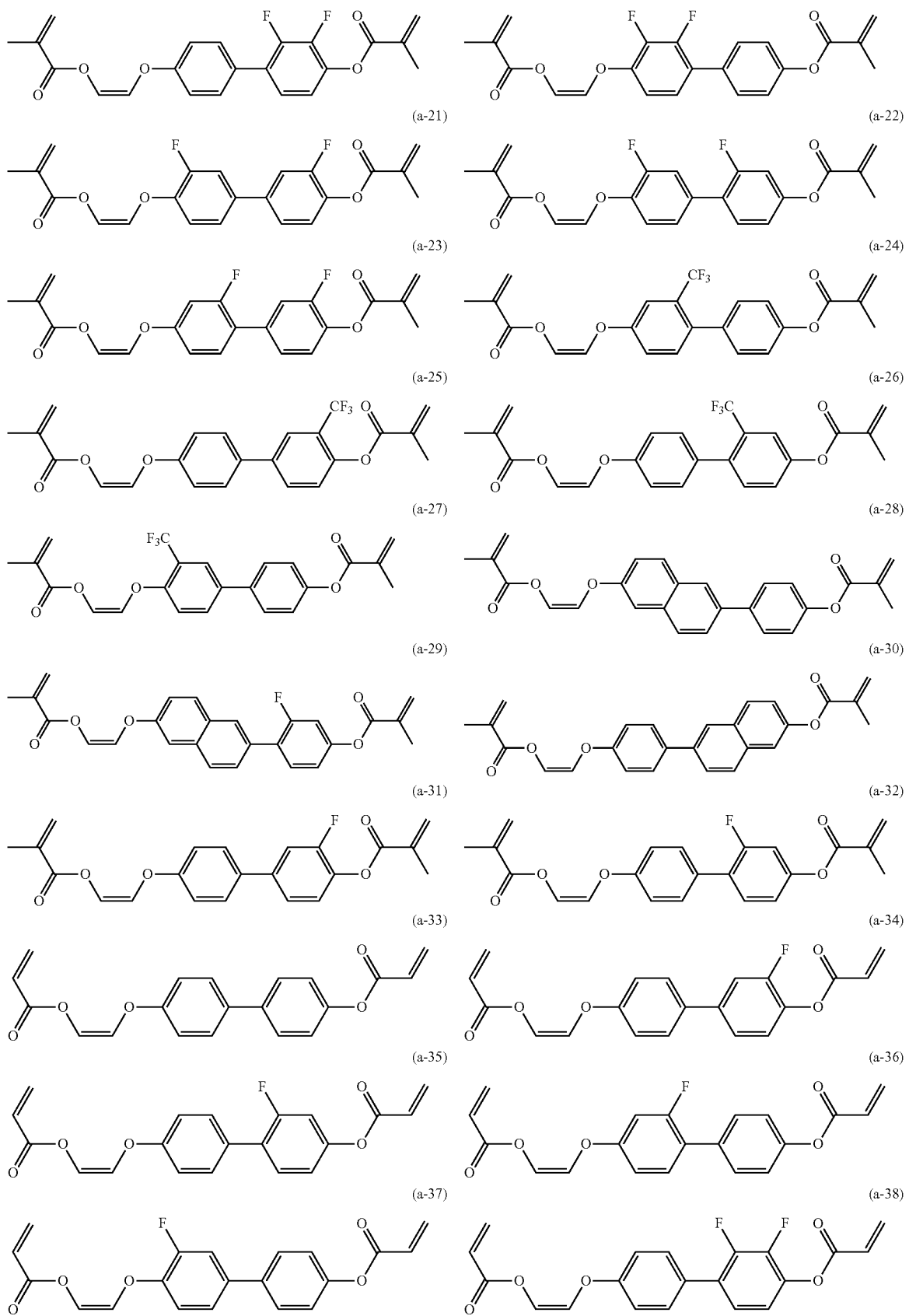

-continued
(a-39)
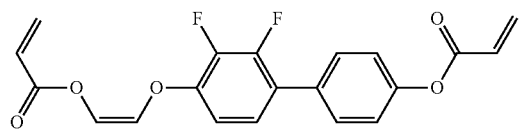
(a-40)
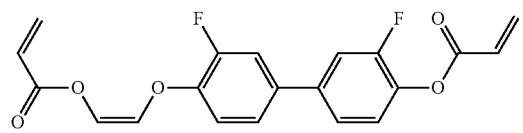
(a-41)
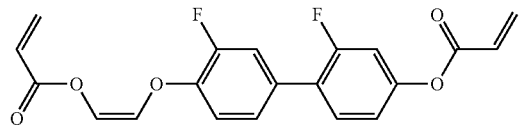
(a-42)
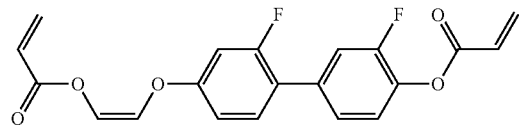
(a-43)
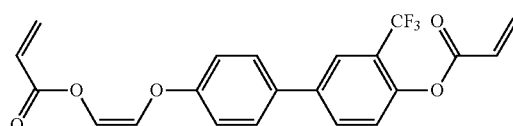
(a-44)
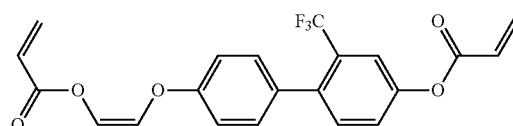
(a-45)
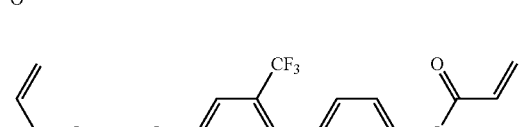
(a-46)
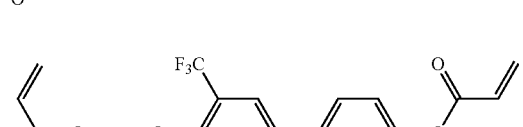
(a-47)
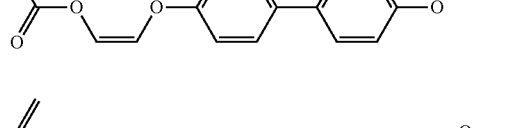
(a-48)
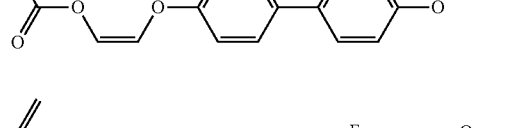
(a-49)
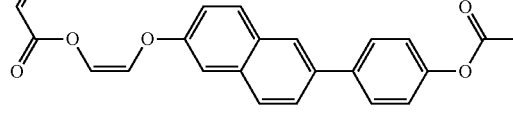
(a-50)
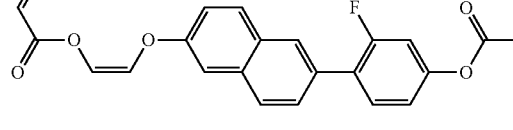
(a-51)
(a-52)
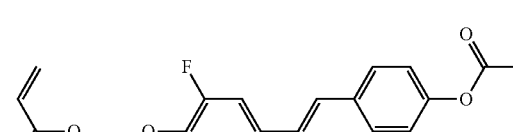
(a-53)
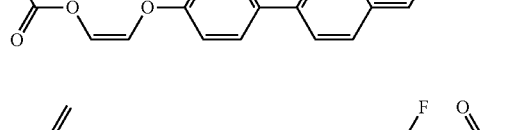
(a-54)
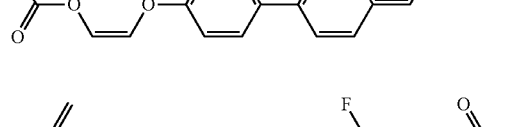
(a-55)
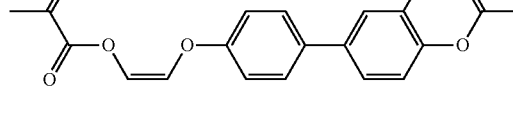
(a-56)
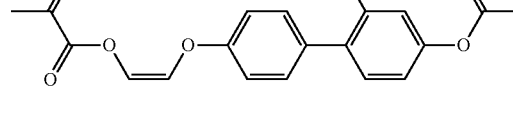
(a-57)
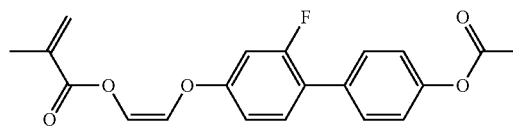
(a-58)
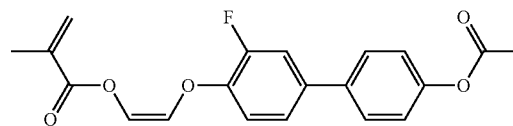

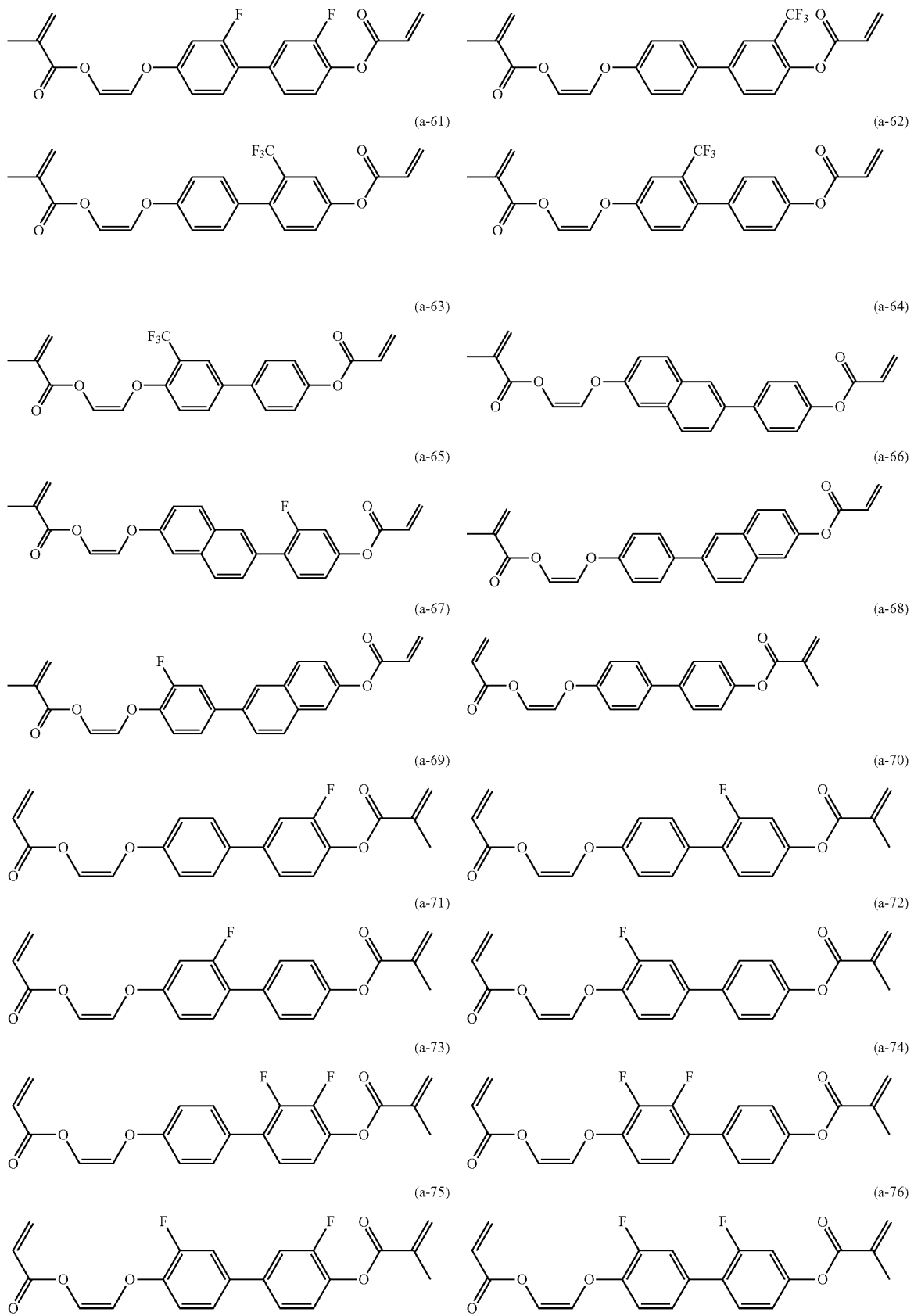

-continued
(a-77)
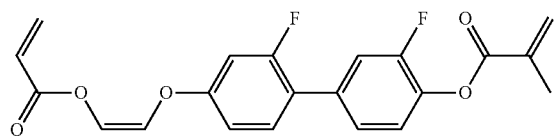
(a-78)
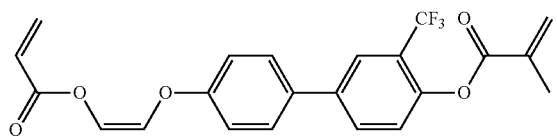
(a-79)
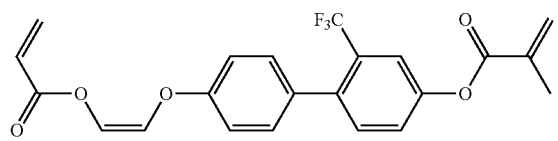
(a-80)
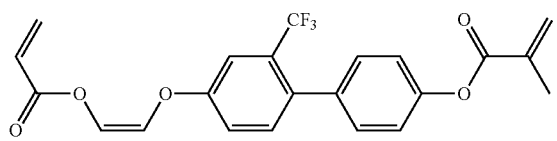
(a-81)
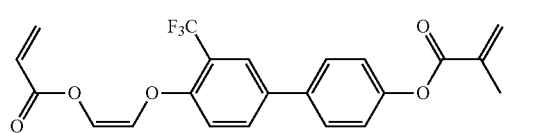
(a-82)
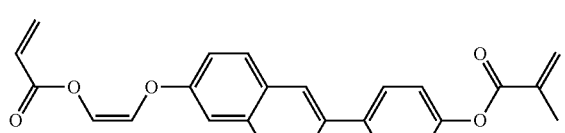
(a-83)
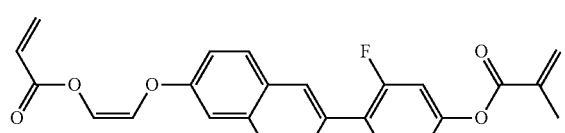
(a-84)
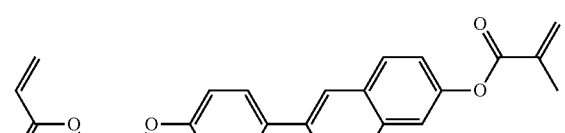
(a-85)
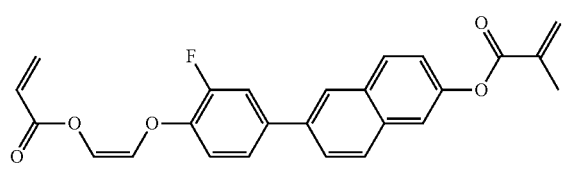
(a-86)
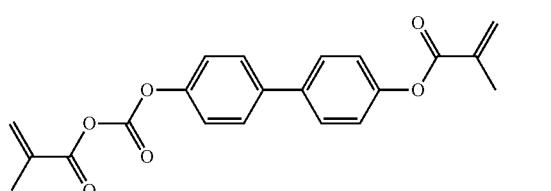
(a-87)
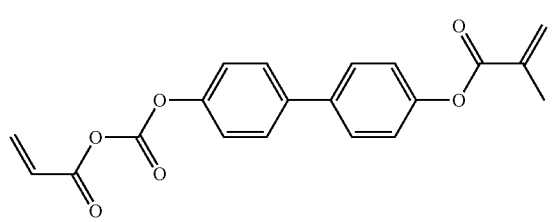
(a-88)
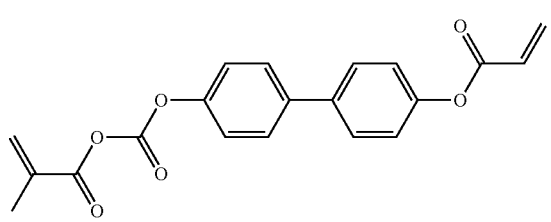
(a-89)
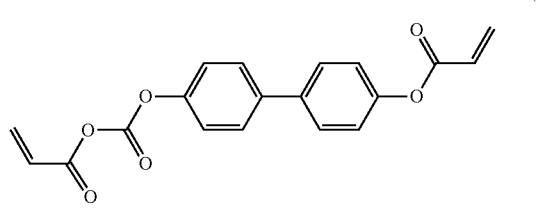
(a-90)
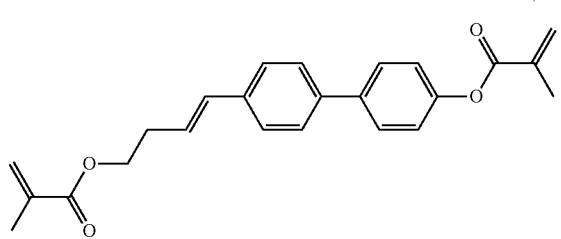

-continued
(a-91)
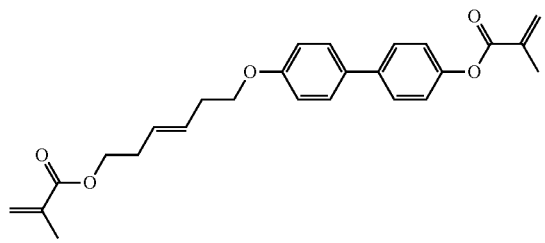
(a-92)
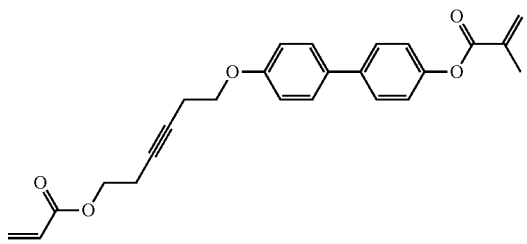
(a-93)
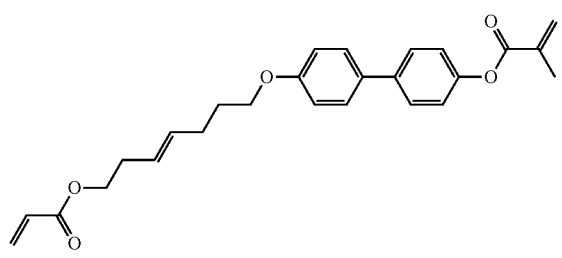
(a-94)
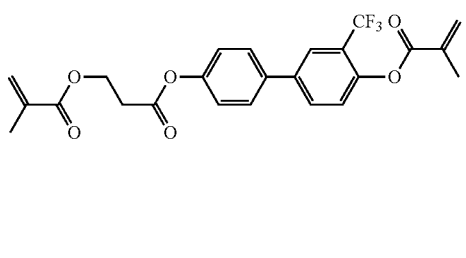
(a-95)
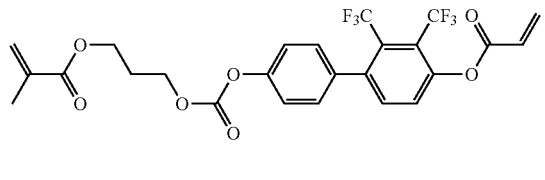
(a-96)
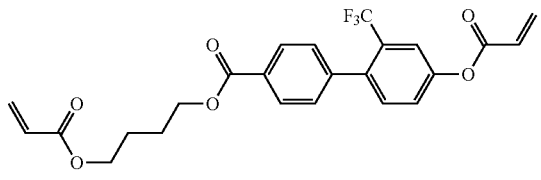
(a-97)
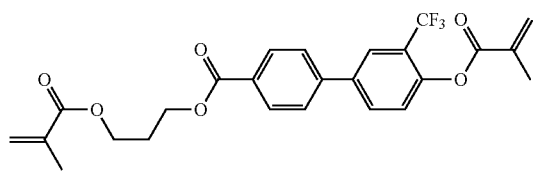
(a-98)
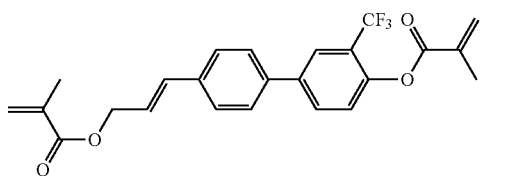
(a-99)
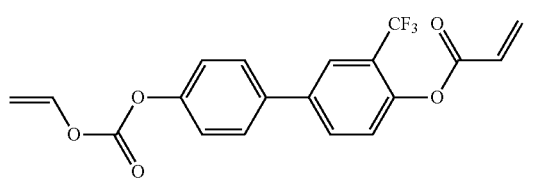
(a-100)
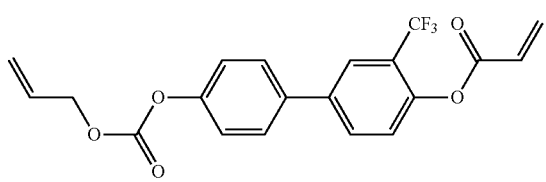
(a-101)
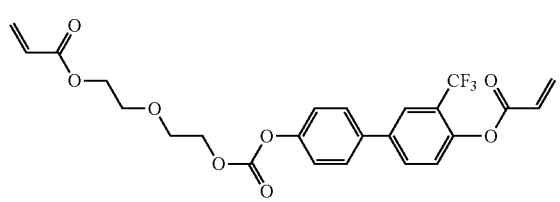
(a-102)
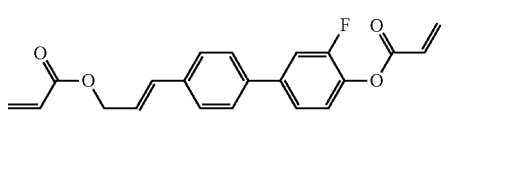
(a-103)
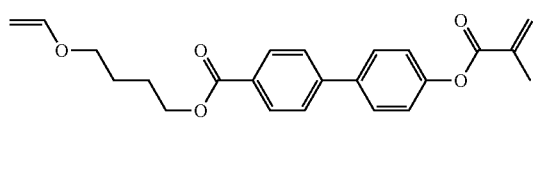
(a-104)
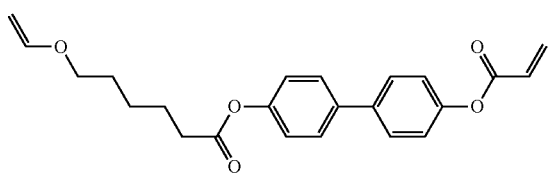

-continued
(a-105)
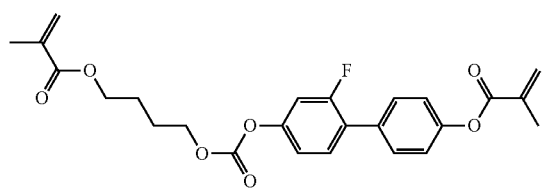
(a-106)
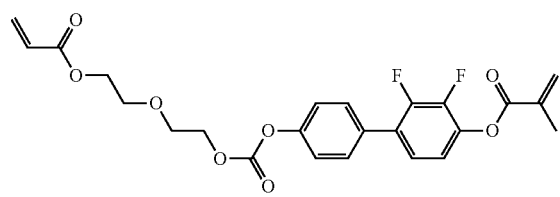
(a-107)
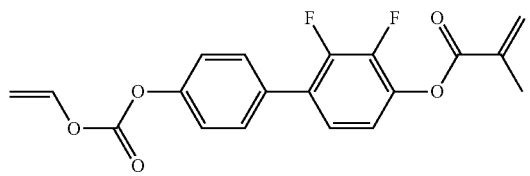
(a-108)
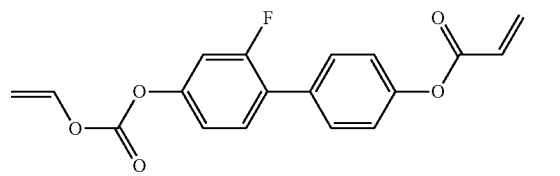
(a-109)
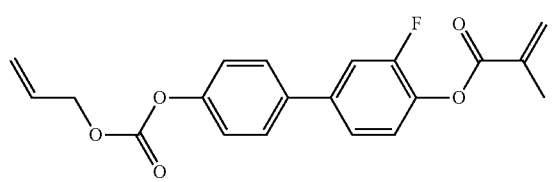
(a-110)
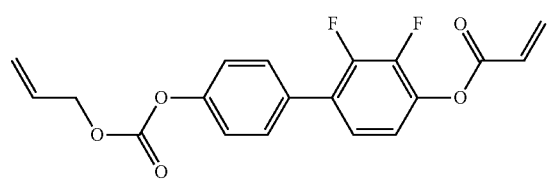
(a-111)
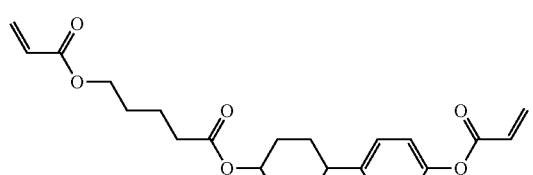
(a-112)
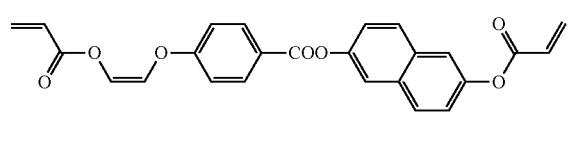
(a-113)
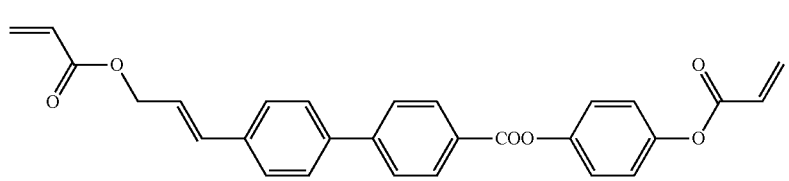
(a-114)
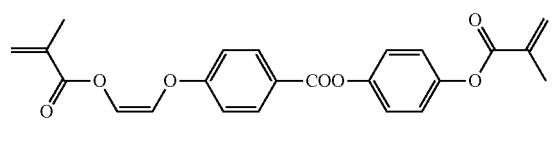
(a-115)
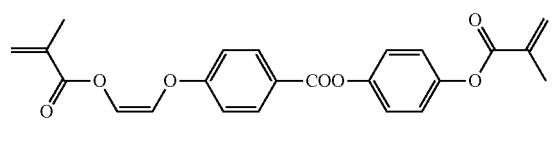
(a-116)
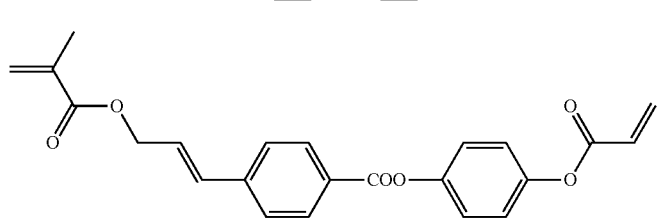

(a-117)
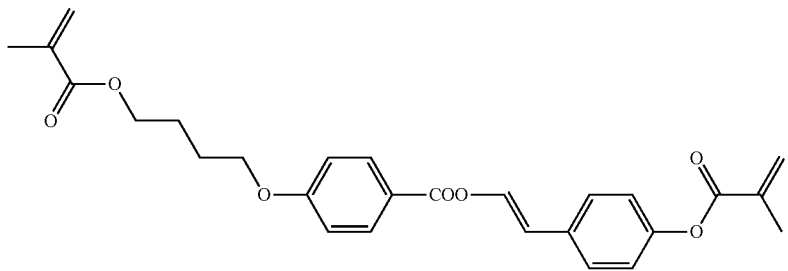
(a-118)
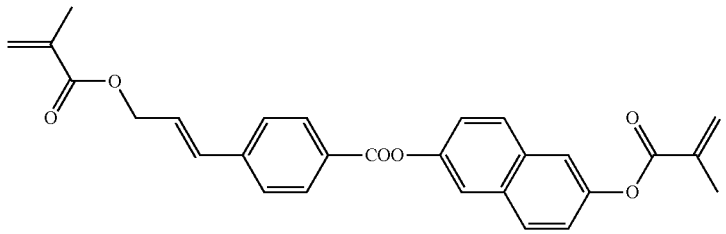
(a-119)
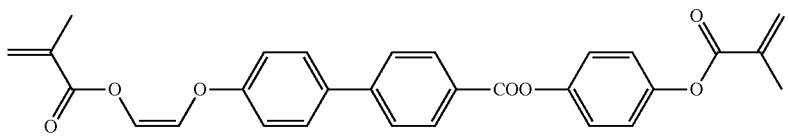
(a-120)
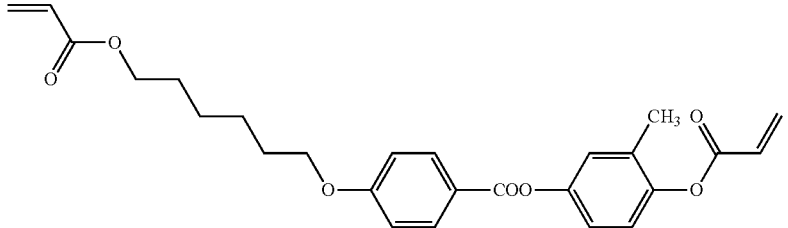
(a-121)
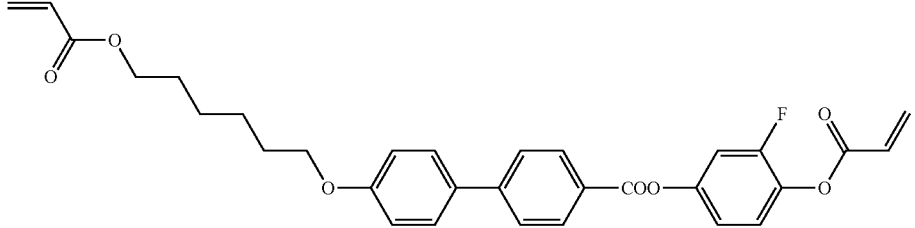
(a-122)
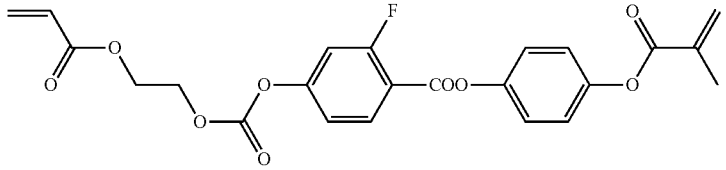
(a-123)
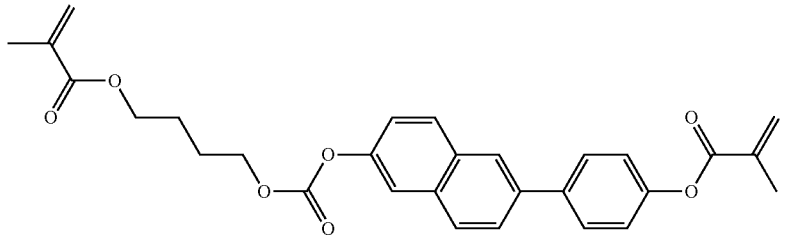

(a-124)
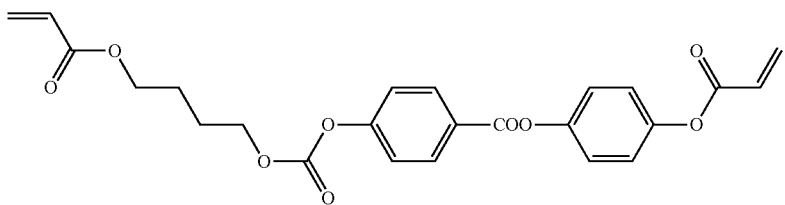
(a-125)
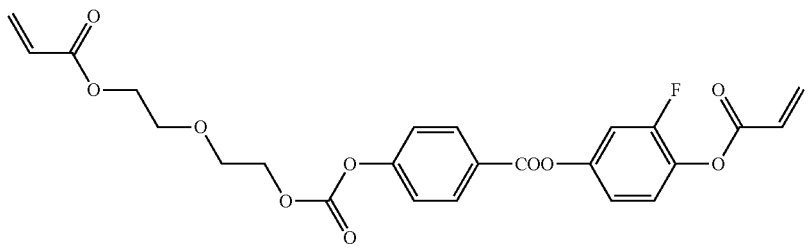
(a-126)
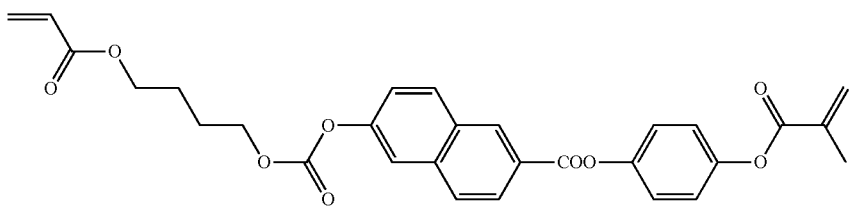
(a-127)
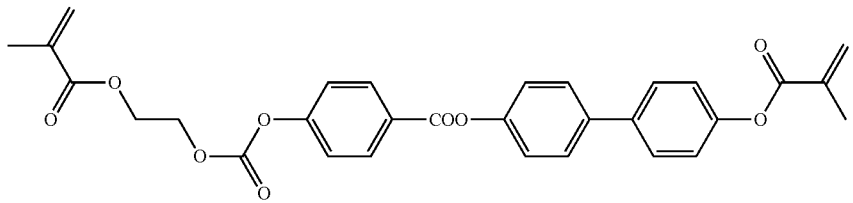
(a-128)
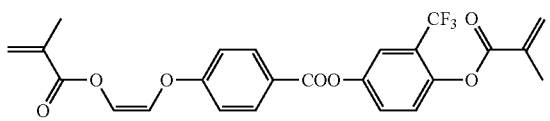
(a-129)
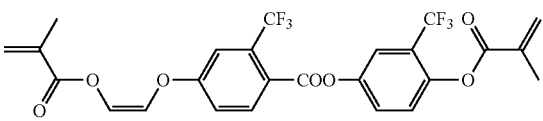
(a-130)
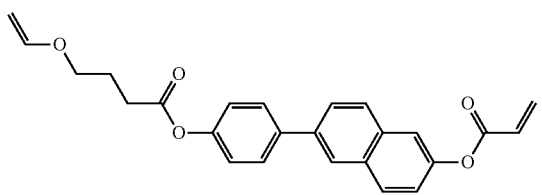
(a-131)
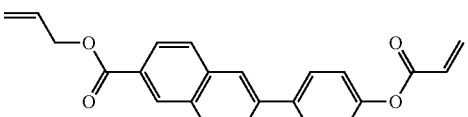
(a-132)
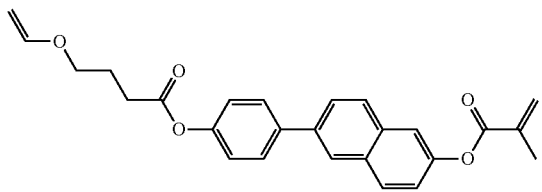
(a-133)
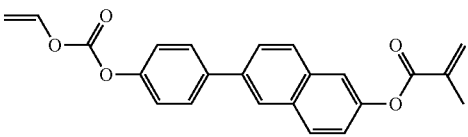

-continued
(a-134)
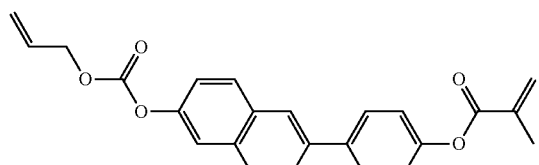
(a-135)
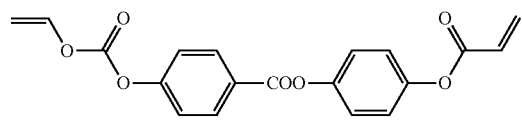
(a-136)
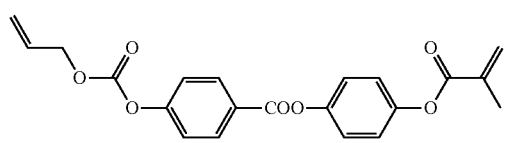
(a-137)
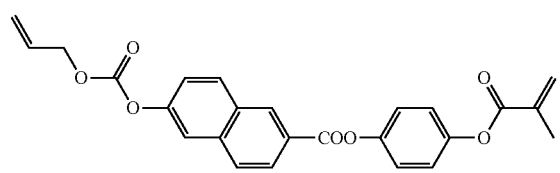
(a-138)
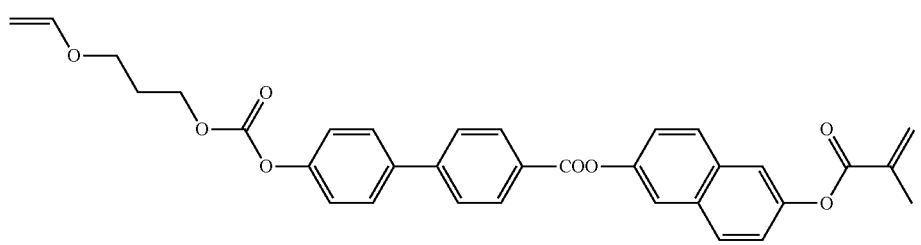
(a-139)
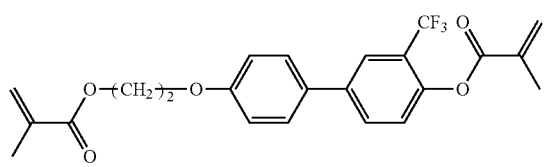
(a-140)
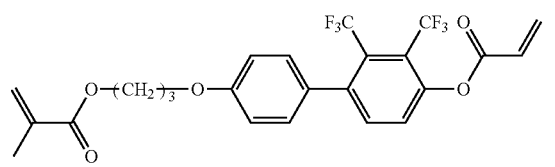
(a-141)
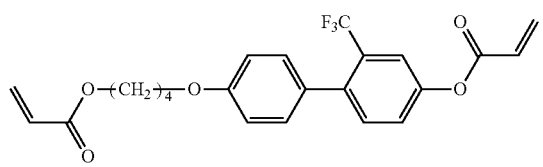
(a-142)
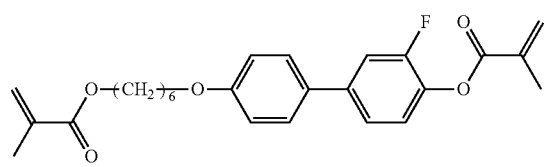
(a-143)
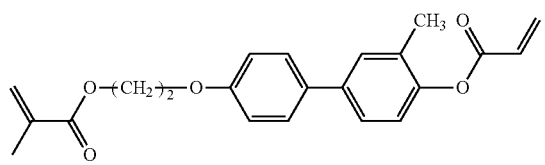
(a-144)
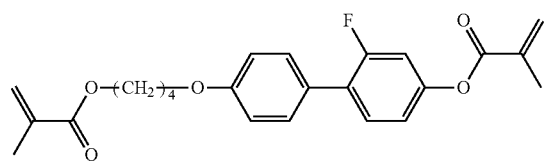
(a-145)
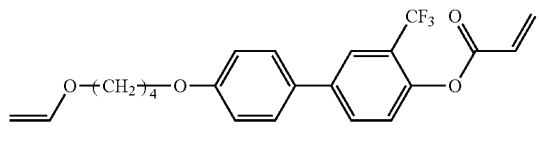
(a-146)
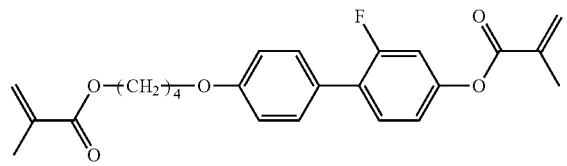
(a-147)
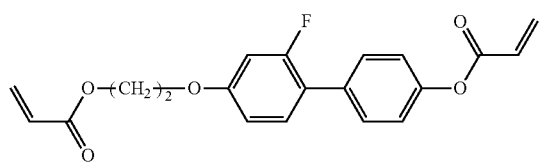
(a-148)
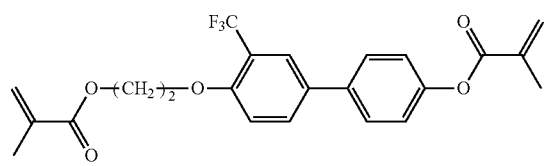

-continued
(a-149)
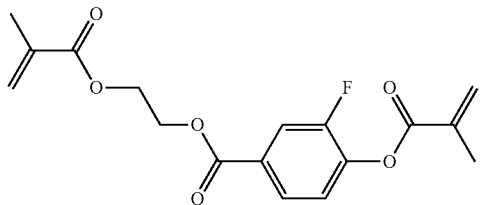
(a-150)
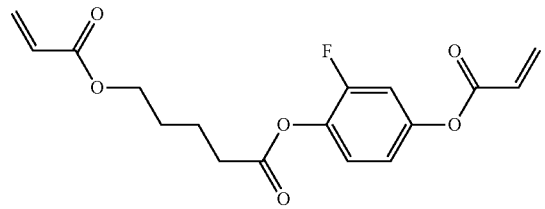
(a-151)
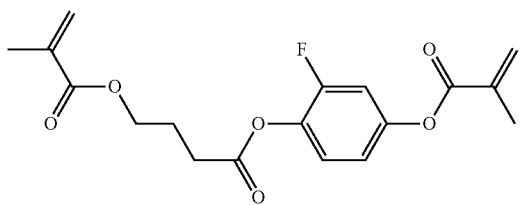
(a-152)
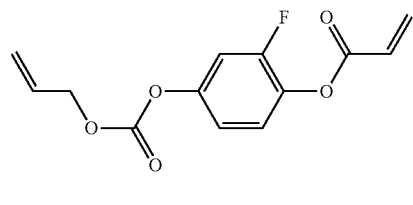
(a-153)
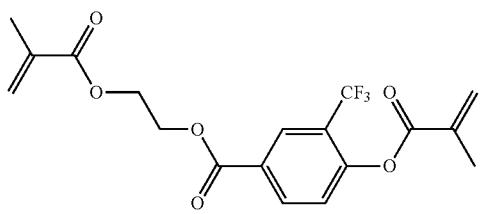
(a-154)
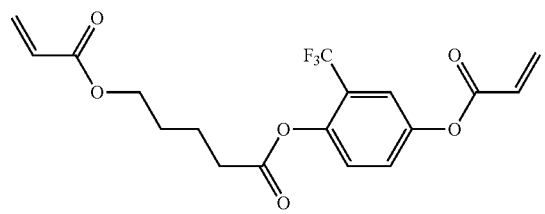
(a-155)
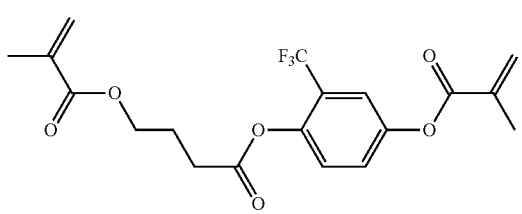
(a-156)
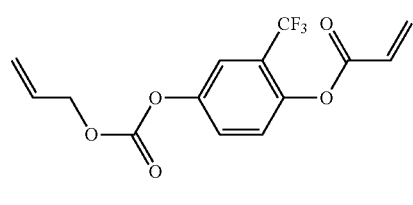
(a-157)
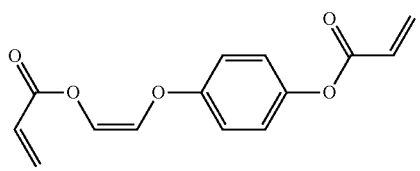
(a-158)
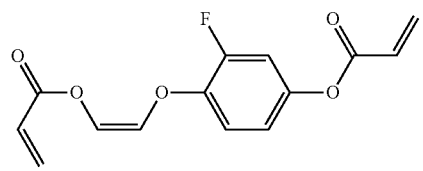
(a-159)
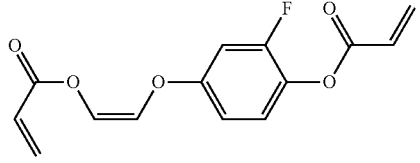
(a-160)
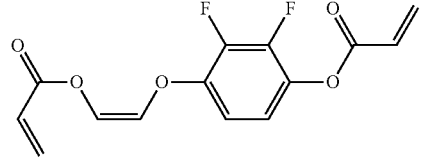
(a-161)
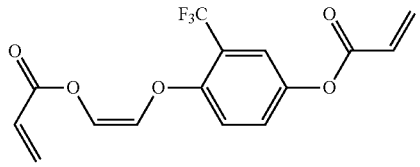
(a-162)
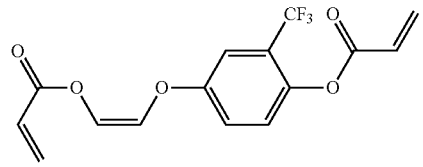
(a-163)
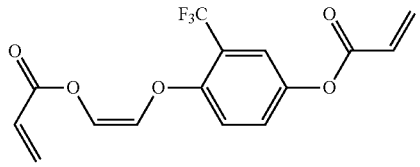
(a-164)
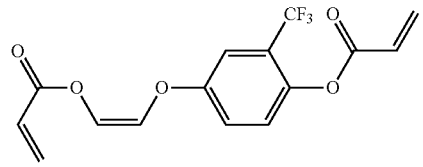

-continued
| | |
|---|---|
| (a-165) 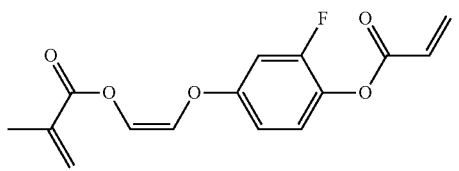 | (a-166) 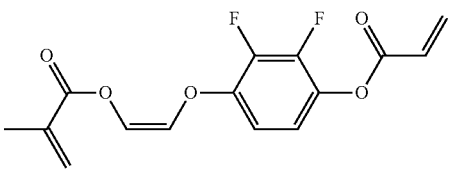 |
| (a-167) 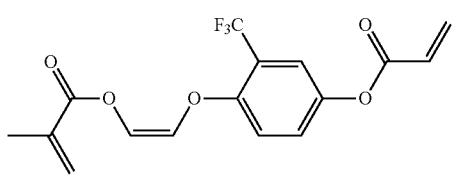 | (a-168) 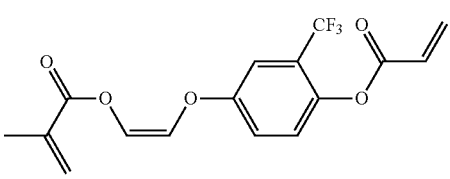 |
| (a-169) 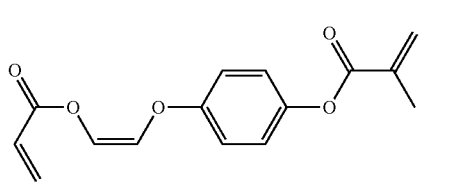 | (a-170) 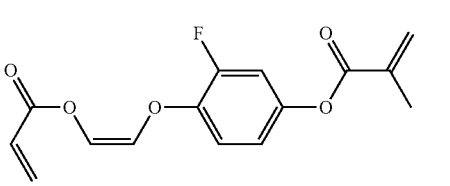 |
| (a-171) 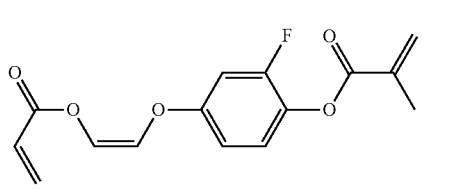 | (a-172) 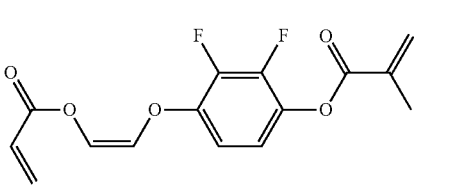 |
| (a-173) 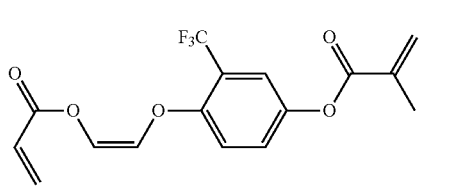 | (a-174) 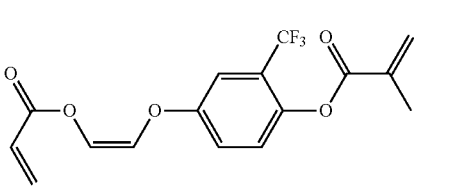 |
| (a-175) 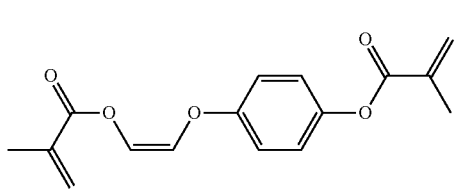 | (a-176) 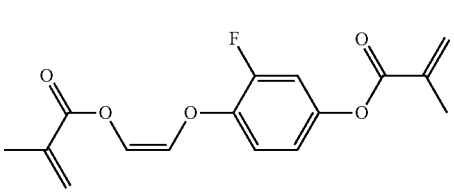 |
| (a-177) 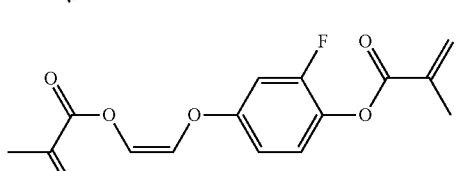 | (a-178) 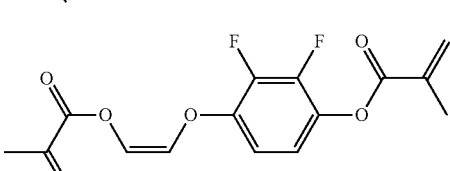 |
| (a-179) 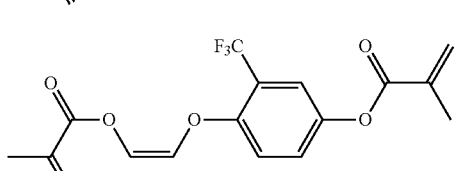 | (a-180) 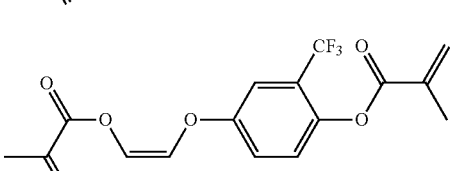 |
| (a-181) 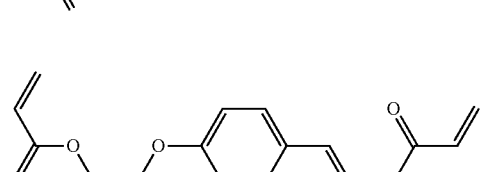 | (a-182) 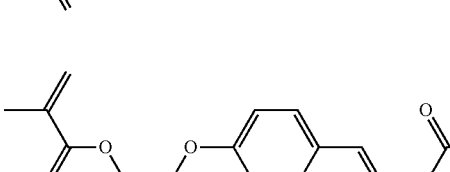 |

-continued
(a-183)
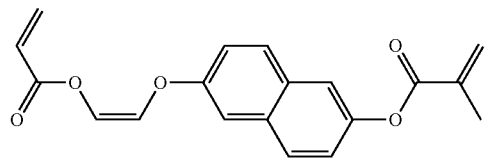
(a-184)
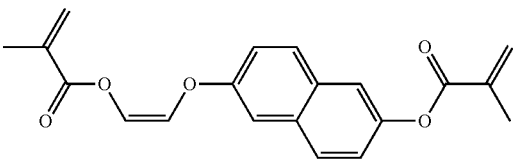
(a-185)
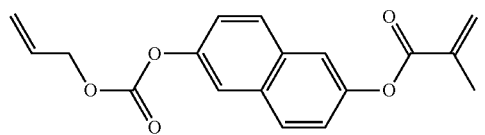
(a-186)
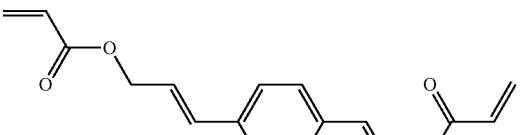
(a-187)
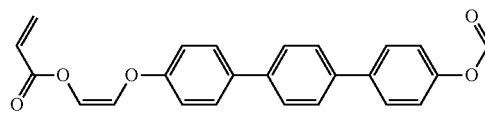
(a-188)
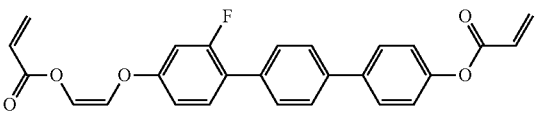
(a-189)
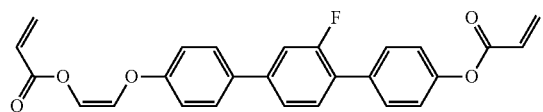
(a-190)
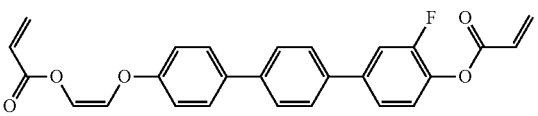
(a-191)
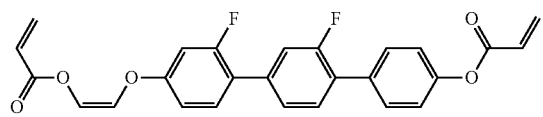
(a-192)
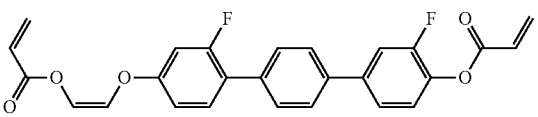
(a-193)
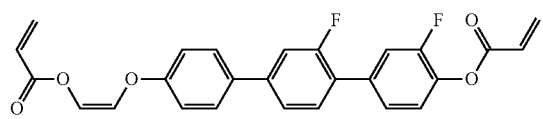
(a-194)
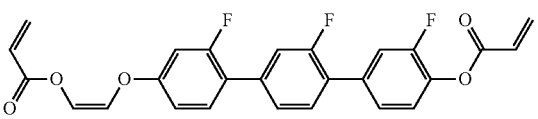
(a-195)
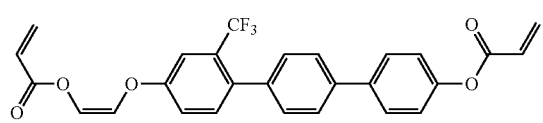
(a-196)
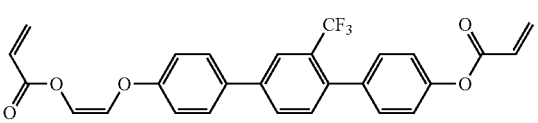
(a-197)
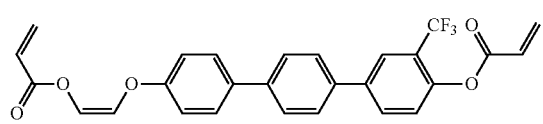
(a-198)
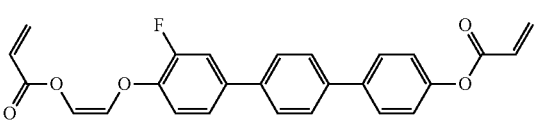
(a-199)
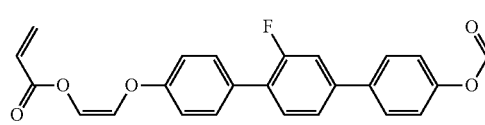
(a-200)
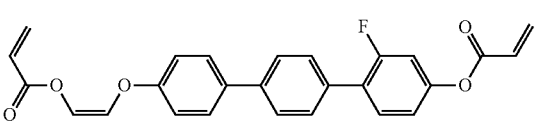
(a-201)
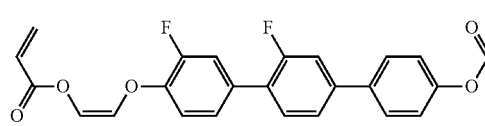

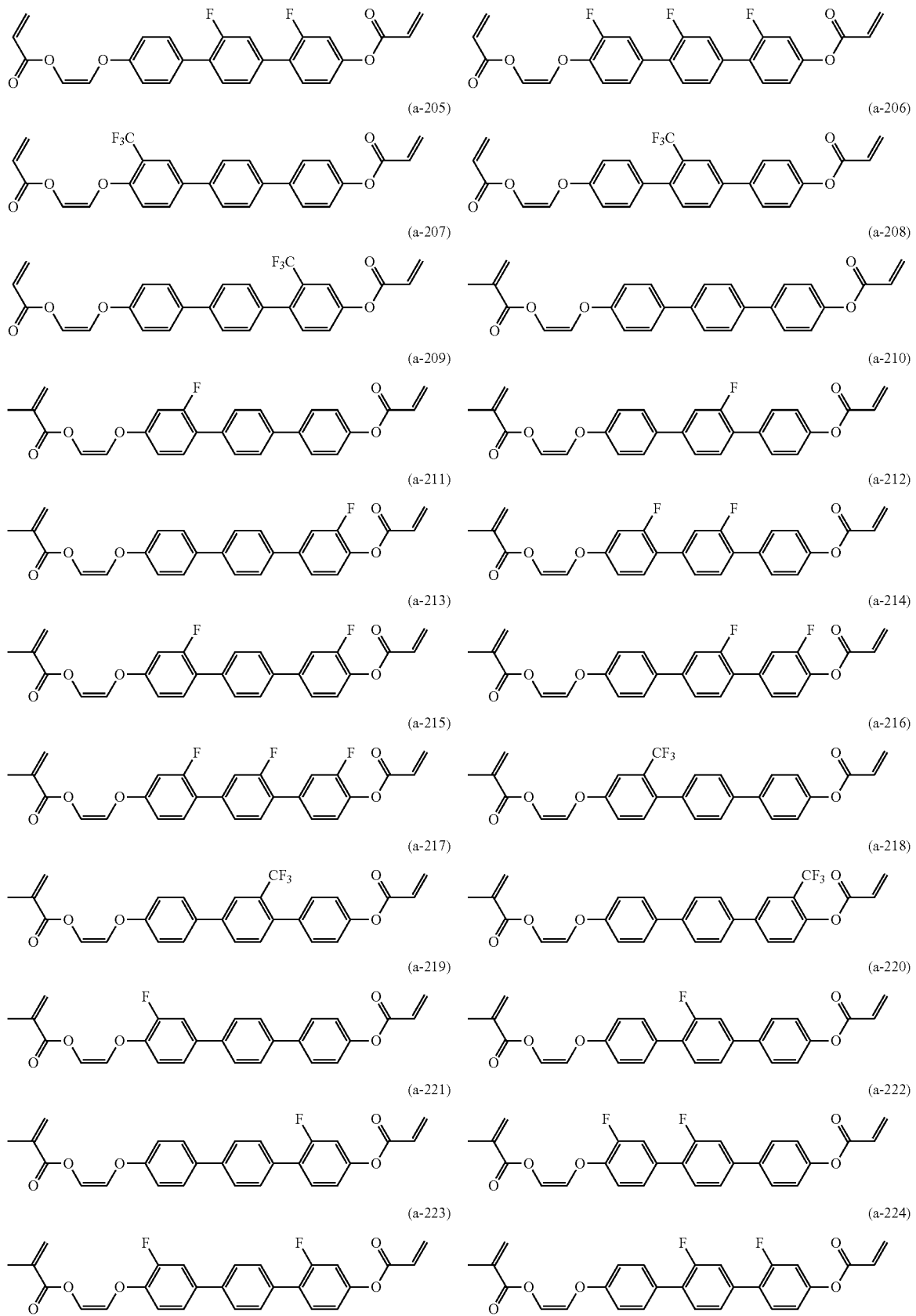

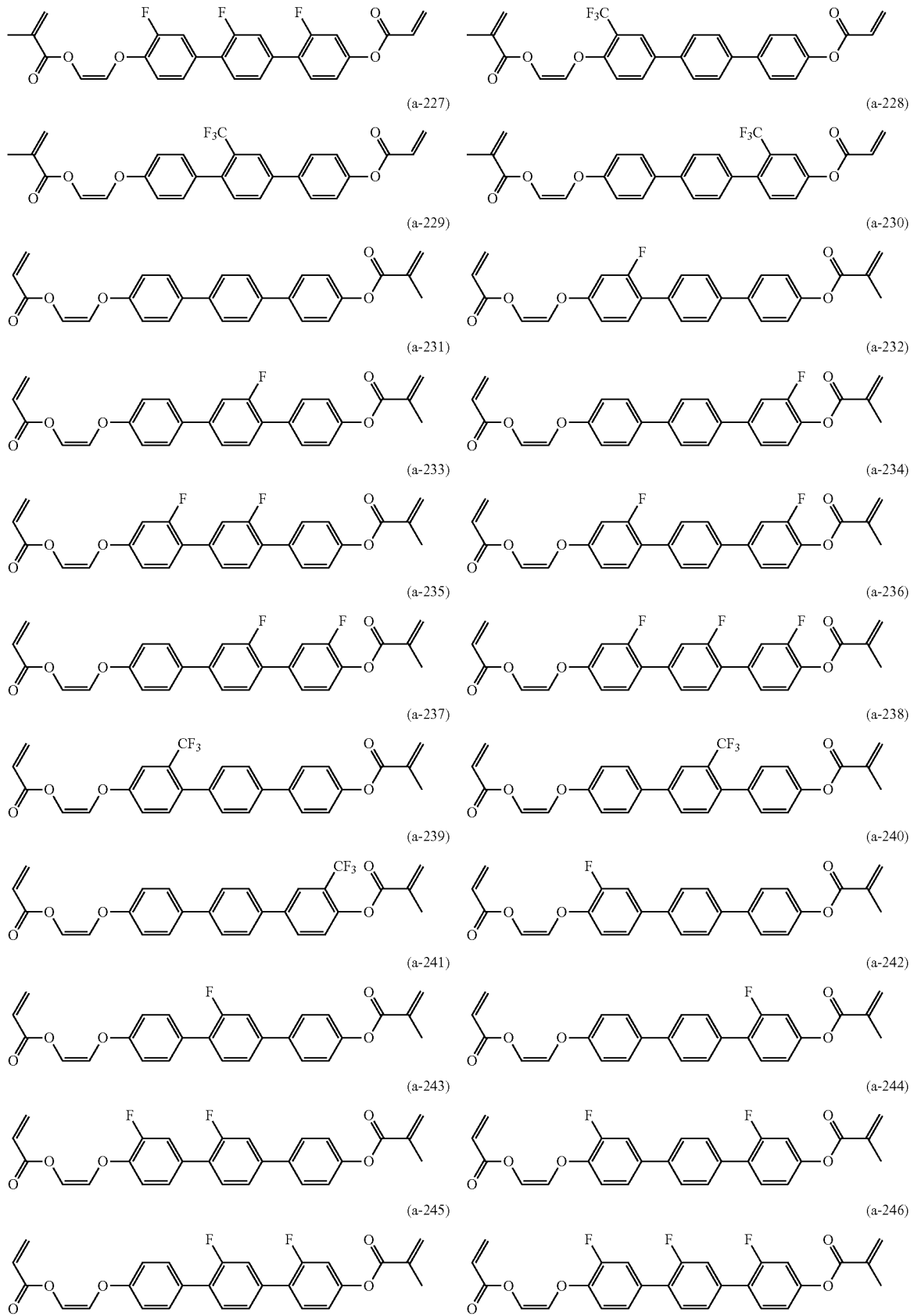

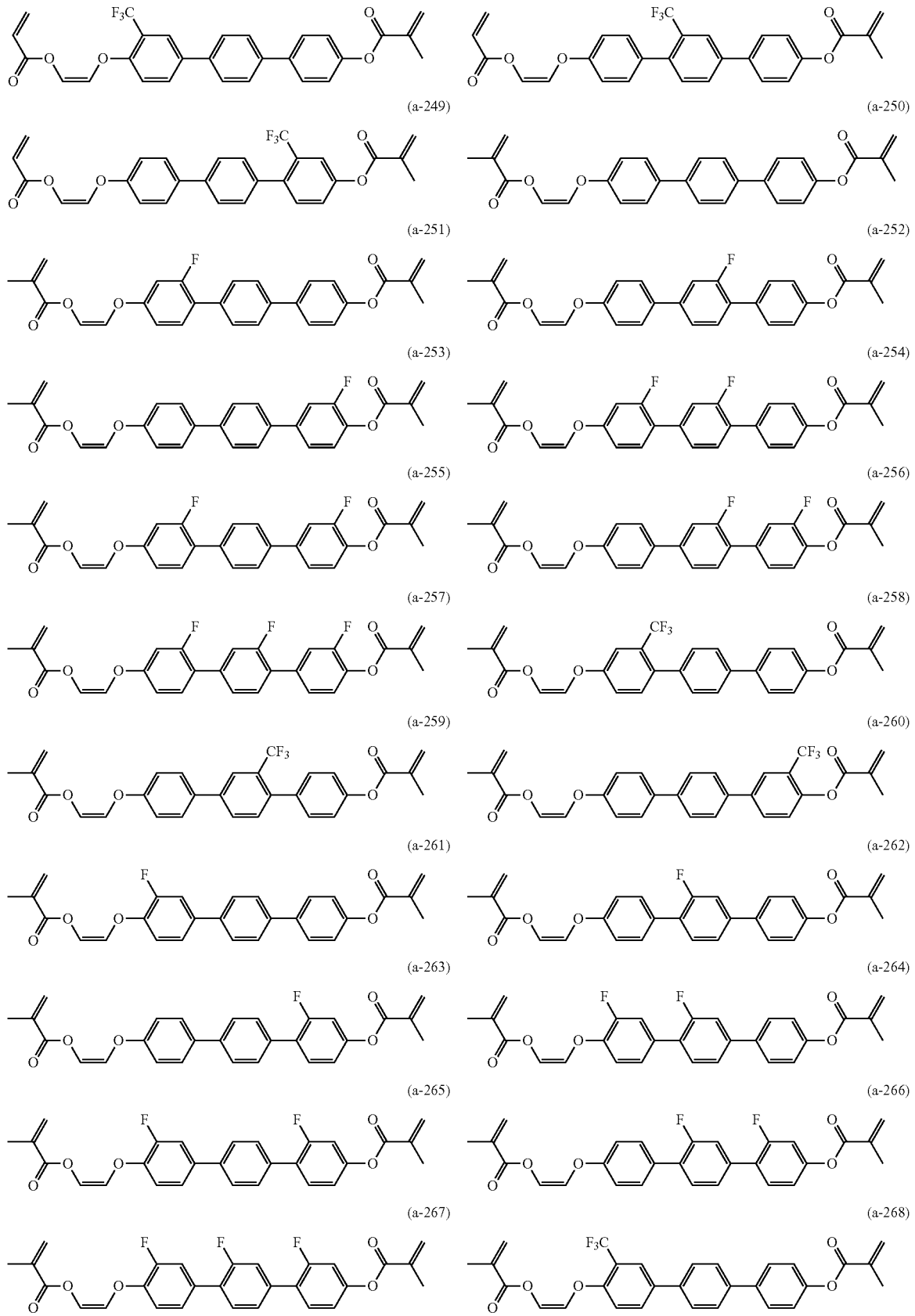

-continued
(a-269)
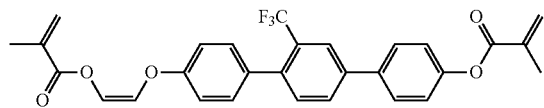
(a-270)
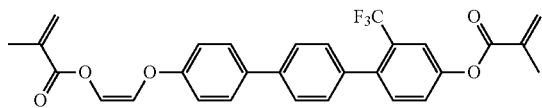
(a-271)
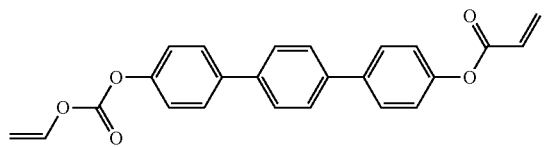
(a-272)
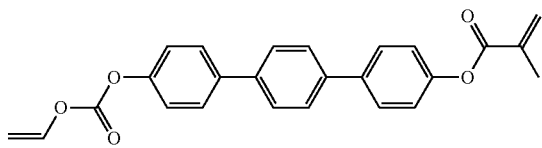
(a-273)
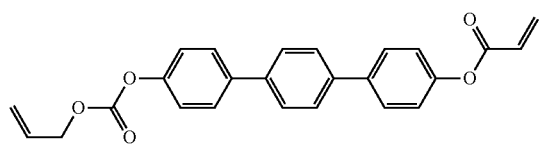
(a-274)
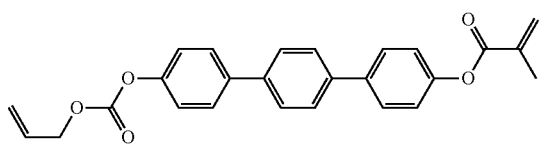
(a-275)
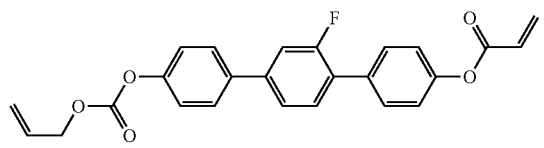
(a-276)
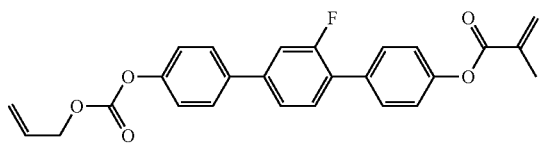
(a-277)
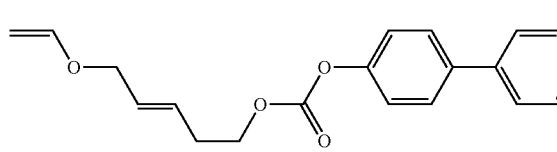
(a-278)
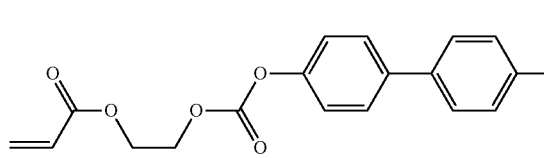
(a-279)
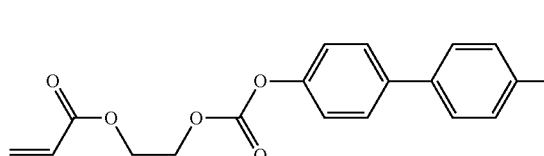
(a-280)
(a-281)
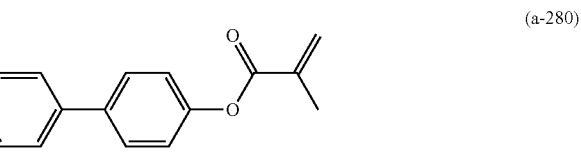
(a-282)

-continued
(a-283)
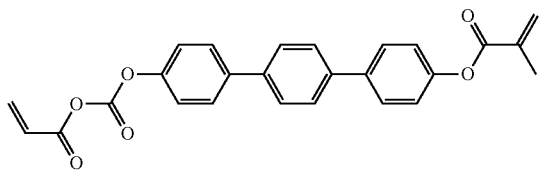
(a-284)
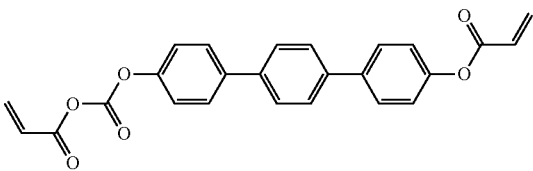
(a-285)
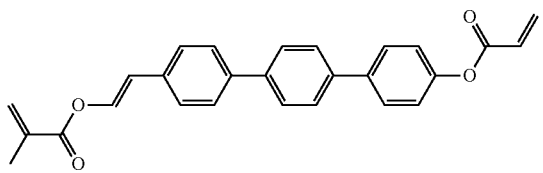
(a-286)
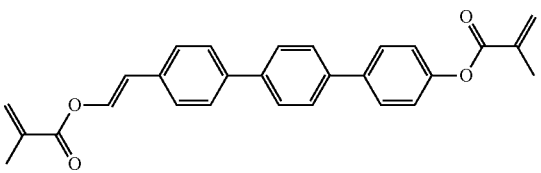
(a-287)
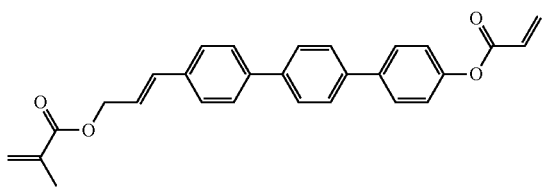
(a-288)
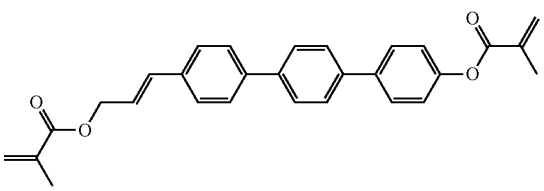
(a-289)
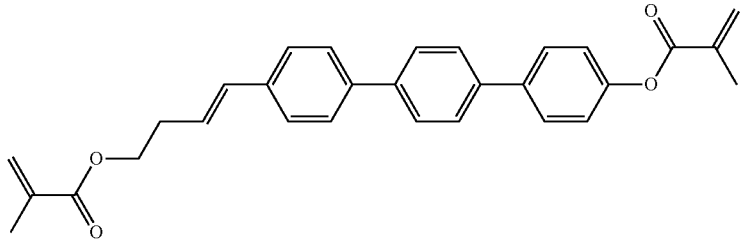
(a-290)
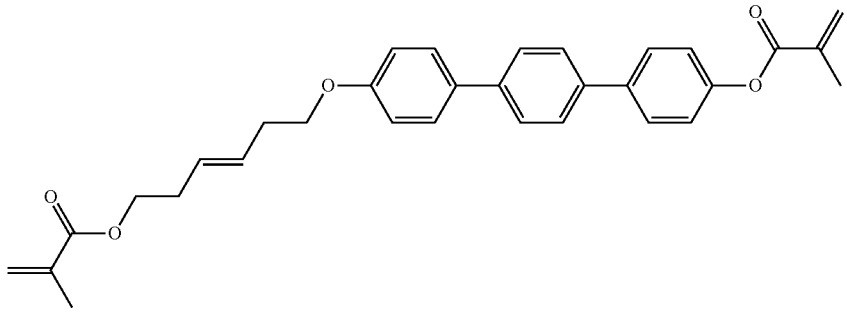
(a-291)
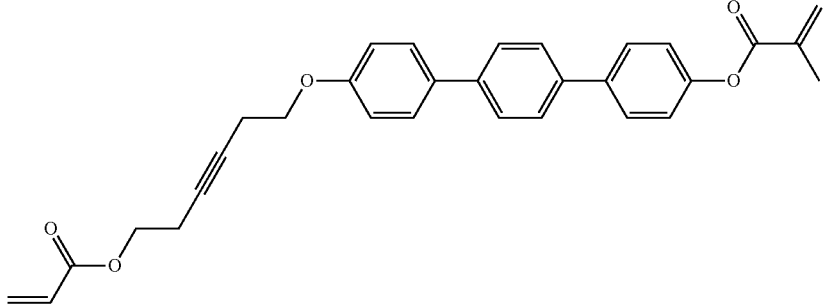

(a-292)

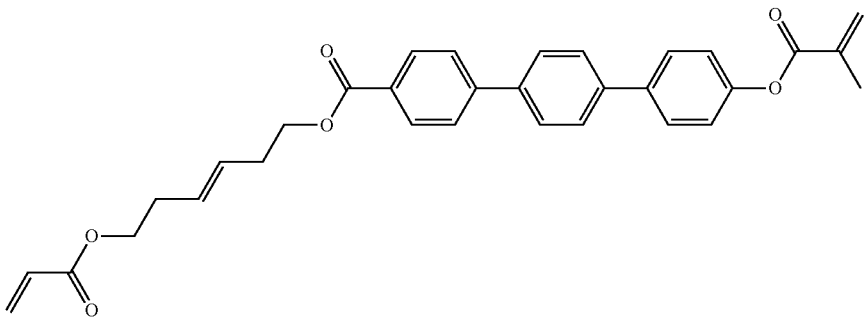

EXAMPLES

The invention will be explained below in more detail based on examples. However, the invention is not limited to the examples. Incidentally, the term "%" means "% by weight," unless otherwise noted.

Examples of the Compounds

Synthesized compounds were identified by means of proton magnetic resonance spectroscopy ($^1$H-NMR) and so forth. Melting points of the compounds were determined by differential scanning calorimetry (DSC). Analytical methods will be explained first.

$^1$H-NMR Analysis

Model DRX-500 apparatus (made by Bruker BioSpin Corporation) was used for measurement. A sample prepared in examples or the like was dissolved in a deuterated solvent such as $CDCl_3$ in which the sample was soluble, and the measurement was carried out under the conditions of room temperature, 500 MHz and twenty-four times of accumulation. In the explanation of the nuclear magnetic resonance spectra, the symbols s, d, t, q and m stand for a singlet, a doublet, a triplet, a quartet and a multiplet, respectively. Tetramethylsilane (TMS) was used as the standard reference material for the zero point of the chemical shift (δ values).

HPLC Analysis

Model Prominence (LC-20AD; SPD-20A) made by Shimadzu Corporation was used for measurement. A column YMC-Pack ODS-A (length 150 mm, bore 4.6 mm, particle size 5 μm) made by YMC Co., Ltd. was used. Acetonitrile and water were suitably mixed and used as eluent. A UV detector, a RI detector, a Corona detector and so forth were suitably used as a detector. A wavelength for the UV detector was 254 nm.

A sample was dissolved in acetonitrile to give a 0.1% by weight solution, and then 1 microliter of the solution was injected into the sample injector. Model C-R7Aplus made by Shimadzu Corporation was used as a recorder. The resulting chromatogram showed the retention time of the peaks and the values of the peak areas corresponding to the component compounds.

The ratio of the peak areas in the chromatogram of the HPLC corresponds to the ratio of component compounds. In general, the percentage by weight of each component compound in an analytical sample is not completely the same as the percentage of each peak area in the analytical sample. In the invention, however, the percentage by weight of the component compound in the analytical sample corresponds substantially to the percentage of the peak area in the analytical sample, because the correction coefficient is essentially 1 (one) when the column described above is used. This is because there is no significant difference among the correction coefficients of the liquid crystal compounds as components.

DSC Measurement

A sample was heated and then cooled at the rate of 3° C. per minute using a Perkin-Elmer differential scanning calorimeter, a DSC-7 System or a Diamond DSC System. The starting point of an endothermic peak or an exothermic peak caused by a phase change of the sample was obtained by means of the extrapolation, and the melting point was determined.

Sample for Measurement

A liquid crystal compound itself was used as a sample when the phase structure and the transition temperature were measured. A composition prepared by mixing the compound and mother liquid crystals was used as a sample when physical properties such as the maximum temperature of a nematic phase, viscosity, optical anisotropy, dielectric anisotropy were measured.

When a sample in which a compound was mixed with mother liquid crystals was used, the measurement was carried out according to the following method. The sample was prepared by mixing 15% by weight of the compound and 85% by weight of the mother liquid crystals. Extrapolated values were calculated from the measured values of the sample by means of an extrapolation method represented by the following equation, and their values were reported. [Extrapolated value]=(100×[Measured value of sample]−[% by weight of mother liquid crystals]×[Measured value of mother liquid crystals])/[% by weight of compound].

Measurement Method

The physical properties of compounds were measured according to the following methods. Most were methods described in the Standard of Electronic Industries Association of Japan, EIAJ•ED-2521A, or the modified methods. No TFT was attached to a TN device used for measurement.

(1) Phase Structure

A sample (a compound) was placed on a hot plate of a melting point apparatus (Hot Stage Model FP-52 made by Mettler Toledo International Inc.) equipped with a polarizing microscope, and the phase conditions and their changes were observed with the polarizing microscope while the sample was heated at the rate of 3° C. per minute, and the kinds of phases were specified.

(2) Transition Temperature (° C.)

A sample (a compound) was heated and then cooled at the rate of 3° C. per minute using a Perkin-Elmer differential scanning calorimeter, a DSC-7 System or a Diamond DSC System. The starting point of an endothermic peak or an exothermic peak caused by the phase change of the sample was obtained by means of the extrapolation, and thus the transition temperature was determined. The transition temperature of a compound from solid to a liquid crystal phase such as a smectic phase or a nematic phase may be abbreviated to "the minimum temperature of a liquid crystal phase". The transition temperature of a compound from a liquid crystal phase to liquid may be abbreviated to "a clearing point".

The symbol C stood for crystals, which were expressed as $C_1$ and $C_2$ when the kinds of crystals were distinguishable. The symbols S and N stood for a smectic phase and a nematic phase, respectively. When a smectic A phase, a smectic B phase, a smectic C phase or a smectic F were distinguishable in the smectic phases, they were expressed as $S_A$ $S_B$ $S_C$ or $S_F$ respectively. The symbol I stood for a liquid (isotropic). Transition temperatures were expressed as, for example, "C 50.0 N 100.0 Iso", which means that the transition temperature from crystals to a nematic phase (CN) was 50.0° C., and the transition temperature from the nematic phase to a liquid (clearing point) was 100.0° C.

(3) Compatibility at Low Temperatures

Samples were prepared by mixing a compound with mother liquid crystals so that the ratio of the compound became 20% by weight, 15% by weight, 10% by weight, 5% by weight, 3% by weight and 1% by weight, and placed in glass vials. After these glass vials had been kept in a freezer at −10° C. or −20° C. for a certain period of time, they were observed as to whether or not crystals (or a smectic phase) had deposited.

(4) Maximum Temperature of a Nematic Phase ($T_{NI}$ or NI; ° C.)

A sample was placed on a hot plate in a melting point apparatus equipped with a polarizing microscope and was heated at the rate of 1° C. per minute. The temperature was measured when part of the sample began to change from a nematic phase to an isotropic liquid. A higher limit of the temperature range of a nematic phase may be abbreviated to "the maximum temperature."

(5) Minimum Temperature of a Nematic Phase ($T_C$; ° C.)

A sample having a nematic phase was kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., $T_C$ was expressed as ≤−20° C. A lower limit of the temperature range of a nematic phase may be abbreviated to "the minimum temperature."

(6) Viscosity (Bulk Viscosity; η; measured at 20° C.; mPa·s)

An E-type viscometer was used for measurement.

(7) Viscosity (Rotational Viscosity; γ1; Measured at 25° C.; mPa·s)

Measurement was carried out according to the method described in M. Imai, et al., Molecular Crystals and Liquid Crystals, Vol. 259, 37 (1995). A sample was poured into a TN device in which the twist angle was 0 degrees and the distance between the two glass substrates (cell gap) was 5 micrometers. A voltage with an increment of 0.5 volt in the range of 16 to 19.5 volts was applied stepwise to the device. After a period of 0.2 second with no voltage, a voltage was applied repeatedly under the conditions of only one rectangular wave (rectangular pulse; 0.2 second) and of no voltage (2 seconds). The peak current and the peak time of the transient current generated by the applied voltage were measured. The value of rotational viscosity was obtained from the measured values and the calculating equation (8) on page 40 of the paper presented by M. Imai, et al. The value of dielectric anisotropy necessary for this calculation was obtained by use of the device that had been used for the measurement of rotational viscosity, according to the method that will be described below.

(8) Optical Anisotropy (Refractive Index Anisotropy; Δn; Measured at 25° C.)

Measurement was carried out using an Abbe refractometer with a polarizing plate attached to the ocular, using light at a wavelength of 589 nanometers. The surface of the main prism was rubbed in one direction, and then a sample was placed on the main prism. The refractive index (n∥) was measured when the direction of the polarized light was parallel to that of the rubbing. The refractive index (n⊥) was measured when the direction of polarized light was perpendicular to that of the rubbing. The value of the optical anisotropy (Δn) was calculated from the equation: Δn=n∥−n⊥

(9) Dielectric Anisotropy (Δ∈; Measured at 25° C.)

A sample was poured into a TN device in which the distance between the two glass substrates (cell gap) was 9 micrometers and the twist angle was 80 degrees. Sine waves (10 V, 1 kHz) were applied to this device, and the dielectric constant (∈∥) in a major axis direction of liquid crystal molecules was measured after 2 seconds. Sine waves (0.5 V, 1 kHz) were applied to the device and the dielectric constant (∈⊥) in a minor axis direction of the liquid crystal molecules was measured after 2 seconds. The value of dielectric anisotropy was calculated from the equation: Δ∈=∈∥−∈⊥.

(10) Elastic Constant (K; Measured at 25° C.; pN)

A LCR meter Model HP 4284-A made by Yokokawa Hewlett-Packard, Ltd. was used for measurement. A sample was poured into a homogeneous device in which the distance between the two glass substrates (cell gap) was 20 micrometers. An electric charge of 0 volts to 200 volts was applied to the cell, and the electrostatic capacity and the applied voltage were measured. The measured values of the electric capacity (C) and the applied voltage (V) were fitted to the equation (2.98) and the equation (2.101) in page 75 of the "Ekisho Debaisu Handobukku" (Liquid Crystal Device Handbook, in English; The Nikkan Kogyo Shimbun, Ltd., Japan) and the values of $K_{11}$ and $K_{33}$ were obtained from the equation (2.99). Next, the value of $K_{22}$ was calculated from the equation (3.18) in page 171 and the values of $K_{11}$ and $K_{33}$ thus obtained. The elastic constant was an average value of $K_{11}$, $K_{22}$ and $K_{33}$.

(11) Threshold Voltage (Vth; Measured at 25° C.; V)

Measurement was carried out with an LCD evaluation system Model LCD-5100 made by Otsuka Electronics Co., Ltd. The light source was a halogen lamp. A sample was poured into a TN device having a normally white mode, in which the distance between the two glass substrates (cell gap) was about 0.45/Δn (micrometers) and the twist angle was 80 degrees. Voltage to be applied to the device (32 Hz, rectangular waves) was stepwise increased in 0.02 V increments from 0 V up to 10V. During the increase, the device was irradiated with light in the perpendicular direction, and the amount of light passing through the device was measured. A voltage-transmittance curve was prepared, in which the maximum amount of light corresponded to 100% transmittance and the minimum amount of light corresponded to 0% transmittance. The threshold voltage was voltage at 90% transmittance.

Example 1

Preparation of the Compound (a-4)

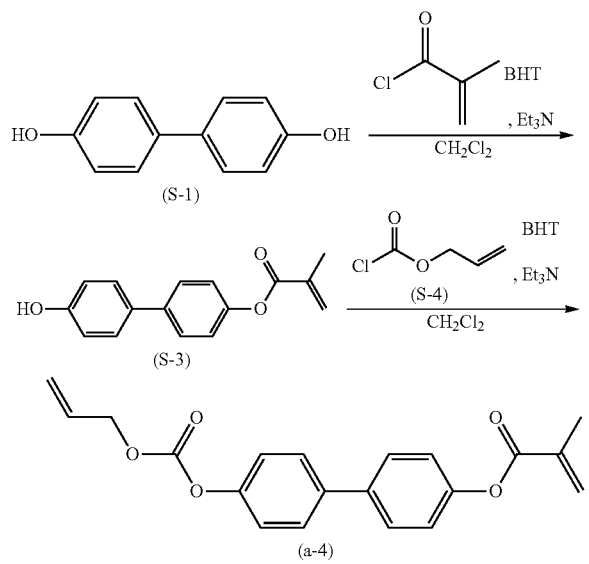

First Step: Preparation of the Compound (S-3)

The compound (S-2) (17.5 g, 0.167 mol) in dichloromethane (40 mL) solution was added dropwise to a mixture of the compound (S-1) (50.0 g, 0.269 mol), triethylamine (20.4 g, 0.202:mol), 2,6-di-tert-butyl-p-cresol (BHT) (5.000 mg, 0.0220 mmol) and dichloromethane (500 mL) in an ice bath under an atmosphere of nitrogen, and then the mixture was warmed gradually to room temperature. After 16 hours of stirring at room temperature, the reaction mixture was poured into water, and the organic layer was washed successively with 1M-hydrochloric acid and then brine. The organic layer was dried over anhydrous magnesium sulfate, and the organic solvent was distilled off under reduced pressure. The residue was purified by silica gel column chromatography (eluent, heptane:ethyl acetate=5:5 by volume) to give the compound (S-3) as colorless crystals (18.6 g).

Second Step: Preparation of the Compound (a-4)

The compound (S-4) (4.17 g, 0.0346 mol) in dichloromethane (10 mL) solution was added dropwise to a mixture of the compound (S-3) (16.0 g, 0.0629 mol), triethylamine (3.82 g, 0.0377 mol), BHT (5.000 mg, 0.0220 mmol) and dichloromethane (200 mL) in an ice bath under an atmosphere of nitrogen, and then the mixture was warmed gradually to room temperature. After 16 hours of stirring at room temperature, the reaction mixture was poured into water, and the organic layer was washed successively with 1M-hydrochloric acid, brine and 1M-sodium hydroxide aqueous solution. The organic layer was dried over anhydrous magnesium sulfate, and the organic solvent was distilled off under reduced pressure. The residue was purified by silica gel column chromatography (eluent, toluene:ethyl acetate=9:1 by volume), and then by recrystallization from a mixed solvent of ethanol and dichloromethane to give the compound (a-4) as colorless crystals (17.1 g).

Melting point: 67.0° C.

$^1$H-NMR (DMSO-d; δ ppm): 7.57 (dd, 4H), 7.26 (dd, 2H), 7.20 (dd, 2H), 6.38 (s, 1H), 6.06-5.98 (m, 1H), 5.78 (t, 1H), 5.47-5.43 (m, 1H), 5.35 (dd, 1H), 4.77-4.76 (m, 2H), and 2.08 (s, 3H).

Example 2

Preparation of the Compound (a-14)

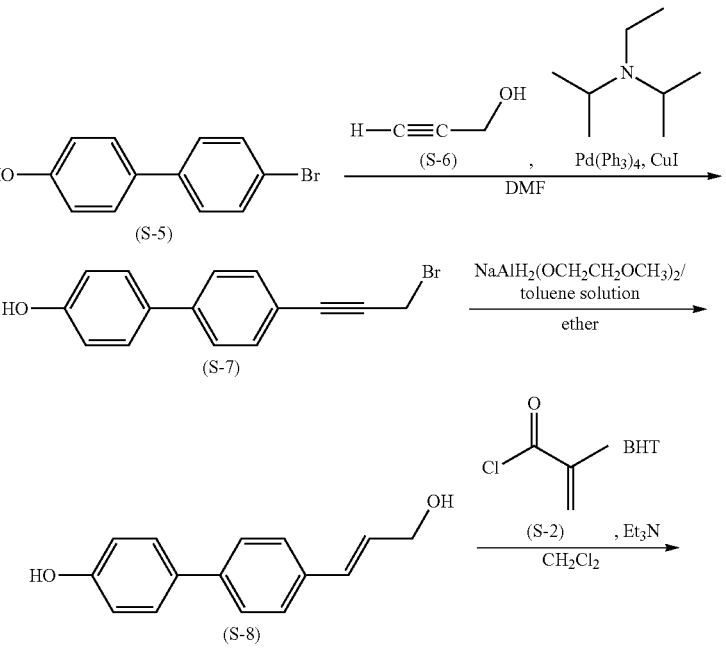

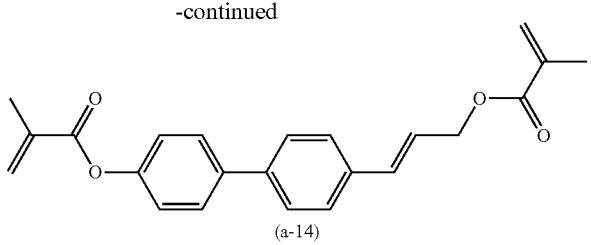

(a-14)

First Step: Preparation of the Compound (S-7)

The compound (S-6) (5.40 g, 0.0964 mol) was added dropwise to a mixture of the compound (S-5) (20.0 g, 0.0803 mol), tetrakis(triphenylphosphine)palladium (3.71 g, 3.21 mmol), copper iodide (1.84 g, 9.64 mmol), N,N-diisopropylethylamine (20 mL) and N,N-dimethylformamide (DMF) (100 mL) in an ice bath under an atmosphere of nitrogen, and stirring was continued for another. 1 hour. The reaction mixture was then heated at 50° C. and the stirring was continued for another 4 hours. The reaction mixture was poured into water, to which 2M-hydrochloric acid was added to acidify the mixture. The aqueous layer was extracted with diethyl ether, and dried over anhydrous magnesium sulfate. The organic solvent was distilled off under reduced pressure to give the compound (S-7) (15.8 g).

Second Step: Preparation of the Compound (S-8)

The compound (S-7) (12.0 g, 0.0535 mol) in diethyl ether (60 mL) solution was added dropwise to sodium bis(2-methoxyethoxy)aluminum hydride (3.6 mol/L toluene solution) (24.0 mL, 0.0864 mol) in diethyl ether (50 mL) solution in an ice bath under an atmosphere of nitrogen. After the addition had been completed, the reaction mixture was warmed up to room temperature, and the stirring was continued for another 1 hour. 1M-Sulfuric acid (70 mL) was added dropwise to the reaction mixture, and the organic layer was washed successively with water and brine, and then dried over anhydrous magnesium sulfate. The organic solvent was distilled off under reduced pressure to give the compound (S-8) (9.53 g).

Third Step: Preparation of the Compound (a-14)

The compound (S-2) (6.09 g, 0.0583 mol) in dichloromethane (5 mL) solution was added dropwise to a mixture of the compound (S-8) (6.00 g, 0.0265 mol), triethylamine (5.90 g, 0.0583 mol), BHT (5.000 mg, 0.0220 mmol) and dichloromethane (100 mL) in an ice bath under an atmosphere of nitrogen, and then the mixture was warmed gradually to room temperature. After 16 hours of stirring, the reaction mixture was poured into water, and the organic layer was washed successively with 1M-hydrochloric acid, brine and 1M-sodium hydroxide aqueous solution. The organic layer was dried over anhydrous magnesium sulfate, and the organic solvent was distilled off under reduced pressure. The residue was purified by silica gel column chromatography (eluent, toluene:ethyl acetate=9:1 by volume), and then by recrystallization from a mixed solvent of ethanol and dichloromethane to give the compound (a-14) as colorless crystals (6.77 g).

Melting point: 72.0° C.

$^1$H-NMR (DMSO-d; δ ppm): 7.61 (d, 2H), 7.55 (d, 2H), 7.47 (d, 2H), 7.20 (d, 2H), 6.71 (d, 2H), 6.40-6.35 (m, 1H), 6.38 (s, 1H), 6.17 (s, 1H), 5.78 (t, 1H), 5.61 (t, 1H), 4.84 (dd, 2H), 2.09 (s, 3H), and 1.99 (s, 3H).

Example 3

Preparation of the Compound (a-17)

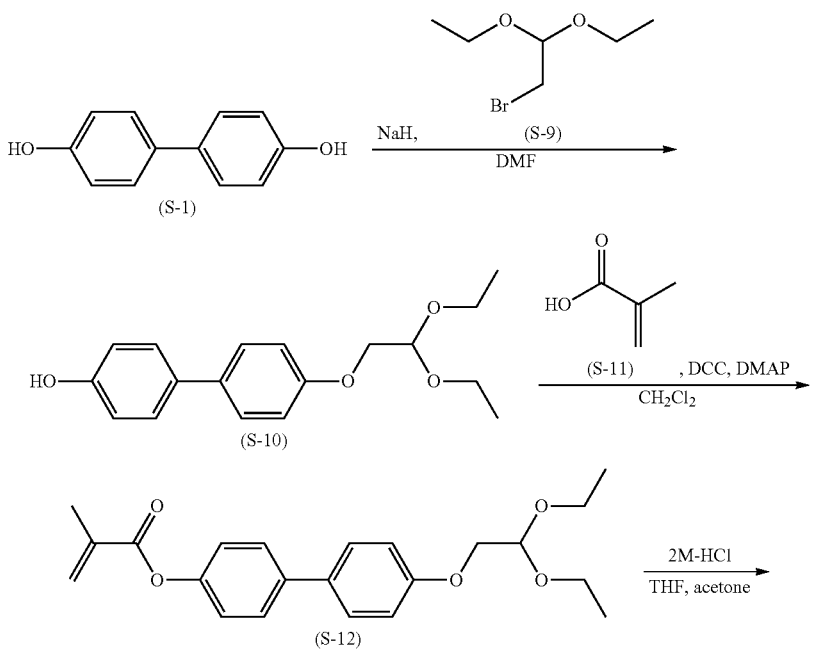

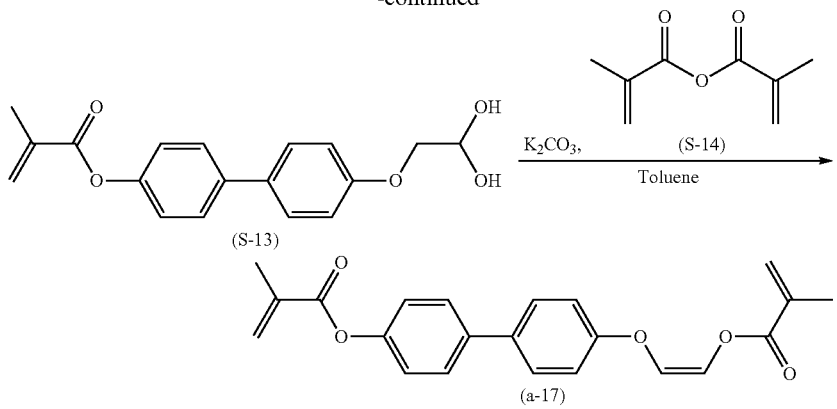

First Step: Preparation of the Compound (S-10)

A mixture of the compound (S-1) (100 g, 0.537 mol) and DMF (500 mL) was warmed at 40° C. under an atmosphere of nitrogen, to which 60%-sodium hydride (22.6 g, 0.565 mmol) was added, and the stirring was continued at 70° C. for another 1 hour. The compound (S-9) (52.9 g, 0.269 mol) was then added dropwise to the reaction mixture for 30 minutes, and the stirring was continued at 95° C. for another 2 hours. The reaction mixture was cooled at 60° C., and the mixture was poured into 0.6 M-sodium hydroxide aqueous solution (1 L). The mixture was extracted with a mixed solvent of methyl tert-butyl ether (MTBE) and hexane (1:1 by volume), and the organic layer was washed with 0.6 M-sodium hydroxide solution. The organic solvent was distilled off under reduced pressure to give the compound (S-10) as yellow oil (47.1 g).

Second Step: Preparation of the Compound (S-12)

N,N'-Dicyclohexylcarbodiimide (DCC) (33.7 g, 0.163 mmol) in dichloromethane (100 mL) solution was added dropwise to a mixture of the compound (S-10) (47.1 g, 0.156 mol), the compound (S-11) (13.4 g, 0.156 mol), 4-dimethylaminopyridine (DMAP) (1.91 g, 0.0156 mmol) and dichloromethane (800 mL) at 25° C. under an atmosphere of nitrogen, and the stirring was continued for another 15 hours. The deposit in the reaction mixture was filtered, and then the organic layer was washed with water, and dried over anhydrous magnesium sulfate. The organic solvent was distilled off under reduced pressure, and the residue was purified by silica gel column chromatography (eluent, dichloromethane: hexane=1:1 by volume) to give the compound (S-12) as colorless crystals (46.2 g).

Third Step: Preparation of the Compound (S-13)

The compound (S-12) (46.2 g, 0.125 mmol) was dissolved in a mixed solvent of acetone (300 mL) and THF (600 mL) under an atmosphere of nitrogen, to which 2M-hydrochloric acid was added dropwise at 5° C., and the stirring was continued at room temperature for another 15 hours. About 200 mL of the solvent was distilled off from the reaction mixture under reduced pressure, and the deposit in the concentrated reaction mixture was filtered. The resulting solids were dried at 50° C. for 2 hours to give the compound (S-13) as colorless crystals (31.9 g).

Fourth Step: Preparation of the Compound (a-17)

Potassium carbonate (83.8 g, 0.606 mmol) and then the compound (S-14) (155 g, 1.01 mmol) were added to a mixture of the compound (S-13) (31.9 g, 0.101 mmol) and toluene (900 mL) under an atmosphere of nitrogen, and the mixture was stirred under reflux for 40 hours. The reaction mixture was allowed to cool at room temperature, and the deposit was filtered. The solvent of the filtrate was distilled off under reduced pressure, and the residue was purified by silica gel column chromatography (eluent, 1,2-dichloroethane: hexane=3:7 by volume). The solution of the resulting crystals in hexane (100 mL) was stirred under reflux for 1 hour. After cooling, the deposit was filtered to give the compound (a-17) as colorless crystals (8.31 g)

Melting point: 111.0° C.

$^1$H-NMR (DMSO-d; δ ppm): 7.74-7.67 (m, 4H), 7.28-7.20 (m, 4H), 6.89 (d, 1H), 6.62 (d, 1H), 6.30 (s, 1H), 6.17 (s, 1H), 5.91 (s, 1H), 5.84 (s, 1H), 2.02 (s, 3H), and 1.94 (s, 3H).

The following compounds were prepared from the corresponding starting materials according to the synthetic methods shown in Examples 1 to 3.

Example 4

The Compound (a-33)

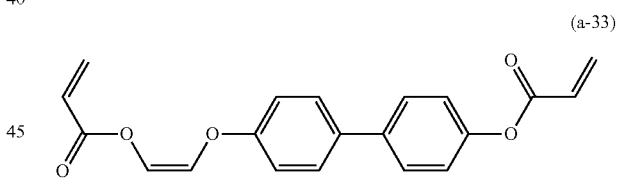

Melting point: 89.4° C.

$^1$H-NMR (CDCl$_3$; δ ppm): 7.55 (dd, 4H), 7.20 (d, 2H), 7.13 (d, 2H), 6.98 (d, 1H), 6.65-6.56 (m, 2H), 6.38-6.20 (m, 3H), 6.04 (dd, 1H), and 5.97 (dd, 1H).

Example 5

The Compound (a-16)

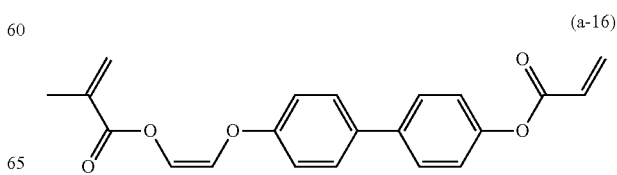

Melting point: 80.0° C.

$^1$H-NMR (CDCl$_{3-d}$; δ ppm): 7.55 (dd, 4H), 7.19 (d, 2H), 7.13 (d, 2H), 6.96 (d, 1H), 6.63 (dd, 1H), 6.37-6.29 (m, 2H), 6.18 (d, 1H), 6.04 (d, 1H), 5.71 (t, 1H), and 2.01 (s, 3H).

Example 6

The Compound (a-68)

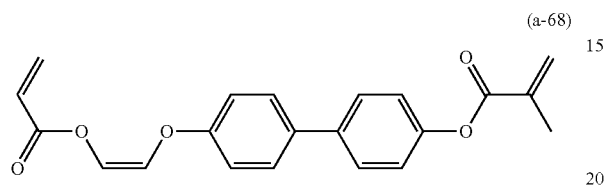

Melting point: 105.9° C.

$^1$H-NMR (CDCl$_3$; δ ppm): 7.55 (t, 4H), 7.18 (d, 2H), 7.13 (d, 2H), 6.98 (d, 1H), 6.58 (dd, 1H), 6.37 (s, 1H), 6.26 (dd, 1H), 6.20 (d, 1H), 5.97 (dd, 1H), 5.78 (t, 1H), and 2.08 (s, 3H).

Example 7

The Compound (a-31)

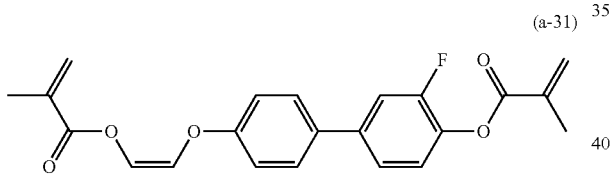

Melting point: 58.0° C.

$^1$H-NMR (CDCl$_3$; δ ppm): 7.52 (d, 2H), 7.37-7.32 (m, 2H), 7.22 (t, 1H), 7.13 (d, 2H), 6.96 (d, 1H), 6.41 (s, 1H), 6.29 (s, 1H), 6.18 (d, 1H), 5.82 (s, 1H), 5.71 (s, 1H), 2.09 (s, 3H), and 2.01 (s, 3H).

Example 8

The Compound (a-25)

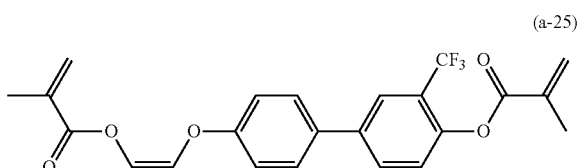

Melting point: 64.7° C.

$^1$H-NMR (CDCl$_3$-d; δ ppm): 7.82 (d, 1H), 7.74 (dd, 1H), 7.54 (d, 2H), 7.36 (d, 1H), 7.16 (d, 2H), 6.96 (d, 1H), 6.42 (s, 1H), 6.29 (s, 1H), 6.19 (d, 1H), 5.83 (s, 1H), 5.71 (s, 1H), 2.09 (s, 3H), and 2.00 (s, 3H).

Example 9

The Compound (a-261)

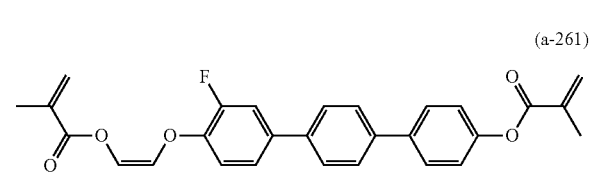 [SMILES: C=C(C)C(=O)O/C=C\Oc1ccc(-c2ccc(-c3ccc(OC(=O)C(=C)C)cc3)cc2)cc1F]

Melting point: 156.7° C.

$^1$H-NMR (CDCl$_3$-d; δ ppm): 7.66-7.59 (m, 6H), 7.42 (dd, 1H), 7.37 (dd, 1H), 7.23-7.18 (m, 4H), 6.99 (d, 1H), 6.38 (s, 1H), 6.29 (s, 1H), 6.17 (d, 1H), 5.79 (t, 1H), 5.72 (t, 1H), 2.09 (s, 3H), and 2.01 (s, 3H).

Example 10

The Compound (a-262)

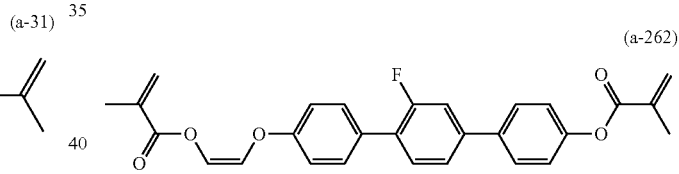

Melting point: 91.3° C.

$^1$H-NMR (CDCl$_3$-d; δ ppm): 7.64 (d, 2H), 7.57 (dd, 2H), 7.48 (t, 1H), 7.42 (dd, 1H), 7.37 (dd, 1H), 7.22 (dd, 2H), 7.15 (dd, 2H), 6.97 (d, 1H), 6.38 (s, 1H), 6.29 (s, 1H), 6.21 (d, 1H), 5.78 (t, 1H), 5.71 (t, 1H), 2.08 (s, 3H), and 2.01 (s, 3H).

Examples of the Compositions

The liquid crystal compositions of the invention will be explained in detail by way of Examples. The invention is not limited by Examples described below. The compounds described in Examples were expressed in terms of symbols according to the definition in the following Table 1. In Table 1, the configuration of 1,4-cyclohexylene is trans. The ratios (percentage) of liquid crystal compounds mean the percentages by weight (% by weight) based on the total weight of the liquid crystal composition. Last, the values of physical properties of the composition were summarized. The physical properties were measured according to the method described above, and measured values were reported here without extrapolation.

TABLE 1

Method of Description of Compound using Symbols
R—(A₁)—Z₁—...—Zₙ—(Aₙ)—R'

1) Left-terminal Group R—

| R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2=CH$— | V— |
| $C_nH_{2n+1}$—CH=CH— | nV— |
| $CH_2=CH$—$C_nH_{2n}$— | Vn— |
| $C_mH_{2m+1}$—CH=CH—$C_nH_{2n}$— | mVn— |
| $CF_2=CH$— | VFF— |
| $CF_2=CH$—$C_nH_{2n}$— | VFFn— |

2) Right-terminal Group —R'

| —R' | Symbol |
|---|---|
| —$C_nH_{2n+1}$ | -n |
| —$OC_nH_{2n+1}$ | —On |
| —$COOCH_3$ | —EMe |
| —$CH=CH_2$ | —V |
| —CH=CH—$C_nH_{2n+1}$ | —Vn |
| —$C_nH_{2n}$—$CH=CH_2$ | —nV |
| —$C_mH_{2m}$—CH=CH—$C_nH_{2n+1}$ | —mVn |
| —$CH=CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —CF=CH—$CF_3$ | —FVCF3 |
| —C≡N | —C |

3) Bonding Group —Zₙ—

| —Zₙ— | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

4) Ring Structure —Aₙ—

| Structure | Symbol |
|---|---|
|  | H |
|  | B |
| 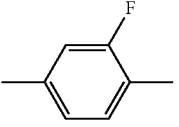 | B(F) |
| 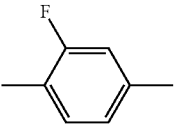 | B(2F) |
| 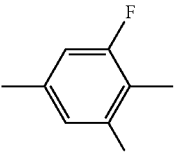 | B(F,F) |
| 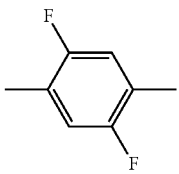 | B(2F,5F) |
| 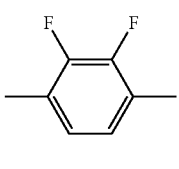 | B(2F,3F) |
| 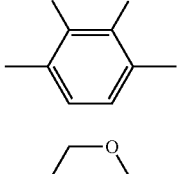 | B(2F,3CL) |
| 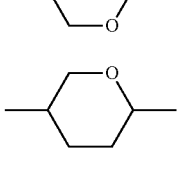 | G |
| 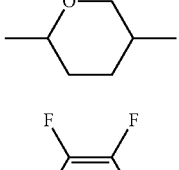 | dh |
| 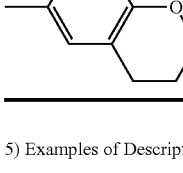 | Dh |
| 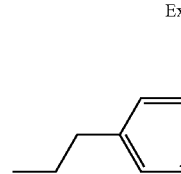 | Cro(7F,8F) |

5) Examples of Description

Example 1. 3-BB(F,F)XB(F,F)—F

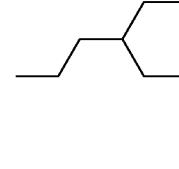

Example 2. 3HBB(2F,3F)—O2

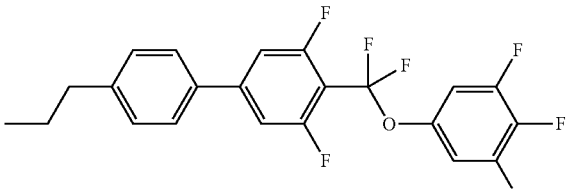

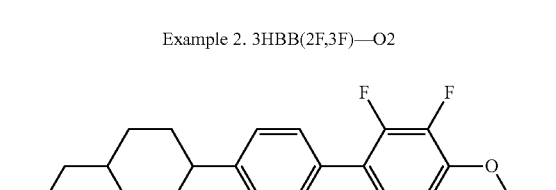

TABLE 1-continued

Method of Description of Compound using Symbols
R—(A₁)—Z₁—...—Zₙ—(Aₙ)—R'

Example 3. 3-HH-4

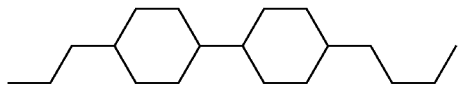 [SMILES: CCCCC1CCC(C2CCC(CCC)CC2)CC1]

Example 4. 3HBB(F,F)—F

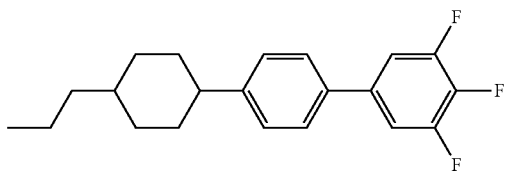 [SMILES: CCCC1CCC(c2ccc(-c3cc(F)c(F)c(F)c3)cc2)CC1]

Example 11

Use Example 1

| | |
|---|---|
| 2-HH-3 | 15% |
| 3-HH-4 | 5% |
| 3-HB—O2 | 5% |
| 3-HHB-1 | 8% |
| 3-HHB-3 | 2% |
| 3-HBB—F | 20% |
| 2-HHB(F,F)—F | 14% |
| 3-HHB(F,F)—F | 4% |
| 3-HBB(F,F)—F | 2% |
| 5-HBB(F,F)—F | 6% |
| 2-HHBB(F,F)—F | 8% |
| 3-HHBB(F,F)—F | 5% |
| 4-HHBB(F,F)—F | 6% |

0.3 Part by weight of the compound described below was added to 100 parts by weight of the composition described above.

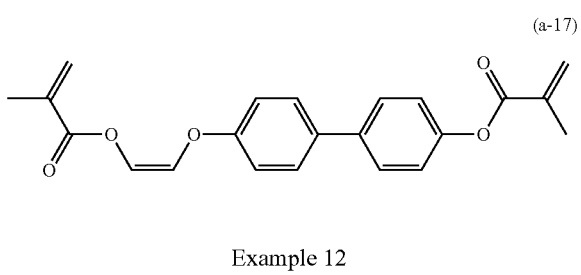

(a-17)

Example 12

Use Example 2

| | |
|---|---|
| 5-HB—CL | 16% |
| 3-HH-4 | 12% |
| 3-HH-5 | 4% |
| 3-HHB—F | 4% |
| 3-HHB—CL | 3% |
| 4-HHB—CL | 4% |
| 3-HHB(F)—F | 10% |
| 4-HHB(F)—F | 9% |
| 5-HHB(F)—F | 9% |
| 7-HHB(F)—F | 8% |
| 5-HBB(F)—F | 4% |
| 101-HBBH-5 | 3% |
| 3-HHBB(F,F)—F | 2% |
| 4-HHBB(F,F)—F | 3% |
| 5-HHBB(F,F)—F | 3% |
| 3-HH2BB(F,F)—F | 3% |
| 4-HH2BB(F,F)—F | 3% |

0.3 Part by weight of the compound described below was added to 100 parts by weight of the composition described above.

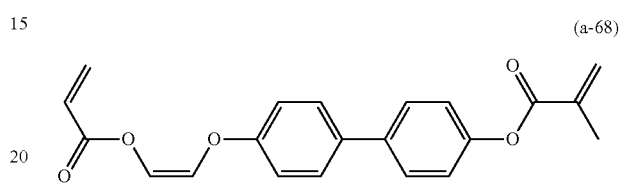

(a-68)

NI=113.9° C.; Δn=0.090; Δ∈=3.8; η=19.2 mPa·s.

Example 13

Use Example 3

| | |
|---|---|
| 3-HHB(F,F)—F | 9% |
| 3-H2HB(F,F)—F | 8% |
| 4-H2HB(F,F)—F | 8% |
| 5-H2HB(F,F)—F | 8% |
| 3-HBB(F,F)—F | 21% |
| 5-HBB(F,F)—F | 20% |
| 3-H2BB(F,F)—F | 10% |
| 5-HHBB(F,F)—F | 3% |
| 5-HHEBB—F | 2% |
| 3-HH2BB(F,F)—F | 3% |
| 101-HBBH-4 | 4% |
| 101-HBBH-4 | 4% |

0.3 Part by weight of the compound described below was added to 100 parts by weight of the composition described above.

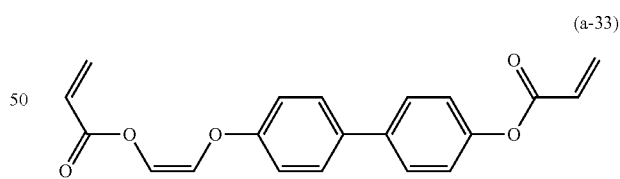

(a-33)

NI=98.8° C.; Δn=0.117; Δ∈=9.1; η=35.3 mPa·s.

Example 14

Use Example 4

| | |
|---|---|
| 5-HB—F | 12% |
| 6-HB—F | 9% |
| 7-HB—F | 7% |
| 2-HHB—OCF3 | 7% |
| 3-HHB—OCF3 | 7% |

| | |
|---|---|
| 4-HHB—OCF3 | 7% |
| 5-HHB—OCF3 | 5% |
| 3-HH2B—OCF3 | 4% |
| 5-HH2B—OCF3 | 4% |
| 3-HHB(F,F)—OCF2H | 4% |
| 3-HHB(F,F)—OCF3 | 5% |
| 3-HH2B(F)—F | 3% |
| 3-HBB(F)—F | 10% |
| 5-HBB(F)—F | 10% |
| 5-HBBH-3 | 3% |
| 3-HB(F)BH-3 | 3% |

0.3 Part by weight of the compound described below was added to 100 parts by weight of the composition described above.

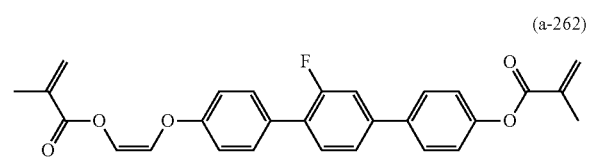 [SMILES: C=C(C)C(=O)O/C=C\Oc1ccc(-c2ccc(-c3ccc(OC(=O)C(=C)C)cc3)cc2F)cc1]

(a-262)

Example 15

Use Example 5

| | |
|---|---|
| 5-HB—CL | 11% |
| 3-HH-4 | 8% |
| 3-HHB-1 | 5% |
| 3-HHB(F,F)—F | 8% |
| 3-HBB(F,F)—F | 20% |
| 5-HBB(F,F)—F | 15% |
| 3-HHEB(F,F)—F | 10% |
| 4-HHEB(F,F)—F | 3% |
| 5-HHEB(F,F)—F | 3% |
| 2-HBEB(F,F)—F | 3% |
| 3-HBEB(F,F)—F | 5% |
| 5-HBEB(F,F)—F | 3% |
| 3-HHBB(F,F)—F | 6% |

0.3 Part by weight of the compound described below was added to 100 parts by weight of the composition described above.

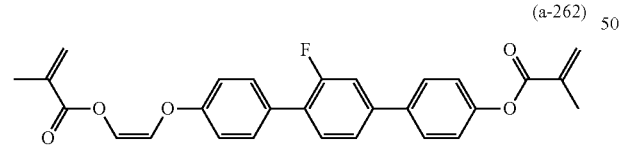

(a-262)

Example 16

Use Example 6

| | |
|---|---|
| 3-HB—CL | 6% |
| 5-HB—CL | 4% |
| 3-HHB—OCF3 | 5% |
| 3-H2HB—OCF3 | 5% |
| 5-H4HB—OCF3 | 15% |
| V-HHB(F)—F | 5% |
| 3-HHB(F)—F | 5% |
| 5-HHB(F)—F | 5% |
| 3-H4HB(F,F)—CF3 | 8% |
| 5-H4HB(F,F)—CF3 | 10% |
| 5-H2HB(F,F)—F | 5% |
| 5-H4HB(F,F)—F | 7% |
| 2-H2BB(F)—F | 5% |
| 3-H2BB(F)—F | 10% |
| 3-HBEB(F,F)—F | 5% |

0.3 Part by weight of the compound described below was added to 100 parts by weight of the composition described above.

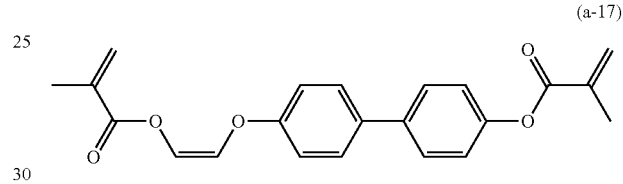

(a-17)

NI=70.4° C.; Δn=0.098; Δ∈=8.4; η=25.6 mPa·s.

Example 17

Use Example 7

| | |
|---|---|
| 5-HB—CL | 17% |
| 7-HB(F,F)—F | 3% |
| 3-HH-4 | 10% |
| 3-HH-5 | 5% |
| 3-HB—O2 | 15% |
| 3-HHB-1 | 8% |
| 3-HHB—O1 | 5% |
| 2-HHB(F)—F | 7% |
| 3-HHB(F)—F | 7% |
| 5-HHB(F)—F | 7% |
| 3-HHB(F,F)—F | 6% |
| 3-H2HB(F,F)—F | 5% |
| 4-H2HB(F,F)—F | 5% |

0.3 Part by weight of the compound described below was added to 100 parts by weight of the composition described above.

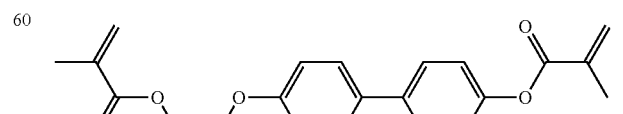

(a-17)

NI=71.7° C.; Δn=0.074; Δ∈=2.9.

Example 18

Use Example 8

| | |
|---|---|
| 5-HB—CL | 3% |
| 7-HB(F)—F | 7% |
| 3-HH-4 | 9% |
| 3-HH—EMe | 23% |
| 3-HHEB—F | 8% |
| 5-HHEB—F | 8% |
| 3-HHEB(F,F)—F | 10% |
| 4-HHEB(F,F)—F | 5% |
| 4-HGB(F,F)—F | 5% |
| 5-HGB(F,F)—F | 6% |
| 2-H2GB(F,F)—F | 4% |
| 3-H2GB(F,F)—F | 5% |
| 5-GHB(F,F)—F | 7% |

0.15 Part by weight of the compound described below was added to 100 parts by weight of the composition described above.

(a-17)

Furthermore, 0.15 part by weight of the compound described below was added.

(a-68)

NI=80.1° C.; Δn=0.065; Δ∈=5.8; η=20.1 mPa·s.

Comparative Example 1

Preparation of the Compound (R-1)

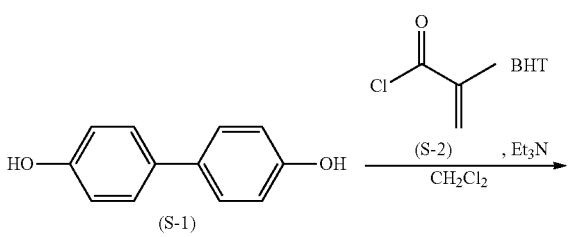

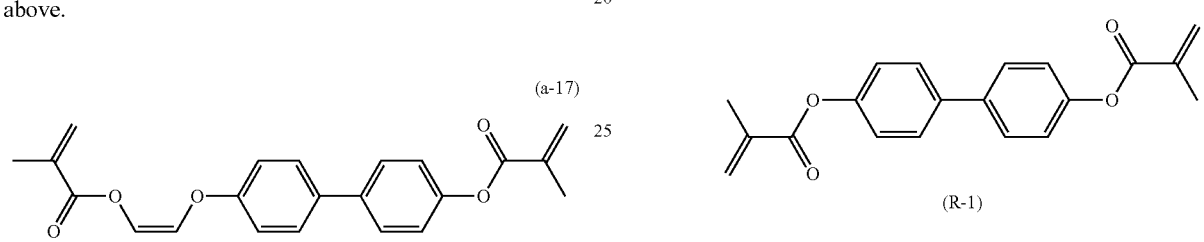

First Step:

Preparation was carried out in the same manner as in the third step of Example 2, using the compound (S-1) instead of the compound (S-8), to give colorless crystals of the compound (R-1). Melting point: 150.0° C.

$^1$H-NMR (DMSO-d; δ ppm): 7.24 (d, 4H), 6.96 (d, 4H), 6.41 (d, 2H), 6.26 (d, 2H), and 1.98 (s, 6H).

Comparative Example 2

Preparation of the Compound (R-2)

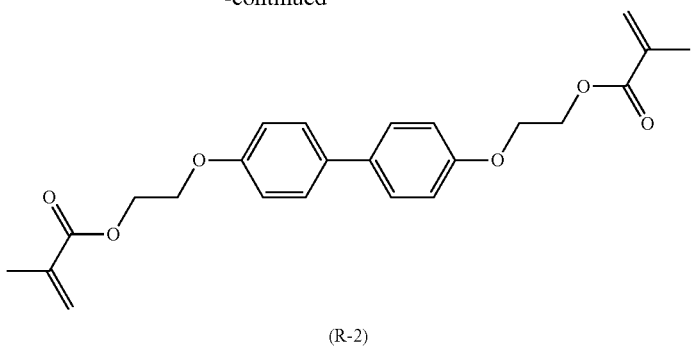

(R-2)

First Step:

The compound (S-16) (161 g, 0.845 mmol) was added dropwise to a mixture of the compound (S-15) (100 g, 0.768 mol), toluene (300 mL) and pyridine (100 mL) in an ice bath under an atmosphere of nitrogen, and the stirring was continued at room temperature for another 18 hours. Water was added, and the stirring was continued at 40° C. for another 4 hours, and then the reaction mixture was extracted with toluene. The organic layer was washed with water, and dried over anhydrous magnesium sulfate. The organic solvent was distilled off under reduced pressure to give the compound (S-17) as colorless oil (207 g).

Second Step:

Sodium hydride (55%) (16.8 g, 0.386 mmol) was added to a mixture of the compound (S-1) (30.0 g, 0.161 mmol) and DMF (200 mL) under an atmosphere of nitrogen, and the stirring was continued at 80° C. for another 1 hour. After BHT (5.000 mg, 0.0220 mmol) and DMF (600 mL) had been added to the reaction mixture, the compound (S-17) (110 g, 0.387 mmol) was added, and the stirring was continued at 60° C. for another 4 hours. Water was poured into the reaction mixture, and the mixture was extracted with toluene. The organic layer was washed with water, and dried over anhydrous magnesium sulfate, and the organic solvent was distilled off under reduced pressure. The residue was purified by silica gel column chromatography (eluent, toluene:ethyl acetate=9:1 by volume), and then by recrystallization from ethanol to give the compound (R-2) as colorless crystals (22.3 g).

Melting point: 89.0° C.

$^1$H-NMR (DMSO-d; δ ppm): 7.47 (d, 4H), 6.98 (d, 4H), 6.15 (s, 2H), 5.60 (t, 2H), 4.52 (t, 4H), 4.26 (t, 4H), and 1.96 (s, 6H).

Comparative Example 3

Comparison of Solubility in a Liquid Crystal Composition

The compound (a-17) (0.3% by weight) was added to the liquid crystal composition A, and the mixture was heated at 50° C. for 30 minutes. The liquid crystal composition dissolved was allowed to stand at room temperature for 2 days. Then, the deposition of crystals was determined by visual observation. The compound (a-262) was also measured in the same manner. On the other hand, the compound (R-1) in Comparative Example 1 and the compound (R-2) in Comparative Example 2 were also measured in the same manner. The results are shown in Table 2. In the symbols in Table 2, the symbol "○" means that crystals were not observed and the symbol "x" means that crystals were observed.

The components and their ratio of the liquid crystal composition A were as follows.

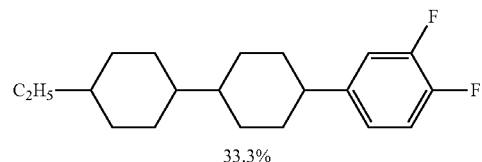

33.3%

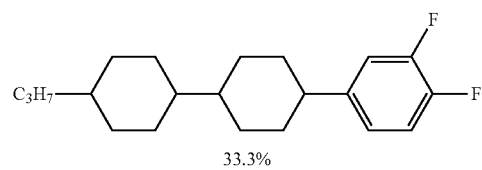

33.3%

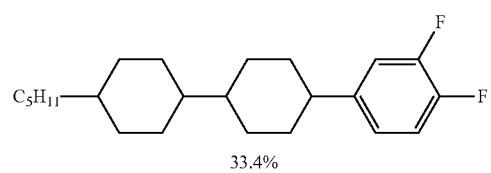

33.4%

TABLE 2

Comparison of solubility in a liquid crystal composition

| Compound Number | Structure | Solubility (at room temperature for 2 days) |
|---|---|---|
| (a-17) | ![structure] | ○ |

TABLE 2-continued

Comparison of solubility in a liquid crystal composition

| Compound Number | Structure | Solubility (at room temperature for 2 days) |
| --- | --- | --- |
| (a-262) | [structure: dimethacrylate with fluoro-terphenyl core and vinyloxy linker] | ○ |
| Comparative Example (R-1) | [structure: biphenyl dimethacrylate] | x |
| Comparative Example (R-2) | [structure: biphenyl bis(ethyleneoxy) dimethacrylate] | ○ |

From Table 2, it was found that the polymerizable compound of the invention had an excellent solubility in the liquid crystal composition A.

Comparative Example 4

Comparison of the Concentration of Residual Monomer

The polymerizable compound (a-17) (0.3% by weight) was added and dissolved in the liquid crystal composition A, which was irradiated for 273 seconds with ultraviolet light of 11 mW/cm$^2$ (Execure 4000-D made by Hoya Candeo Optronics Corporation; a mercury-xenon lamp). Then, the concentration of residual monomer was measured by HPLC. On the other hand, the compound (R-1) in Comparative Example 1 and the compound (R-2) in Comparative Example 2 were also measured in the same manner. The results are shown in Table 3. It was found, by comparison, that the concentration of residual monomer was low in the compound of the invention.

TABLE 3

Comparison of polymerizability

| Compound Number | Structure | Concentration of Residual Monomer (%) |
| --- | --- | --- |
| (a-17) | [structure: biphenyl dimethacrylate with vinyloxy linker] | 0.05 |
| Comparative Example (R-1) | [structure: biphenyl dimethacrylate] | 0.05 |

TABLE 3-continued

Comparison of polymerizability

| Compound Number | Structure | Concentration of Residual Monomer (%) |
|---|---|---|
| Comparative Example (R-2) | 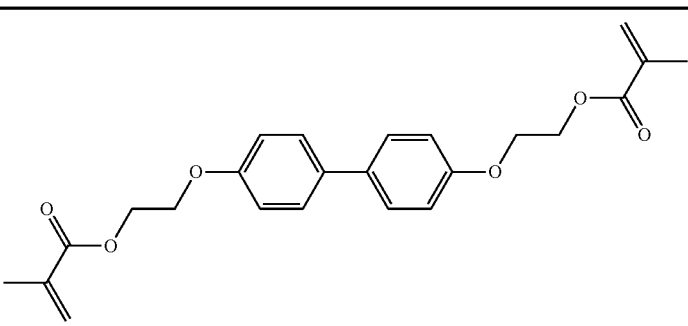 | 0.2 |

What is claimed is:

1. A compound represented by formula (1-1) or (1-2), wherein

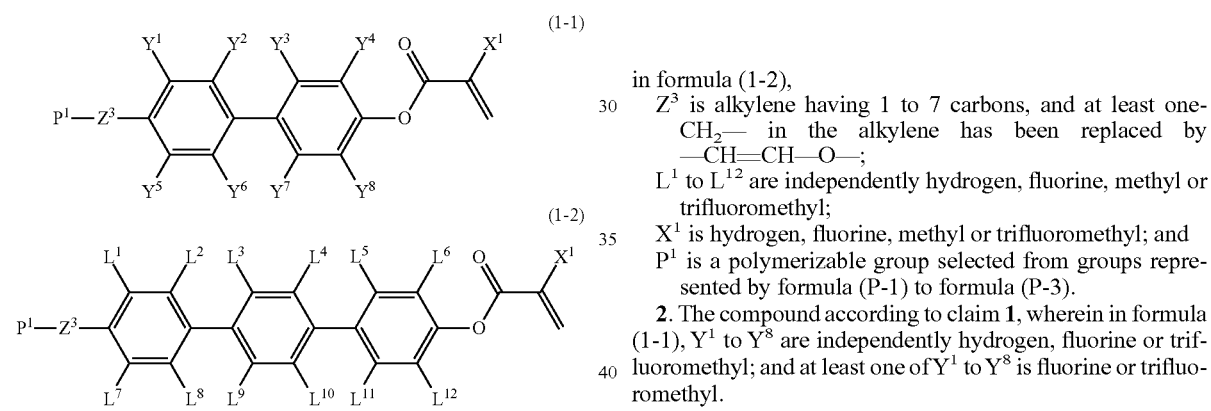

in formula (1-1),

Z³ is alkylene having 1 to 7 carbons, and at least one —CH₂— in the alkylene has been replaced by —CH=CH—O—;

Y¹ to Y⁸ are independently hydrogen, fluorine, methyl or trifluoromethyl;

X¹ is hydrogen, fluorine, methyl or trifluoromethyl; and

P¹ is a polymerizable group selected from groups represented by formula (P-1) to formula (P-3),

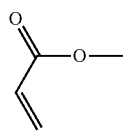
(P-1)

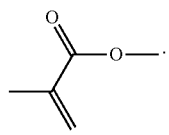
(P-2)

(P-3)

in formula (1-2),

Z³ is alkylene having 1 to 7 carbons, and at least one —CH₂— in the alkylene has been replaced by —CH=CH—O—;

L¹ to L¹² are independently hydrogen, fluorine, methyl or trifluoromethyl;

X¹ is hydrogen, fluorine, methyl or trifluoromethyl; and

P¹ is a polymerizable group selected from groups represented by formula (P-1) to formula (P-3).

2. The compound according to claim 1, wherein in formula (1-1), Y¹ to Y⁸ are independently hydrogen, fluorine or trifluoromethyl; and at least one of Y¹ to Y⁸ is fluorine or trifluoromethyl.

3. The compound according to claim 1, wherein in formula (1-1), X¹ is hydrogen or methyl; and all of Y¹ to Y⁸ are hydrogen.

4. The compound according to claim 1, wherein in formula (1-1), P¹ is a group selected from groups represented by formula (P-1) and formula (P-2):

(P-1)

(P-2)

5. The compound according to claim 1, wherein in formula (1-1), $P^1$ is the group represented by formula (P-3):

(P-3)

6. The compound according to claim 1, wherein in formula (1-2), $L^1$ to $L^{12}$ are independently hydrogen, fluorine or trifluoromethyl; and at least one of $L^1$ to $L^{12}$ is fluorine or trifluoromethyl.

7. The compound according to claim 1, wherein in formula (1-2), $X^1$ is hydrogen or methyl; and all of $L^1$ to $L^{12}$ are hydrogen.

8. The compound according to claim 1, wherein in formula (1-2), $P^1$ is a group selected from groups represented by formula (P-1) and formula (P-2):

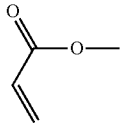
(P-1)

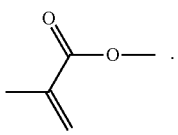
(P-2)

9. The compound according to claim 1, wherein in formula (1-2), $P^1$ is a group represented by formula (P-3):

(P-3)

10. A composition including the compound according to claim 1.

11. The composition according to claim 10, wherein the compound is added to a non-polymerizable liquid crystal composition.

12. The composition according to claim 10, further including at least one compound selected from the group of compounds represented by formula (2) to formula (4), wherein

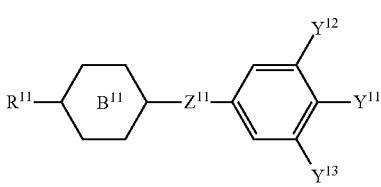
(2)

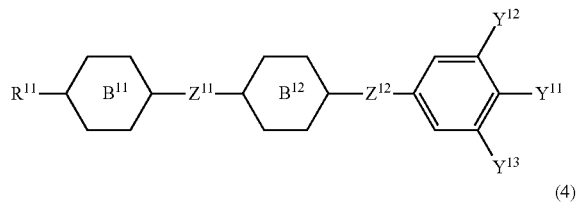
(3)

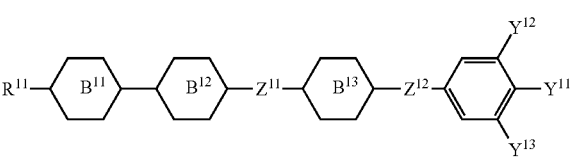
(4)

in formula (2) to formula (4),
$R^{11}$ is independently alkyl having 1 to 10 carbons or alkenyl having 2 to 10 carbons, and hydrogen in the alkyl and alkenyl are not replaced or at least one hydrogen is replaced by fluorine and —$CH_2$— in the alkylene are not replaced or at least one —$CH_2$— is replaced by —O—;
the ring $B^{11}$, the ring $B^{12}$; and the ring $B^{13}$ are independently 1,4-cyclohexenylene, 1,3-dioxane-2,5-diyl, tetrahydropyran-2,5-diyl, or 1,4-phenylene in which hydrogen in these groups are not replaced or at least one hydrogen is replaced by fluorine;
$Z^{11}$ and $Z^{12}$ are independently —$(CH_2)_2$—, —$(CH_2)_4$—, —COO—, —$CF_2O$—, —$OCF_2$—, —CH=CH—, —C≡C—, —$CH_2O$— or a single bond;
$Y^{11}$ is independently fluorine, chlorine, —$OCF_3$, —$OCHF_2$, —$CF_3$, —$CHF_2$, —$CH_2F$, —$OCF_2CHF_2$ or —$OCF_2CHFCF_3$; and
$Y^{12}$ and $Y^{13}$ are independently hydrogen or fluorine.

13. The composition according to claim 12, further including at least one compound selected from the group of compounds represented by formula (5) to formula (7), wherein

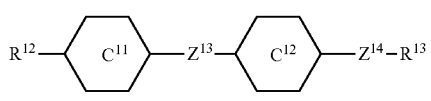
(5)

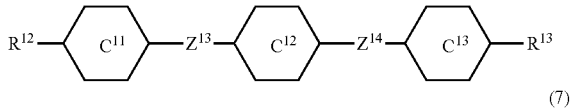
(6)

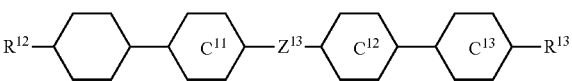
(7)

in formula (5) to formula (7),
$R^{12}$ and $R^{13}$ are independently alkyl having 1 to 10 carbons or alkenyl having 2 to 10 carbons, and hydrogen in the alkyl and alkenyl are not replaced or at least one hydrogen is replaced by fluorine and —$CH_2$— in the alkyl and alkenyl are not replaced or at least one —$CH_2$— is replaced by —O—;
the ring $C^{11}$, the ring $C^{12}$ and the ring $C^{13}$ are independently 1,4-cyclohexenylene, 1,4-phenylene, 2-fluoro-1,4-phenylene or 2,5-difluoro-1,4-phenylene; and
$Z^{13}$ and $Z^{14}$ are independently —$(CH_2)_2$—, —COO—, —CH=CH—, —C≡C— or a single bond.

14. A polymer obtained by the polymerization of the compound according to claim 1.

15. A polymer obtained by the polymerization of the composition according to claim 10.

16. A liquid crystal display device containing the composition according to claim 10.

* * * * *